(12) United States Patent
Aponick et al.

(10) Patent No.: US 11,198,701 B2
(45) Date of Patent: Dec. 14, 2021

(54) BIARYL LIGANDS, METHODS OF MAKING BIARLYL LIGANDS, AND METHODS OF USE THEREOF

(71) Applicant: University of Florida Research Foundation, Inc., Gainesville, FL (US)

(72) Inventors: Aaron Aponick, Gainesville, FL (US); Flavio S. P. Cardoso, Sao Paulo (BR)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 16/792,794

(22) Filed: Feb. 17, 2020

(65) Prior Publication Data

US 2020/0223878 A1  Jul. 16, 2020

Related U.S. Application Data

(63) Continuation of application No. 15/927,505, filed on Mar. 21, 2018, now Pat. No. 10,618,922, which is a continuation of application No. 15/021,053, filed as application No. PCT/US2014/055356 on Sep. 12, 2014, now Pat. No. 9,994,599.

(60) Provisional application No. 61/877,505, filed on Sep. 13, 2013, provisional application No. 61/881,480, filed on Sep. 24, 2013.

(51) Int. Cl.
| | |
|---|---|
| *C07F 9/6506* | (2006.01) |
| *C07D 233/20* | (2006.01) |
| *B01J 31/24* | (2006.01) |
| *C07C 209/22* | (2006.01) |
| *C07C 213/02* | (2006.01) |
| *C07D 211/74* | (2006.01) |
| *C07F 7/08* | (2006.01) |

(52) U.S. Cl.
CPC ......... *C07F 9/6506* (2013.01); *B01J 31/2447* (2013.01); *C07C 209/22* (2013.01); *C07C 213/02* (2013.01); *C07D 211/74* (2013.01); *C07D 233/20* (2013.01); *C07F 7/083* (2013.01); *B01J 2231/766* (2013.01)

(58) Field of Classification Search
CPC ..... C07F 9/6506; C07F 7/083; B01J 31/2447; B01J 2231/766; C07C 209/22; C07C 213/02; C07D 211/74; C07D 233/20
USPC .......................................................... 546/14
See application file for complete search history.

(56) References Cited

U.S. PATENT DOCUMENTS

2005/0277772 A1   12/2005   Carriera

FOREIGN PATENT DOCUMENTS

WO   9513284   5/1995

OTHER PUBLICATIONS

Bringmann, et al., "Atroposelective Synthesis of Axially Chiral Biaryl Compounds", Angewandte Chemie International Edition. vol. 44, Issue 34, pp. 5384-5427, Aug. 26, 2005.
Li, et al., "Recent Advances in Developing New Axially Chiral Phosphine Ligands for Asymmetric Catalysis", Coordination Chemistry Reviews. vol. 251, Issues 17-20, Sep. 2007, pp. 2119-2144.

(Continued)

*Primary Examiner* — Taylor V Oh
(74) *Attorney, Agent, or Firm* — Thomas|Horstemeyer LLP

(57) ABSTRACT

Embodiments of the present disclosure provide for biaryl ligands (also referred to herein as "biaryl compound"), biaryl complexes, methods of making biaryl compounds, methods of making single enantiomers of these biaryl compounds, methods of use (e.g., catalysis), and the like.

8 Claims, 29 Drawing Sheets

(56) References Cited

OTHER PUBLICATIONS

Noyori, R ; Takaya, H., BINAP: An Efficient Chiral Element for Asymmetric Catalysis. Acc. Chem. Res. 1990, 23, 345-350.
Berthod, M.; Mignani, G.; Woodward, G.; Lemaire, M., Modified BINAP: The How and the Why. Chem. Rev. 2005, 105, 1801-1836.
Shimizu, H.; Nagasaki, I.; Saito, T., Recent advances in biaryl-type bisphosphine ligands. Tetrahedron 2005, 61, 5405-5432.
Yoon, T. P.; Jacobsen, E. N., Privileged Chiral Catalysts. Science 2003, 299, 1691.
Alcock, N. W.; Brown, J. M.; Hulmes, D. I., Synthesis and Resolution of I-(2-Diphenylphosphino-lnaphthyl)isoquinoline a P-N Chelating Ligand for Asymmetric Catalysis. Tetrahedron: Asymmetry 1993, 4, 743-756.
Knopfel, T. F.; Aschwanden, P.; Ichikawa, T.; Watanabe, T.; Carreira, E. M., Readily available biaryl P,N ligands for asymmetric catalysis Angew. Chem., Int. Ed. 2004, 43, 5971-5973.
Alkorta, I.; Elguero, J.; Roussel, C.; Vanthuyne, N.; Piras, P., Atropisomerism and Axial Chirality in Heteroaromatic Compounds. Adv. Heterocycl. Chem. 2012, 105, 1-188.
Claridge, T. D. W.; Long, J. M.; Brown, J. M.; Hibbs, D.; Hursthouse, M. B., Synthesis of 1-Methyl-2-diphenylphosphino-3-(1'-isoquinolyl)indole; an Easily Racemised Ligand giving Insights into Catalytic Asymmetric Allylation. Tetrahedron 1997, 53, 4035-4050.
Birkholz, M.-N.; Freixa, Z.; van Leeuwen, P. W. N. M., Bite angle effects of diphosphines in C—C and C—X bond Forming cross coupling reactions. Chem. Soc. Rev., 2009, 38, 1099-1118.
Andersen, N.G., Keay, B. A., 2-Furyl Phosphines as Ligands for Transition-Metal-Mediated Organic Synthesis Chem. Rev. 2001, 101, 997-1030.
Meyer, E. A.; Castellano, R. K.; Diederich, F., Interactions with Aromatic Rings in Chemical and Biological Recognition. Angew. Chem., Int. Ed. 2003, 42, 1210-1250.
Salonen, L. M.; Ellermann, M., Diederich, F., Aromatic Rings in Chemical and Biological Recognition: Energetics and Structures. Angew. Chem., Int. Ed. 2011, 50, 4808-4842.
Sutherland, I. O., The investigation of the kinetics of conformational changes by nuclear magnetic resonance spectroscopy. Annu. Rep. NMR Spectrosc. 1971, 4, 71-235.
Haynes, S. W.; Sydor, P. K.; Stanley, A. E.; Song, L.; Challis, G. L., Role and subsliate specificity of the Streptomyces coelicolor RedHenzyme in undecylprodiginine biosynthesis. Chem. Commun., 2008, 1865-1867.
Clift, M. D.; Thomson, R. J. Development of a Merged Conjugate Addition/Oxidative Coupling Sequence. Application to the Enantioselective Total Synthesis of Metacycloprodigiosin and Prodigiosin R1. J. Am. Chem. Soc. 2009, 131, 14579-14583.
Hasan, I.; Marinelli, E. R.; Lin, L. C. C.; Fowler, F. W.; Levy, A. B., Synthesis and Reactions of N-Protected 2-Lithiated Pyrroles and Indoles. The tert-Butoxycarbonyl Substituent as a Protecting Group. J. Org. Chem. 1981, 46, 157-164.
Schlosser, M.; Michel, D., Introduction of fluorine into organic molecules: why and how. Tetrahedron 1996, 52, 99-108.
Figge, A., Altenbach, H.J., Brauerb, D.J., Tielmannc, P., Synthesis and resolution of 2-(2-diphenylphosphinyl-naphthalen-1-yl)-1-isopropyl-1Hbenzoimidazole; a new alropisomeric P,N-chelating ligand for asymmetric catalysis. Tetrahedron: Asymmetry 2002, 13, 137-144.
Kwong, F. Y.; Chan, A. S. C.; Chan, K. S., Chelating Retardation Effect in Nickel Assisted Phosphination: Syntheses ol Atropisomeric P,N Ligands. Tetrahedron 2000, 56, 8893-8899.
Otsuka, S.; Nakamura, A.; Kano, T.; Tani, K., Partial Resolution of Racemic Tertiary Phosphines with an Asymmetric Palladium Complex. J. Am. Chem. Soc. 1971, 93, 4301-4303.
Tani, K.; Brown, L. D.; Ahmed, J.; Ibers, J. A.; Yokota, M.; Nakamura, A.; Otsuka, S., Chiral Metal Complexes. 4. Resolution of Racemic Tertiary Phosphines with Chiral Palladium(II) Complexes. The Chemistry of Diastereomeric Phosphine Pd(II) Species in Solution, and the Absolute Configuration of [(S)-Isopropyl-tert-butylphenylphosphine]-[(R)-N,N-dimethyl-(2-naphthyl)-ethylamine-3C,N]chloropalladium(II) Determined by X-Ray Diffraction. J. Am. Chem. Soc. 1977, 99, 7876-7886.
Allen, D. G.; Mclaughlin, G. M.; Robertson, G. B.; Steffen, W. L.; Salem, G.; Wild, S. B., Resolutions with metal complexes. Preparation and resolution of (R,S)-methylphenyl(8-quinolyl)phosphine and its arsenic analog. Crystal and molecular structure of (+)589-[(R)-dimethyl(1-ethyl-naphthyl)aminato-C2,N][(S)-methylphenyl(8-quinolyl)phosphine] palladium(II) hexafluorophosphate. Inorg. Chem. 1982, 21, 1007-1014.
Brown, J. M.; Hulmes, D. L; Guiry, P. J., Mechanistic and Synthetic Studies in Catalytic Allylic Alkylation with Palladium Complexes of1-(2-Diphenylphosphino-1-naphthyl)isoquinoline. Tetrahedron 1994, 50, 4493-4506.
Yamaguchi, M.; Shima, T.; Yamagishi, T.; Hida, M., Palladium-catalyzed asymmetric allylic alkylation using dimethyl malonate and its derivatives as nucleophile. Tetrahedron: Asymmetry 1991, 2, 663-666.
Gommermann, N.; Koradin, C.; Polbom, K.; Knochel, P., Enantioselective, Copper(I)-Catalyzed Three-Component Reaction for the Preparation of Propargylamines. Angew. Chem. Int. Ed. 2003, 42, 5763-5766.
Gommermann, N.; Knochel, P., Practical Highly Enantioselective Synthesis of Propargylamines through a Copper-Catalyzed One-Pot Three-Component Condensation Reaction. Chem. Eur. J. 2006, 12, 4380-4392.
Peshkov, V. A.; Pereshivko, O. P.; Van der Eycken, E. V., A walk around the A3-coupling. Chem. Soc. Rev. 2012, 41, 3790-3807.
McCartney, D.; Guiry, P. J., The asymmetric Heck and related reactions. Chem. Soc. Rev. 2011, 40, 5122-5150.
Marion, N.; Diez-Gonzalez, S.; Nolan, S. P., N-heterocyclic carbenes as organocatalysts Angew. Chem., Int. Ed. 2007, 46, 2988-3000.
McCarthy, M.; Guiry, P. J., Axially chiral bidentate ligands in asymmetric catalysis, Tetrahedron 2001, 57, 3809-3844.
Brunel, J. M., BINOL: A Versatile Chiral Reagent, Chem. Rev. 2005, 105, 857-897.
Chen, Y.; Yekta, S.; Yudin, A. K., Modified BINOL Ligands in Asymmetric Catalysis, Chem. Rev. 2003, 103, 3155-3211.
Oki, M., Recent Advances in Atropisomerism, Top. Stereochem. 1983, 14, 1-76.
Lim, C. W.; Tissot, O.; Mattison, A.; Hooper, M. W.; Brown, J. M.; Cowley, A. R.; Hulmes, D I.; Blacker, A. J., Practical Preparation and Resolution of 1-(2'-Diphenylphosphino-1'-naphthyl)isoquinoline: A Useful Ligand for Catalytic Asymmetric Synthesis, Org. Process Res. Dev. 2003, 7, 379-384.
Carroll, A.; O'Sullivan, T. P.; Guiry, P. J., The Development of Enantioselective Rhodium-Catalysed Hydroboration of Olefins Adv. Synth. Catal. 2005, 347, 609-631.
Doucet, H.; Fernandez, E.; Layzell, T. P.; Brown, J. M., The Scope of Catalytic Asymmetric Hydroboration/Oxidation with Rhodium Complexes of 1,1'-(2-Diarylphosphino-1-naphthyl)isoquinolines Chem. Eur. J. 1999, 5, 1320-1330.
Morgan, J. M.; Miller, S. P.; Morken, J. P. J., Rhodium-Catalyzed Enantioselective Diboration of Simple Alkenes, Am. Chem. Soc. 2003, 125, 8702-8703.
Fujimori, S.; Knopfel, T. F.; Zarotti, P.; Ichikawa, T.; Boyall, D.; Carreira, E. M., Stereoselective Conjugate Addition Reactions Using In Situ Metallated Terminal Alkynes and the Development of Novel Chiral P,N-Ligands, Bull. Chem. Soc. Jpn. 2007, 80, 1635-1657.
Knopfel, T. F.; Zarotti, P.; Ichikawa, T.; Carreira, E. M., Catalytic, Enantioselective, Conjugate Alkyne Addition, J. Am. Chem. Soc. 2005, 127, 9682-9683.
Lim, A. D.; Codelli, J. A.; Reisman, S. E., Catalytic Asymmetric Synthesis of Highly Substituted Pyrrolizidines, Chem. Sci., 2013, 4, 650-654.
Chen, C.; Li, X.; Schreiber, S. L., Catalytic Asymmetric [3+2] Cycloaddition of Azomethine Ylides. Development of a Versatile Stepwise, Three-Component Reaction for Diversity-Oriented Synthesis, J. Am. Chem. Soc. 2003, 125, 10174-10175.
Kostas, L D., Recent Advances on P,N-Containing Ligands for Transition-Metal Homogeneous Catalysis, Curr. Org. Synth., 2008, 5, 227-249.

(56) References Cited

OTHER PUBLICATIONS

Guiry, P. J.; Saunders, C. P., The Development of Bidentate P,N Ligands for Asymmetric Catalysis, Adv. Synth. Catal. 2004, 346, 497-537.

Carroll, M. P.; Guiry, P. J.; Brown, J. M., Meta-analysis in asymmetric catalysis. Influence of, chelate geometry on the roles of PN chelating ligands, Org. Biomol. Chem., 2013, 11, 4591-4601.

Berens, U.; Brown, J. M.; Long, J.; Seike, R., Synthesis and Resolution of 2,2'-bis-diphenylphosphino [3,3']biindolyl; a New Atropisomeric Ligand for Transition Metal Catalysis, Tetrahedron: Asymmetry 1996, 7, 285-292.

Benincori, T.; Brenna, E.; Sannicolb, F.; Trimarco, L.; Antognazza, P.; Cesarotti, E.; Demartin, F.; Pilati, T., New Class of Chiral Diphosphine Ligands for Highly Efficient Transition Metal-Catalyzed Stereoselective Reactions: The Bis (diphenylphosphino) Five-membered Biheteroaryls, J. Org. Chern. 1996, 61, 6244-6251.

Benincori, T.; Brenna, E.; Sannicolò, F.; Trimarco, L.; Antognazza, P.; Cesarotti, E.; Zotti, G., Chiral atropisomeric five-membered biheteroaromatic diphosphines: new ligands of the bibenzimidazole and biindole series, J. Organomet. Chem. 1997, 529, 445-453.

Benincori, T.; Cesarotti, E.; Piccolo, O.; Sannicolò, F., 2,2',5,5-Tetramethyl-4,4'-bis(diphenylphoshino)-3,3'-bithiophene: A New, Very Efficient, Easily Accessible, Chiral Biheteroaromatic Ligand for Homogeneous Stereoselective Catalysis, J. Org. Chem. 2000, 65, 2043-2047.

Benincori, T.; Piccolo, O.; Rizzo, S.; Sannicolò, F., 3,3'-Bis(diphenylphosphino)-1,1'-disubstituted-2,2'-biindoles: Easily Accessible, Electron-Rich, Chiral Diphosphine Ligands for Homogeneous Enantioselective Hydrogenation of Oxoesters, J. Org. Chem. 2000, 65, 8340-8347.

Andersen, N. G.; Parvez, M.; Keay, B. A., Synthesis, Resolution, and Applicationsof 2,2'-Bis(diphenylphosphino)-3,3'-binaphtho[2,1-b]furan, Org. Lett. 2000, 2, 2817-2820.

Benincori, T.; Gladiali, S.; Rizzo, S.; Sannicolò, F., A New Modular Class of Easily Accessible, Inexpensive, and Efficient Chiral Diphosphine Ligands for Homogeneous Stereoselective Catalysis, J. Org. Chem. 2001, 66, 5940-5942.

Eseola, A. O.; Obi-Egbedi, N. O, Spectroscopic study of 2-, 4- and 5-substituents on pKa values on imidazole heterocycles prone to inlramolecular proton-electrons transfer, Spectrochim. Acta A 2010, 75, 693-701.

Yoo, W.-J.; L. Zhao, L.; Li, C.-J., The A3-Coupling (Aldehyde-Alkyne-Amine) Reaction: A Versatile Method for the Preparation of Propargyl Amines, Aldrichimica Acta 2011, 44, 43-51.

Gommermann, N.; Knochel, P., Practical highly enantioselective synthesis of terminal propargylamines. An expeditious synthesis of (S)-(1)coniine, Chern. Commun. 2004, 2324-2325.

Li, Y.-M.; Kwong, F.-Y.; Yu, W.-Y.; Chan, A. S. C., Recent advances in developing new axially chiral phosphine ligands tor asymmetric catalysis, Coord. Chem. Rev. 2007, 251, 2119-2144.

Anderson, N. G., Developing Processes for Crystallization-Induced Asymmetric Transformation, Org. Process Res. Dev. 2005, 9, 800-813.

Gung, B. W.; Xue, X.; Zou, Y., Enthalpy ($\Delta H$) and Entropy ($\Delta S$) for $\pi$-Stacking Interactions in Near-Sandwich Configurations: Relative Importance of Electrostatic, Dispersive, and Charge-Transfer Effects, J. Org. Chem. 2007, 72, 2469-2475.

Muller, C.; Pidko, E. A.; Staring, A. J. P. M.; Lutz, M.; Spek, A. L.; van Santen, R. A.; Vogt, D., Developing a New Class of Axial Chiral Phosphorus Ligands: Preparation and Characterization of Enantiopure Atropisomeric Phosphinines, Chem. Eur. J. 2008, 14, 4899-4905.

Aschwanden, P.; Stephenson, C. R. J.; Carreira, E. M., Highly Enantioselective Access to Primary Propargylamines: 4-Piperidinone as a Convenient Protecting Group, Org. Lett. 2006, 8, 2437-2440.

McCarthy, M.; Goddard, R.; Guiry, P. J., The preparation and resolution of 2-phenyl-Quinazolinap, a new atropisomeric phosphinamine ligand for asymmetric catalysis, Tetrahedron: Asymmetry 1999, 10, 2797-2807.

Connolly, D. J.; Lacey, P. M.; McCarthy, M.; Saunders, C. P.; Carroll, A.-M.; Goddard, R.; Guiry, P. J., Preparation and Resolution of a Modular Class of Axially Chiral Quinazoline-Containing Ligands and Their Application in Asymmetric Rhodium-Catalyzed Olefin Hydroboration, J. Org. Chem. 2004, 69, 6572.

Fernández, E.; Guiry, P J.; Connole, K. P. T.; Brown, J. M., Quinap and Congeners: Atropos PN ligands for Asymmetric Catalysis, J. Org. Chem. 2014, 79, 5391-5400.

Cardoso, F. S. P.; Abboud, K. A.; Aponick, A., Design, Preparation, and Implementation of an Imidazole-Based Chiral Biaryl P,N-Ligand for Asymmetric Catalysis, J. Am. Chem. Soc., 2013, 135, 14548-14551.

Chung, K. H.; So, C. M.; Wong, S. M.; Luk, C. H.; Zhou,Z.; Lau, C. P.; Kwong, F. Y., An efficient palladium-benzimidazolyl phosphine complex for the Suzuki-Miyaura coupling of aryl mesylates: facile ligand synthesis and metal complex characterization, Chem. Commun. 2012, 48, 1967-1969.

Song, B.; Knauber, T.; Gooßen, L., Decarboxylative Cross-Coupling of Mesylates Catalyzed by Copper/Palladium Systems with Customized Imidazolyl Phosphine Ligands, J. Angew. Chem., Int. Ed. 2013, 52, 2954-2958.

Singer, R. A.; Caron, S.; McDermott, R. E.; Arpin, P.; Do, N. M., Alternative Biarylphosphines for Use in the Palladium-Catalyzed Amination of Aryl Halides, Synthesis 2003, 11, 1727-1731.

Fromm, A.; van Wllen, C.; Hackenberger, D.; Gooßen, L., Mechanism of Cu/Pd-Catalyzed Decarboxylative CrossCouplings: A DFT Investigation, J. Am. Chem. Soc., 2014, 136, 10007-10023.

Wong, S. M.; So, C. M.; Chung, K. H.; Lau, C. P.; Kwong, F. Y., An Efficient Class of P,N-Type "PhMezole-phos" Ligands: Applications in Palladium-Catalyzed Suzuki Coupling of Aryl Chlorides, Eur. J. Org. Chem. 2012, 4172-4177.

Clayden, J.; Moran, W. J.; Edwards, P. J.; LaPante S. R., The Challenge of Atropisomerism in Drug Discovery, Angew. Chem. Int. Ed. 2009, 48, 6398.

Bringmann, G.; Guider, T.; Guider, T. A. M.; Breuning, M., Atroposelective Total Synthesis of Axially Chiral Biaryl Matural Products, Chem. Rev. 2011, 111, 563-639.

Bringmann, G.; Price Mortimer, A. J.; Keller, P. A.; Gresser, M. J.; Gamer, J.; Breuning, M., Angew. Chern., Atroposelective Synthesis of Axially Chiral Biaryl Compounds, Int. Ed. 2005, 44, 5384-5427.

Ohkubo, M.; Hayashi, D.; Oikawa, D.; Fukuhara, K.; Okamoto, S.; Sato, F., Synthesis of N-substituted 2-arylpyrroles by the reaction of (g2-imine)titanium complexes with 3,3-diethoxypropyne, Tetrahedron Lett. 2006, 47, 6209-6212.

D. Sutherland, The Investigation of the Kinetics of Conformational Changes by Nuclear Magnetic Resonance Spectroscopy, Annu. Rep. NMR Spectrosc., 1971, 4, 71.

Mati, I. K.; Cockroft, S. L., Molecular balances for quantifying non-covalent interactions, Chem. Soc. Rev. 2010, 39, 4195-4205.

Patrick, R.; Prosser, G. S., A Molecular Complex of Benzene and Hexaflourobenzene, Nature 1960, 187, 1021.

Williams, J. H.; Cockcroft, J. K.; Fitch, A. N., Structure of the Lowest Temperature Phase of the Solid Benzene-Hexaflourobenzene Adduct, Angew. Chem., Int. Ed. Engl. 1992, 31, 1655-1657.

Bott, G.; Field, L-D.; Sternhell, S., Steric Effects. A Study of a Rationally Designed System, J. Am. Chern. Soc. 1980, 102, 5618-5626.

Rieger, M.; Westheimer, F. H., The Calculation and Determination of the Buttressing Effect for the Racemization of 2,2',3,3'-Tetraiodo-5,5'-dicarboxybiphenyl, J. Am. Chem. Soc. 1950, 72, 19-28.

Alcock, N. W.; Hulmes, D. I.; Brown, J. M., Conliasting Behaviour of Related Palladium Complex-derived Resolving Agents. 8-H Conformational Locking of the I-Naphthyl, Side-chain, J. Chem. Soc., Chern. Commun. 1995, 395-397.

Carroll, M. P.; Guiry, P., P,N ligands in asymmetric catalysis, J. Chem. Soc. Rev. 2014, 43, 819.

Kwong, F. Y.; Yang, Q.; Mak, T. C. W.; Chan, A. S. C.; Chan, K. S., A New Atropisomeric P,N Ligand for Rhodium-Catalyzed Asymmetric Hydroboration, J. Org. Chem. 2002, 67, 2769-2777.

Koradin, C.; Gommermann, N.; Polbom, K.; Knochel, P., Synthesis of Enantiomerically Enriched Propargylamines by Copper-Catalyzed Addition of Alkynes to Enamines, Chem. Eur. J. 2003, 9, 2797-2811.

(56) References Cited

OTHER PUBLICATIONS

Fleming, W. J.; Muller-Bunz, H.; Lillo, V.; Fernandez, E.; Guiry, P., Axially chiral P-N ligands for the copper catalyzed b-borylation of a,b-unsaturated esters, J. Org. Biomol. Chem. 2009, 7, 2520-2524.

Shishkov, I. V.; Rominger, F.; Hofmann, P., Reversible subsliate binding at copper centers in neutral copper(I) carbene complexes derived from bis(3-tert-butylimidazole-2-ylidene)methane, Dalton Trans. 2009, 1428-1435.

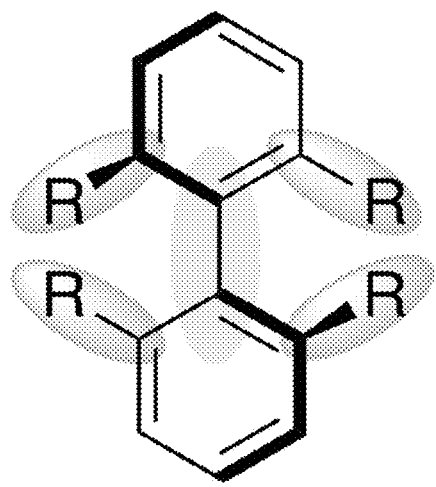
Fig. 1.1
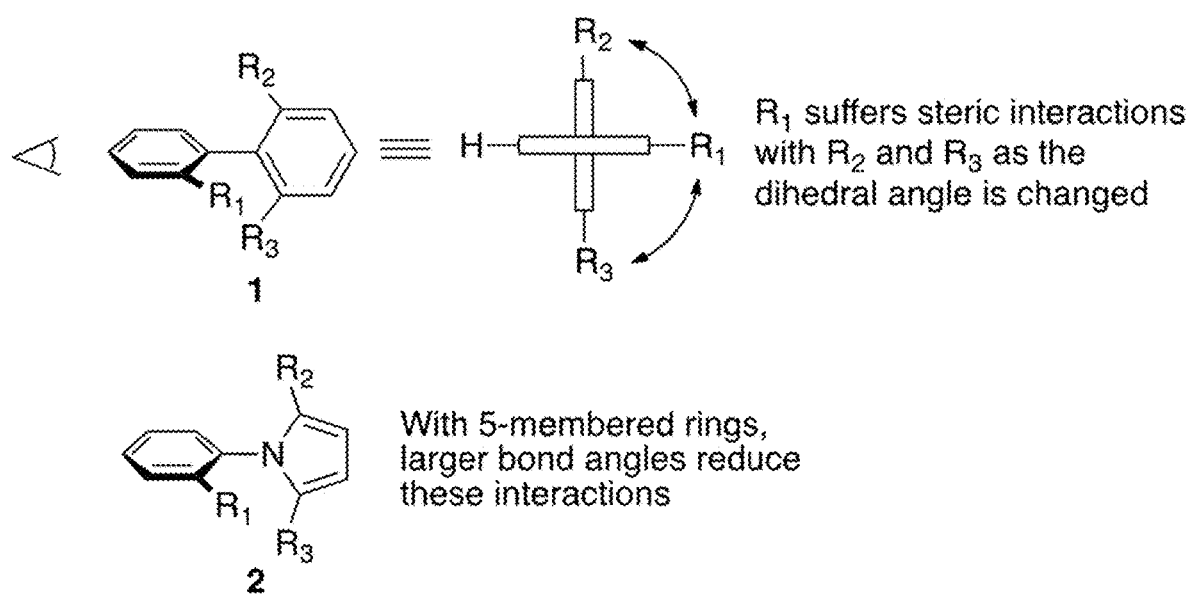
Fig. 1.2

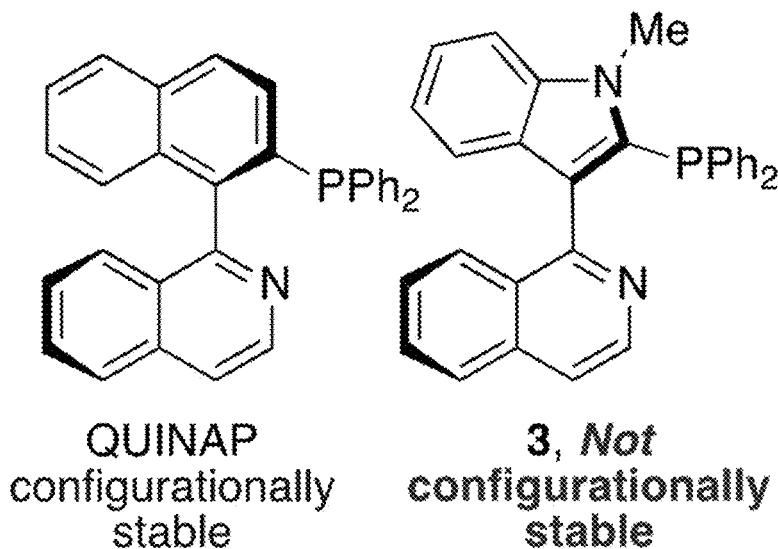
QUINAP
configurationally
stable
3, *Not*
configurationally
stable
*Fig. 1.3*
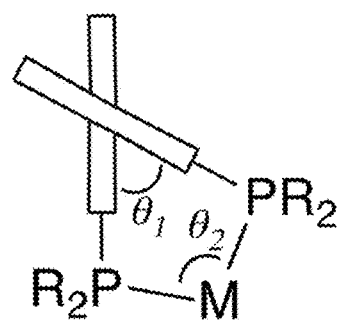
Metal Complex
$\theta_1$ = Dihedral Angle
$\theta_2$ = Bite Angle
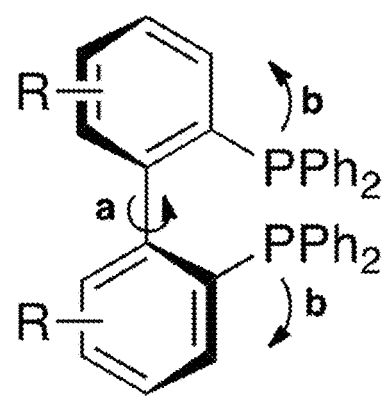
Free Ligand
*Fig. 1.4*

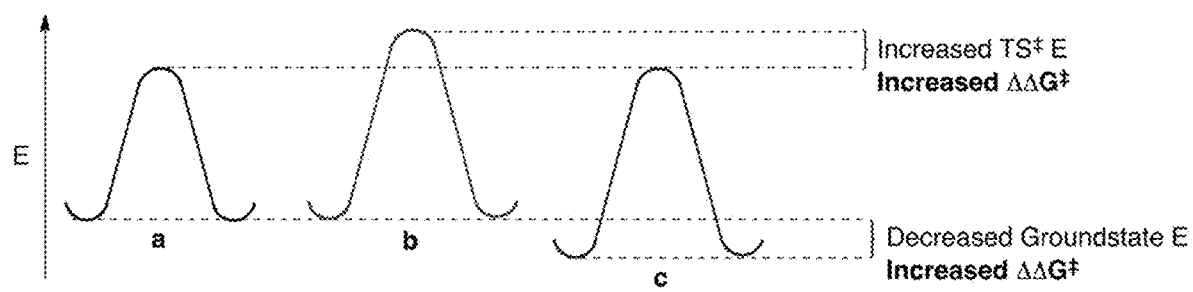
*Fig. 1.5*
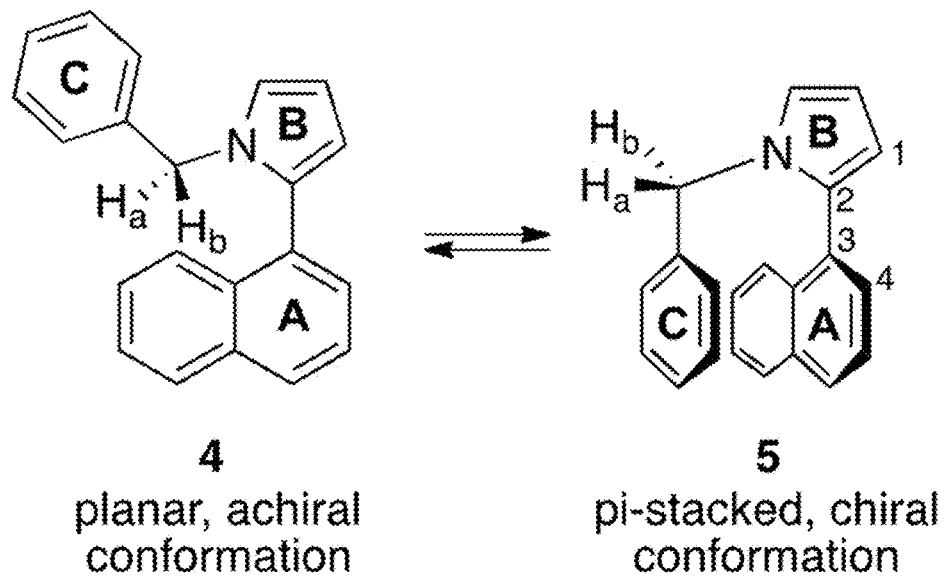
4
planar, achiral
conformation
5
pi-stacked, chiral
conformation
*Fig. 1.6*

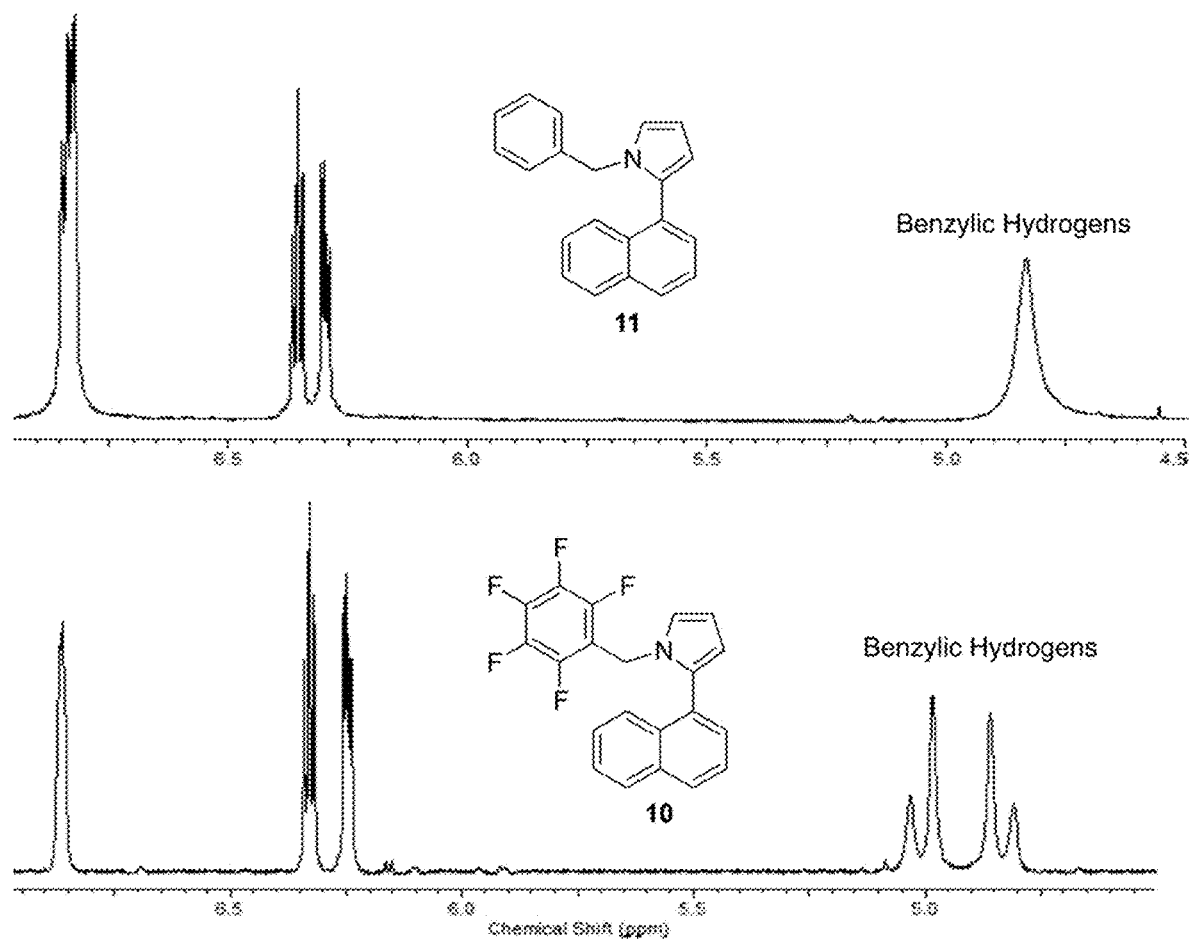
Fig. 1.7

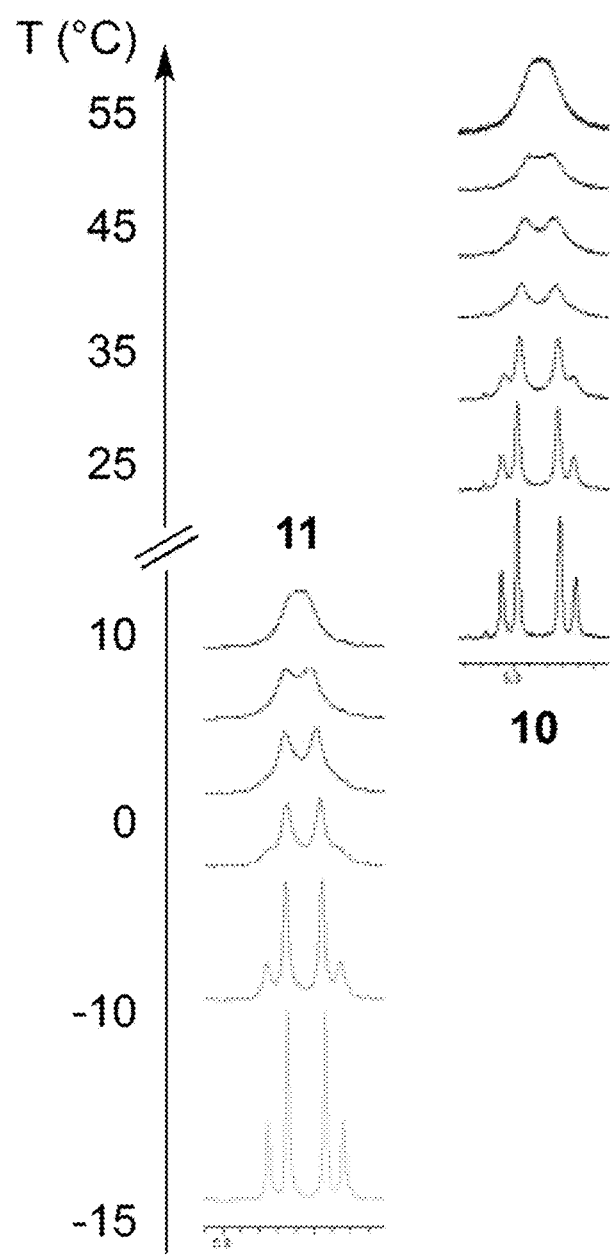
Fig. 1.8

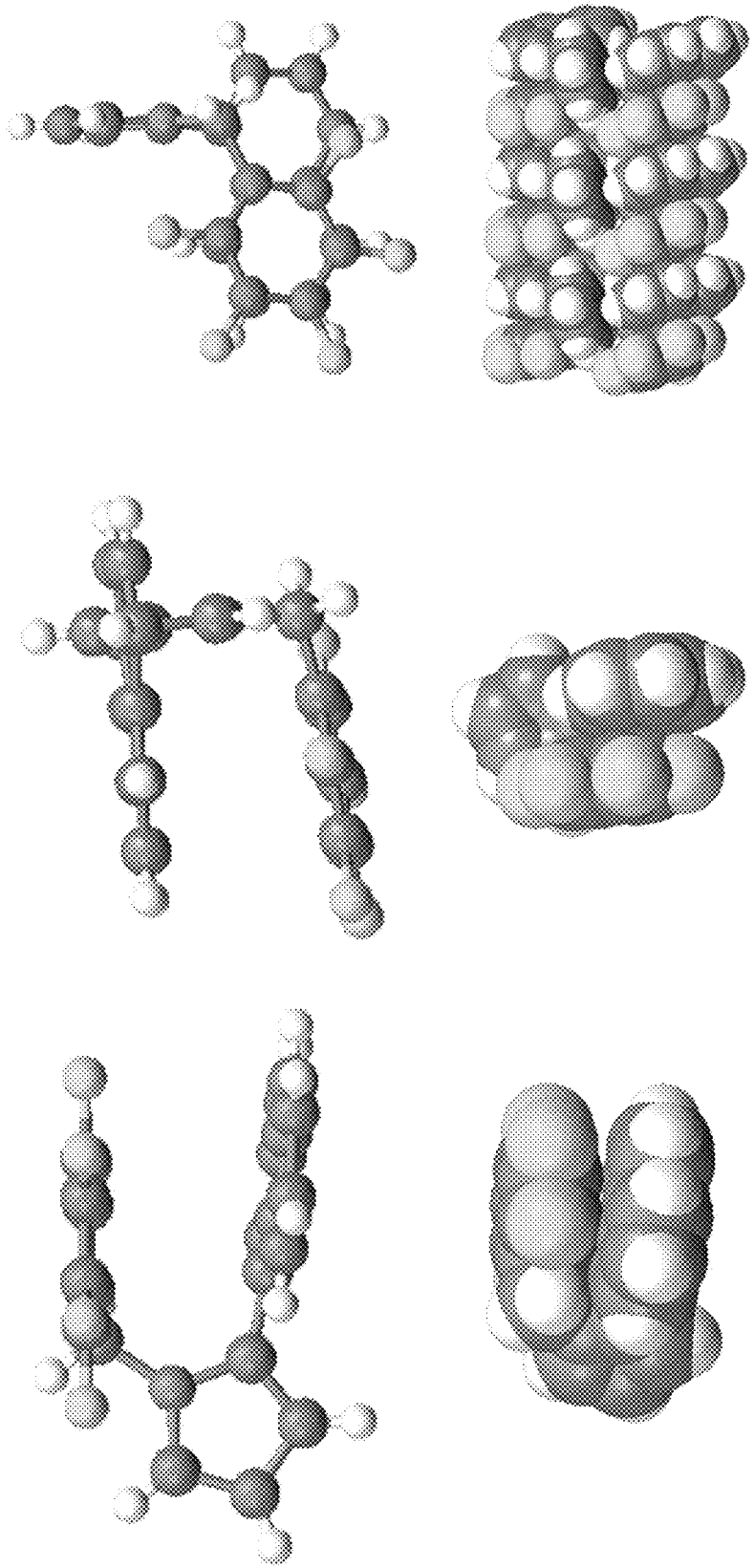
Fig. 1.9

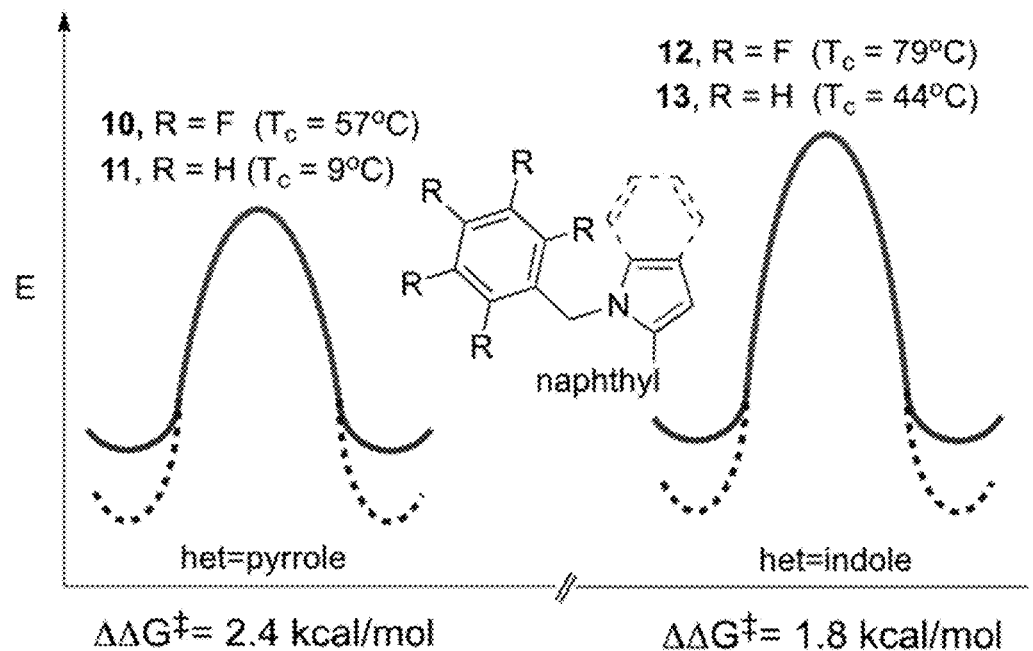
Fig. 1.10
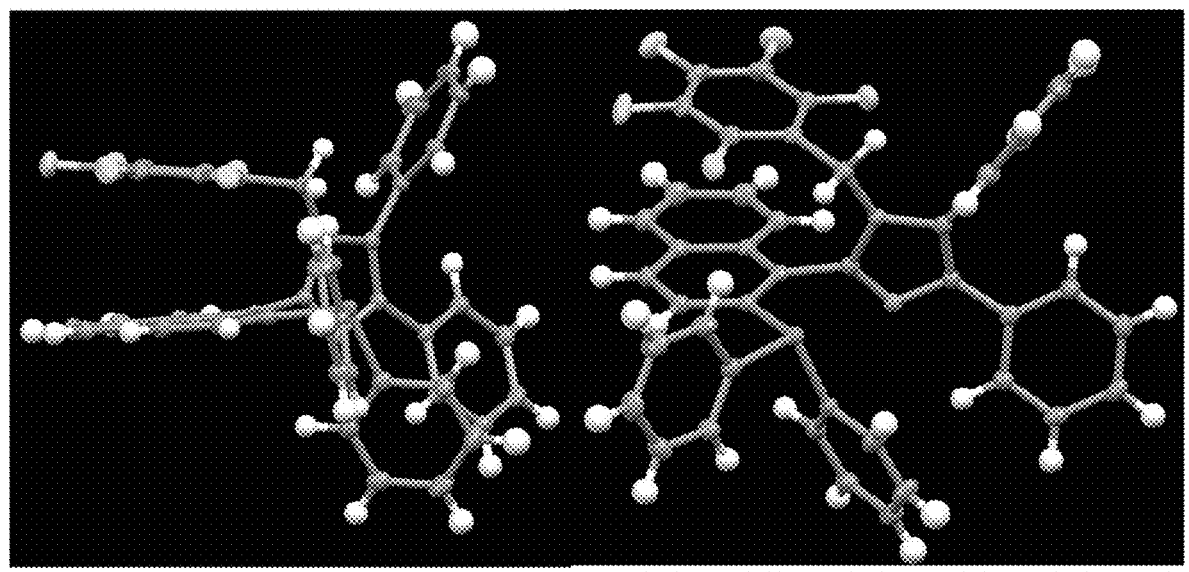
Fig. 1.11

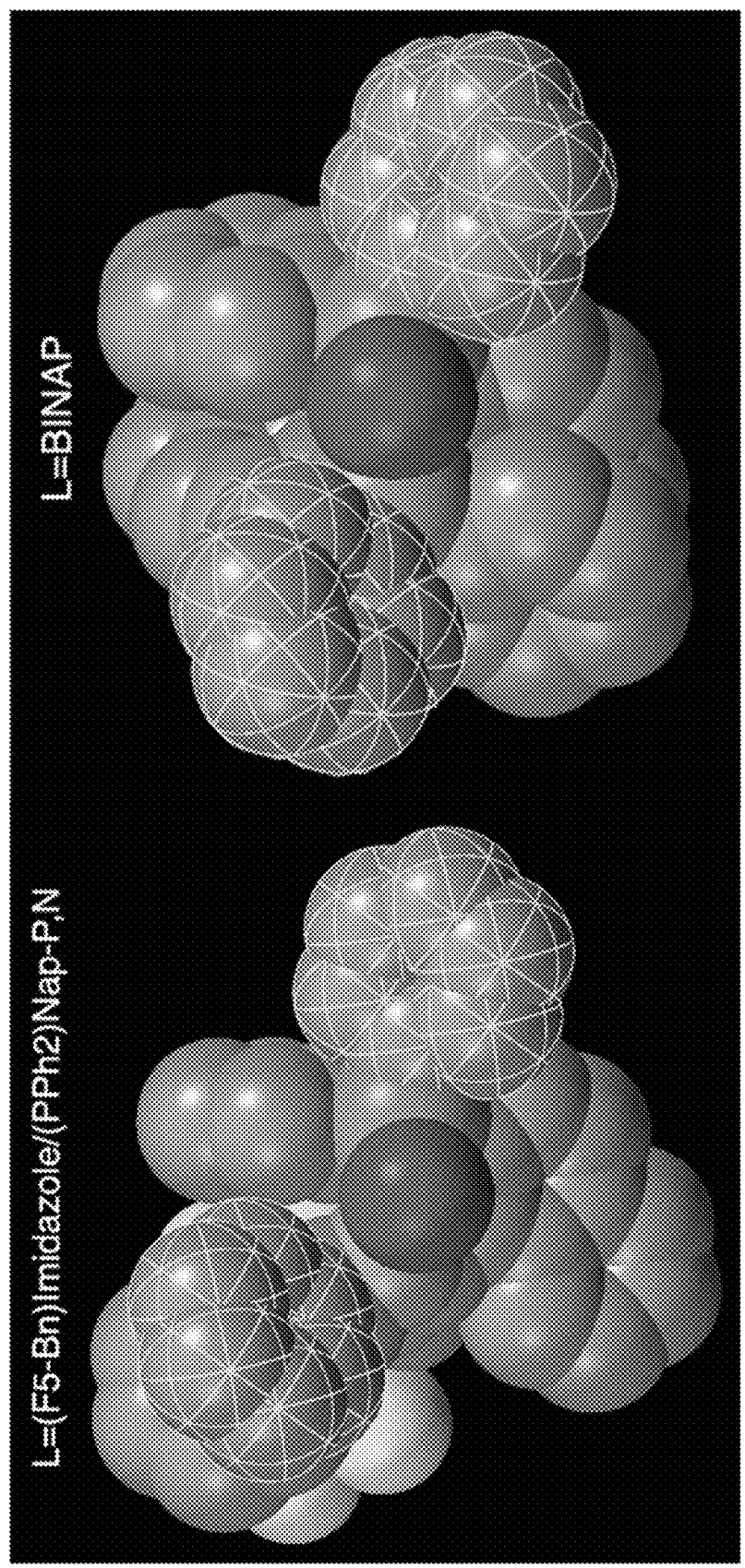
Fig. 1.12

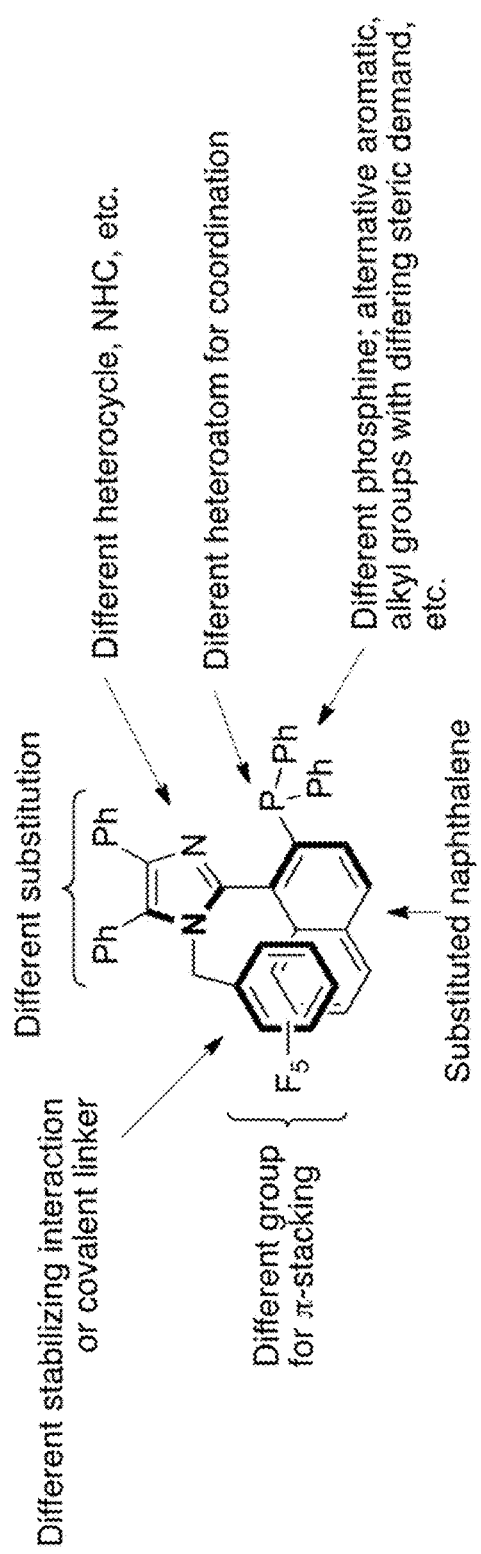
Fig. 1.13
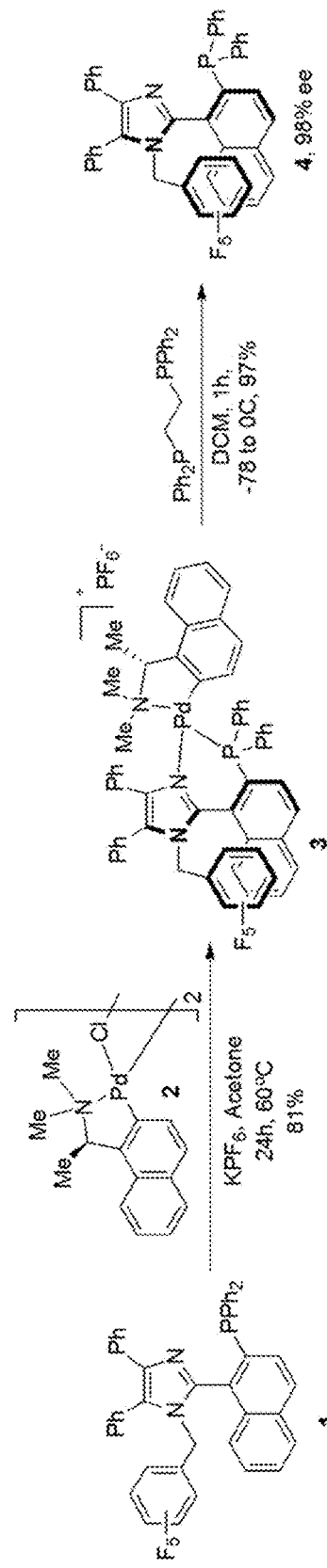
Fig. 2.1

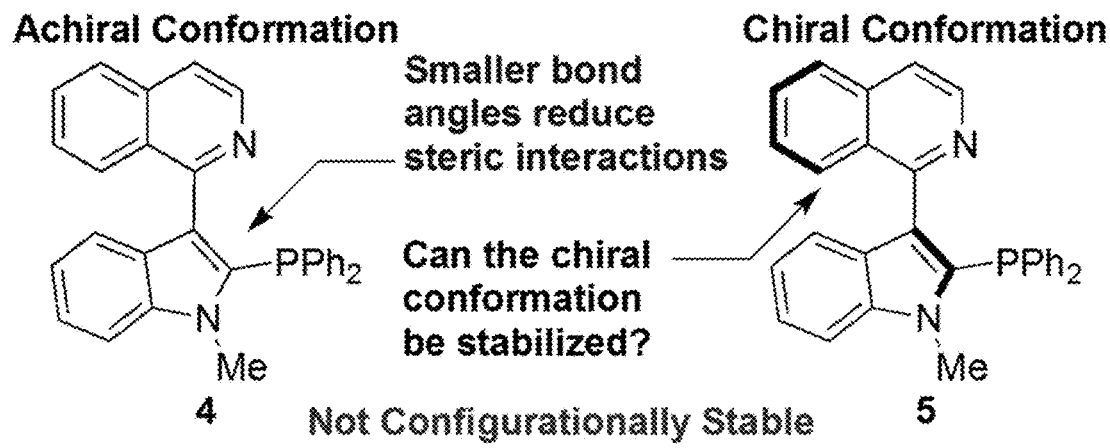
Fig. 3.1
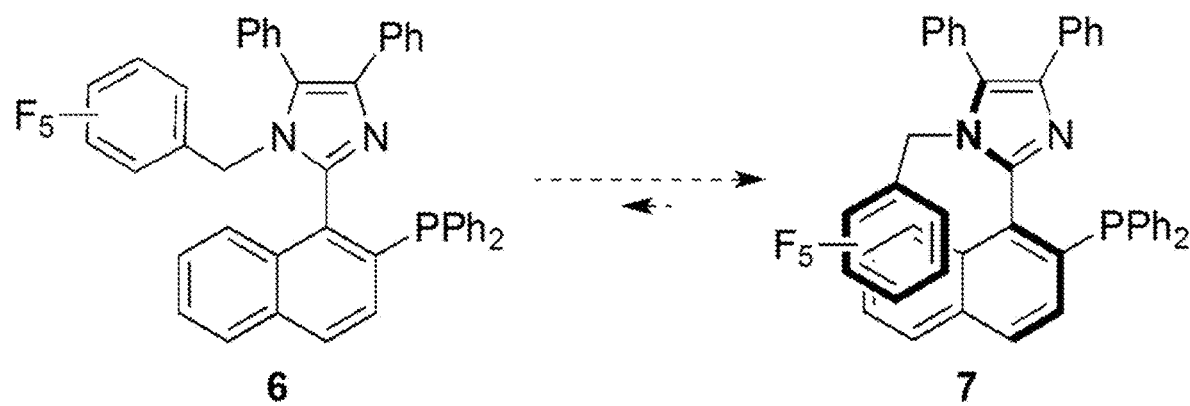
Fig. 3.2

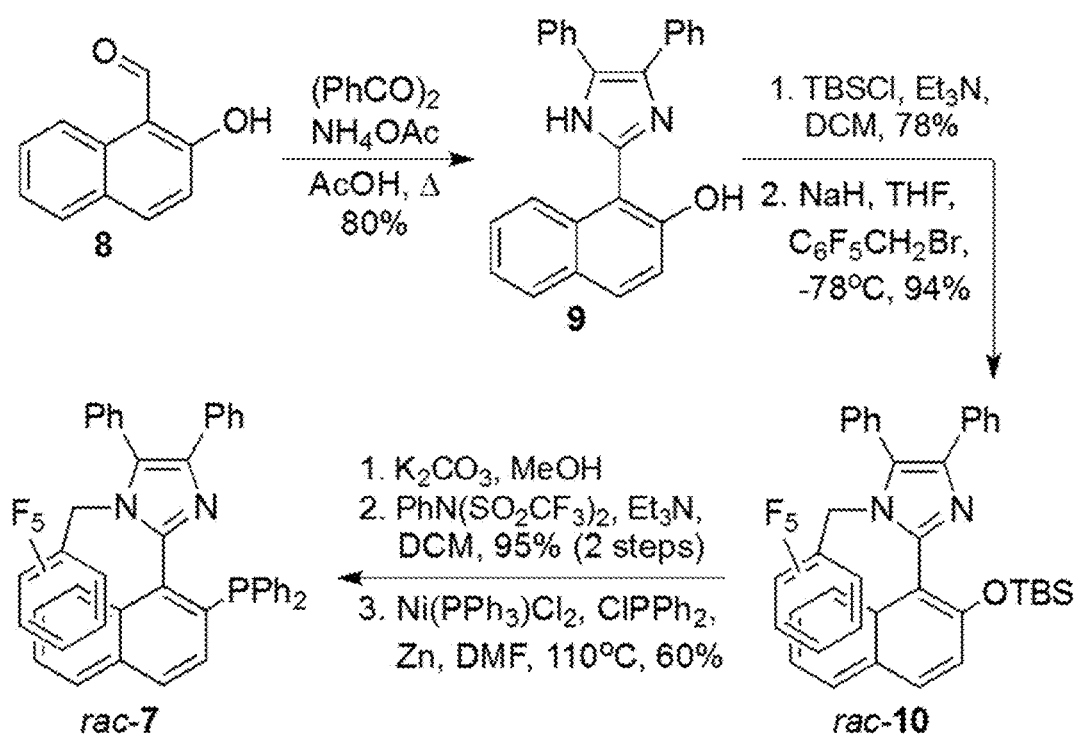
Fig. 3.3

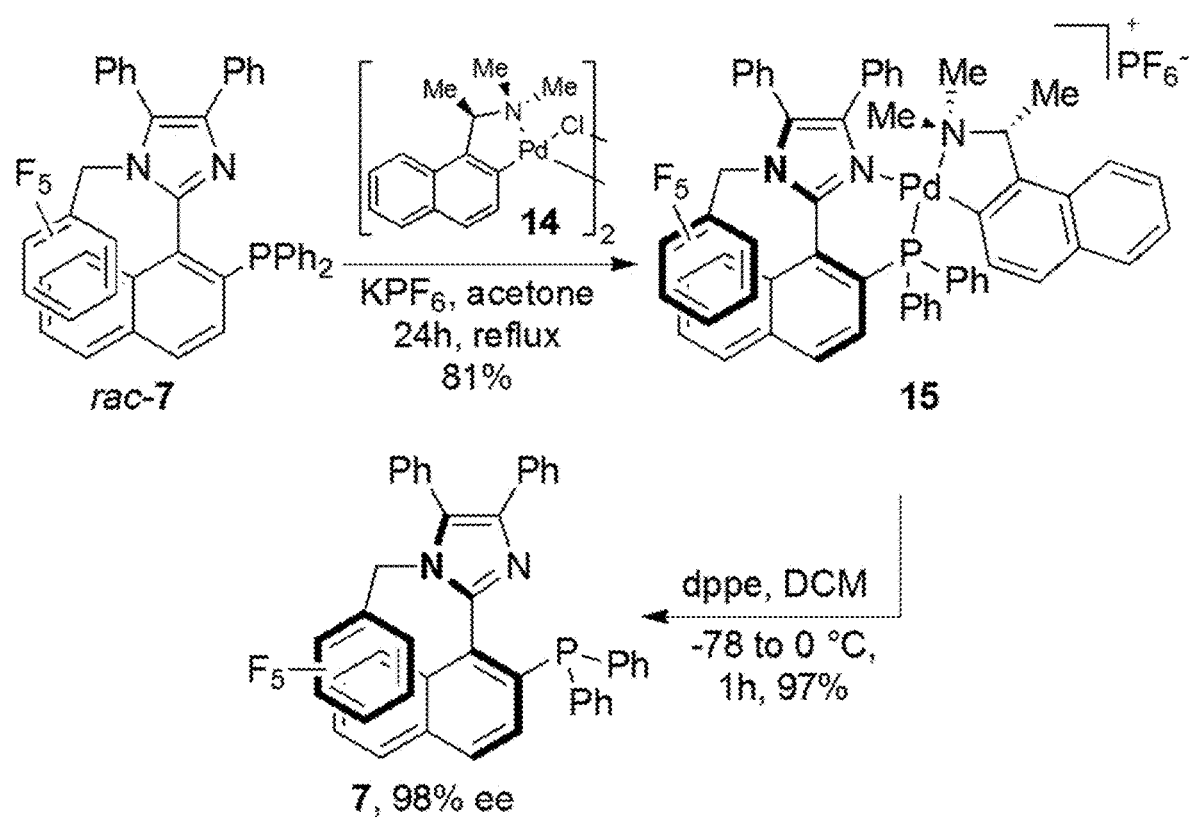
*Fig. 3.4*

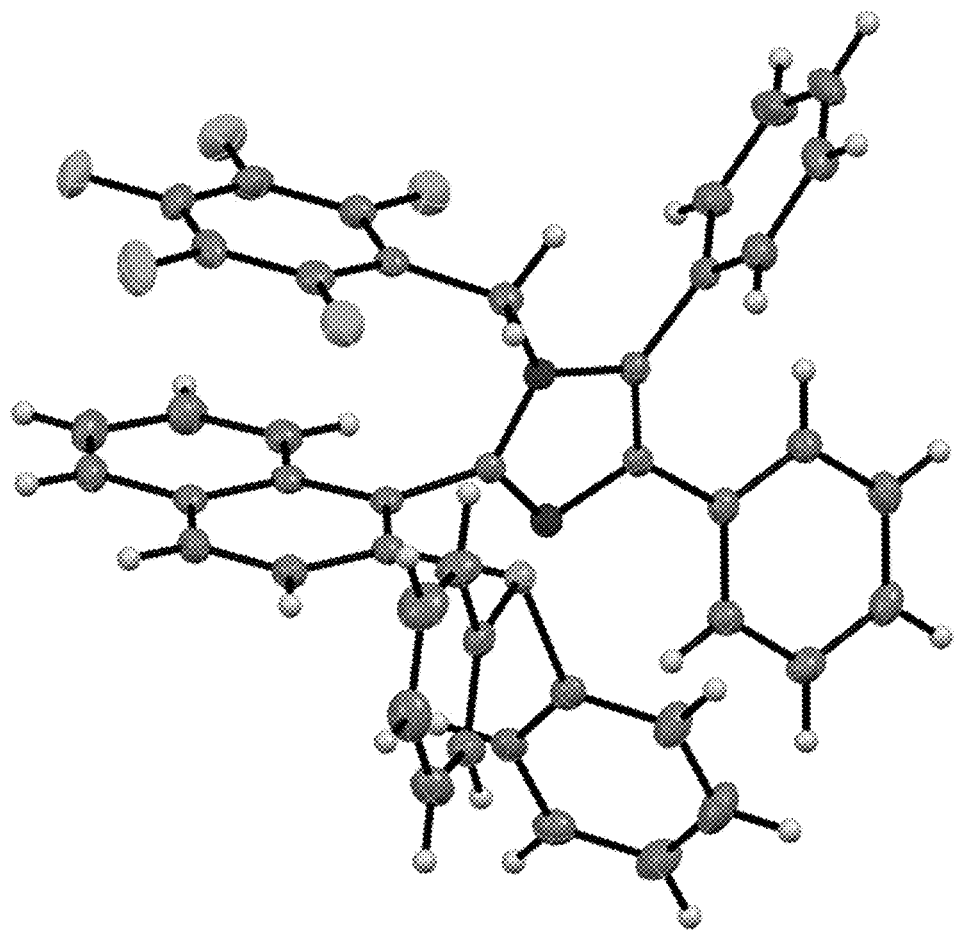
*Fig. 3.5*
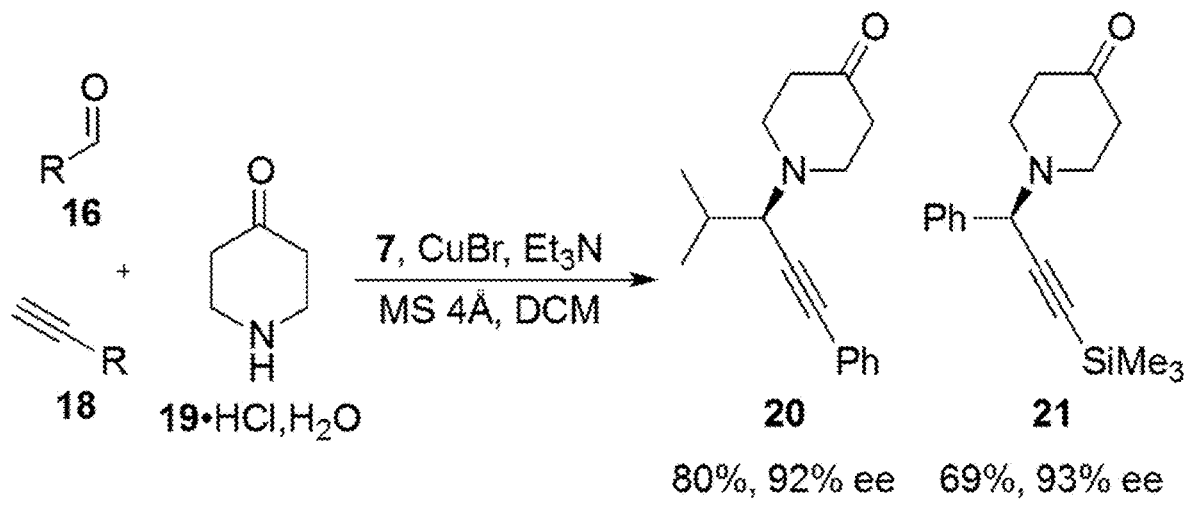
*Fig. 3.6*

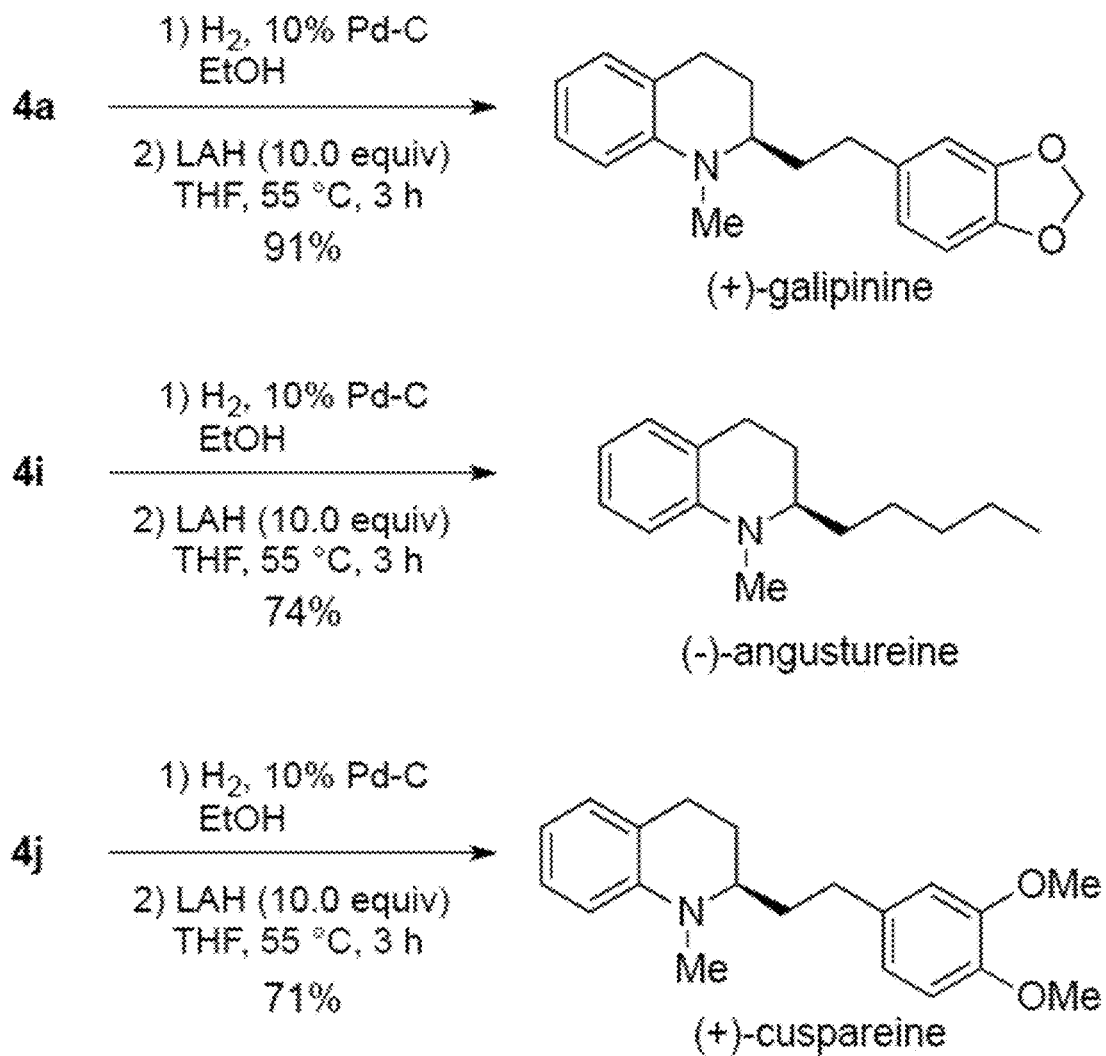
Fig. 4.1

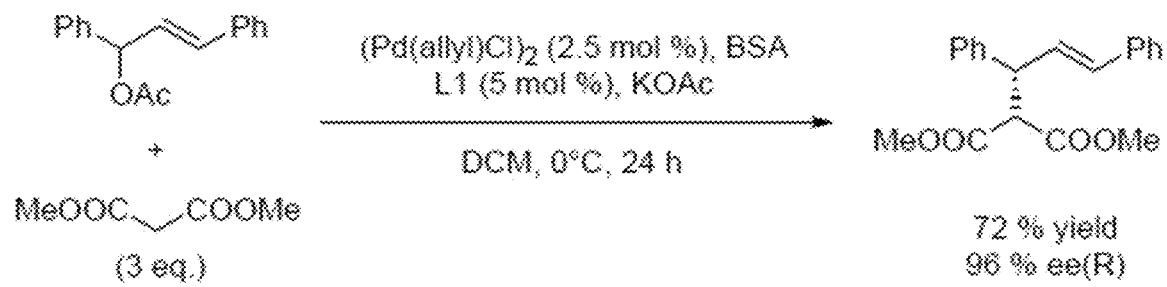
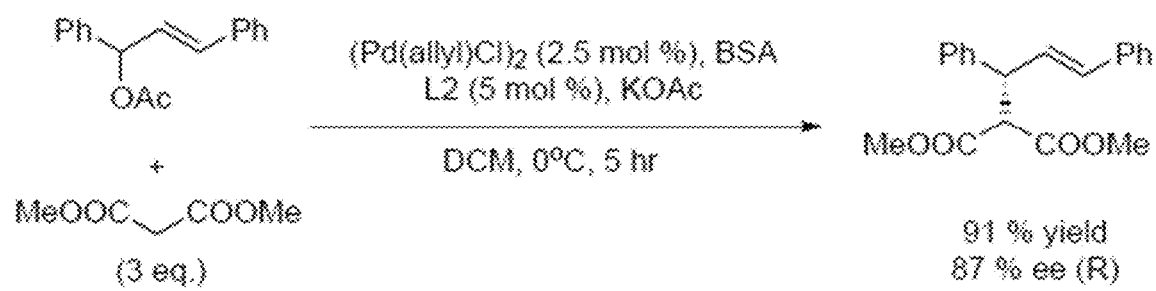
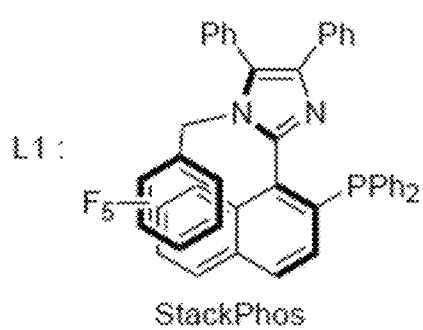
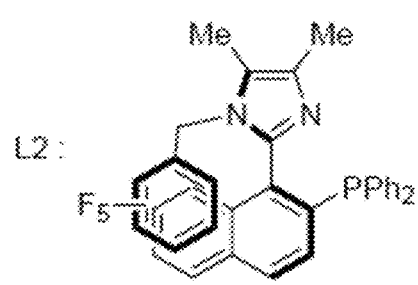
*Fig. 4.2*

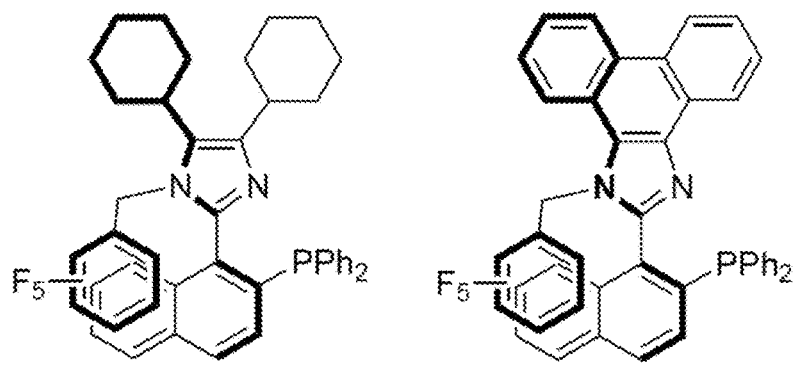
*Fig. 4.3*

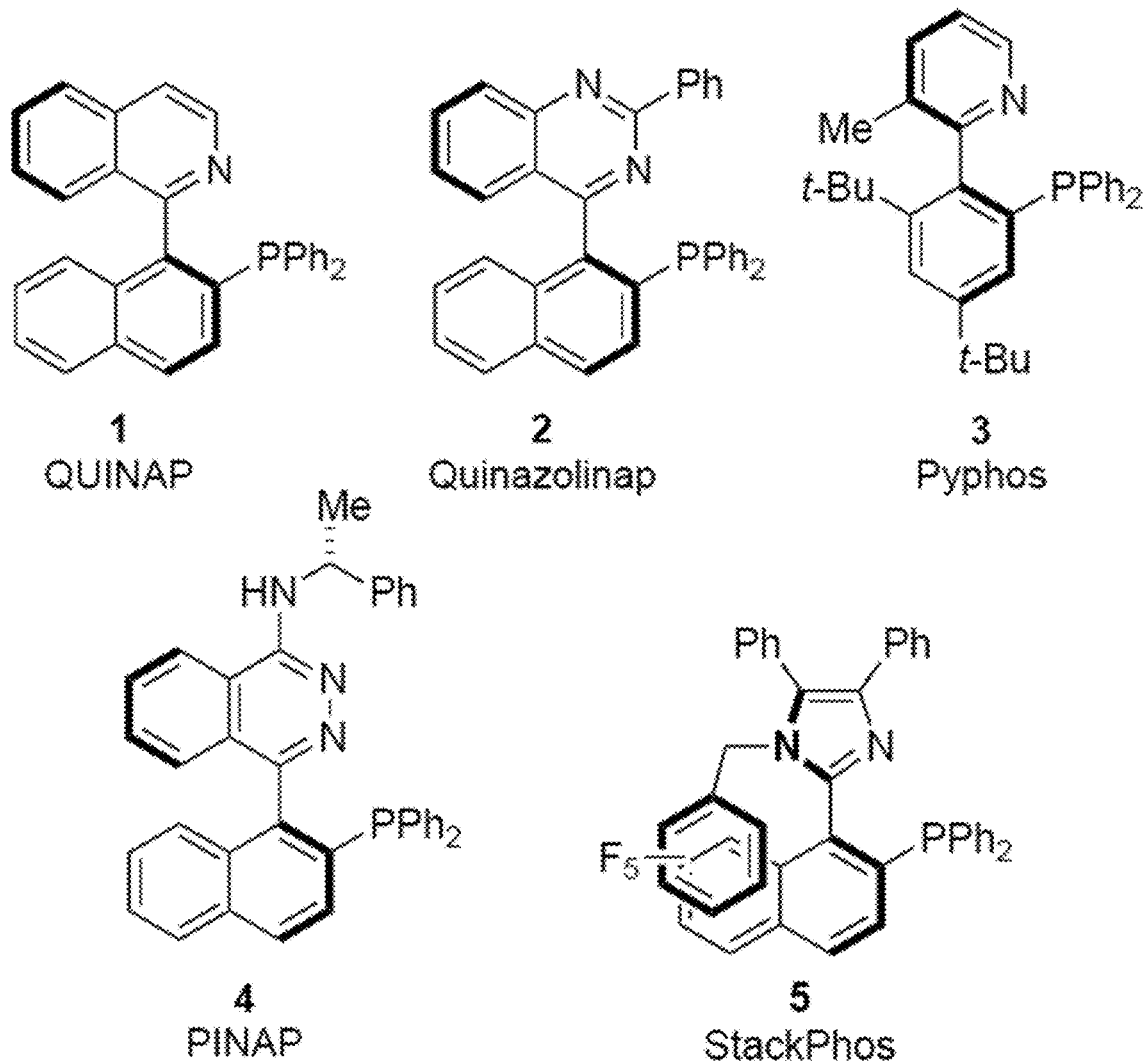
Fig. 5.1

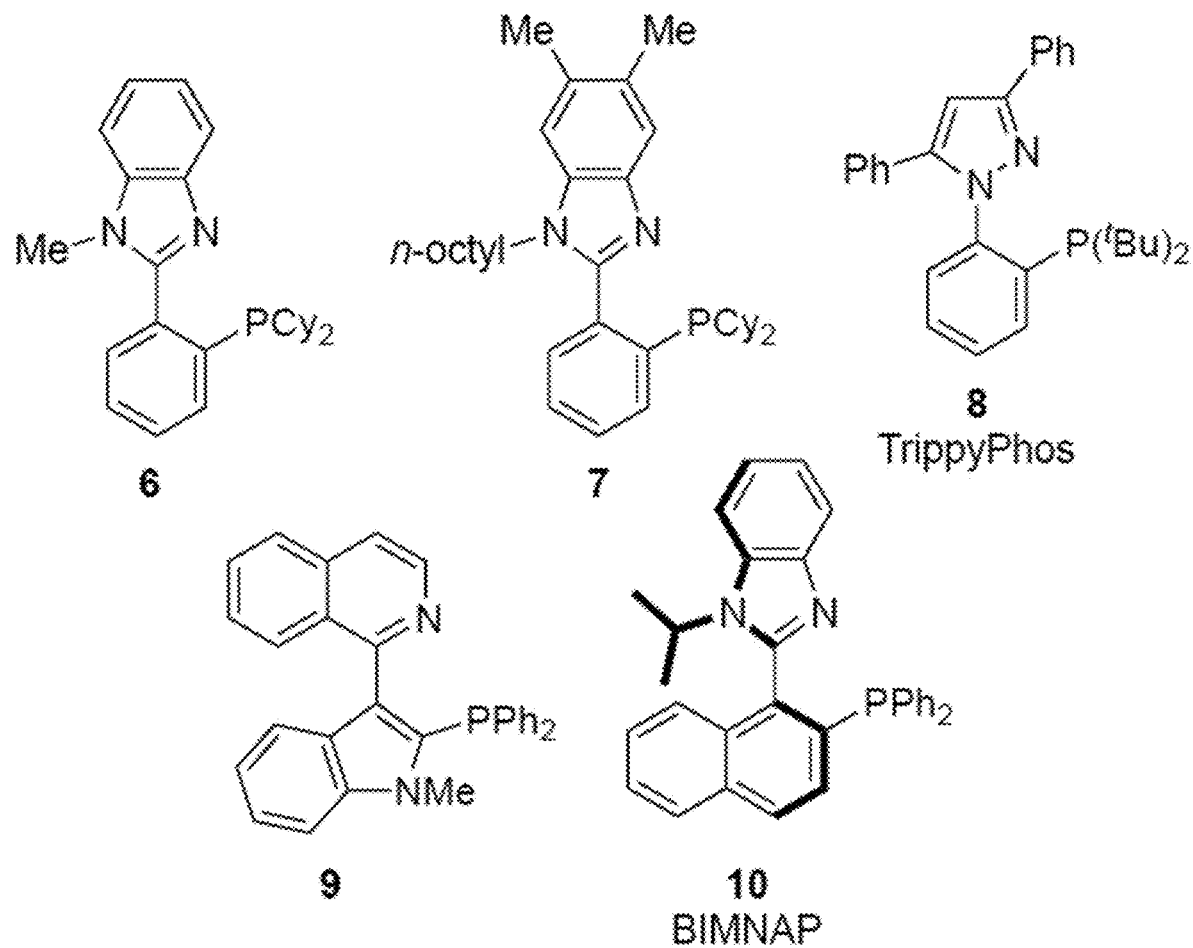
Fig. 5.2

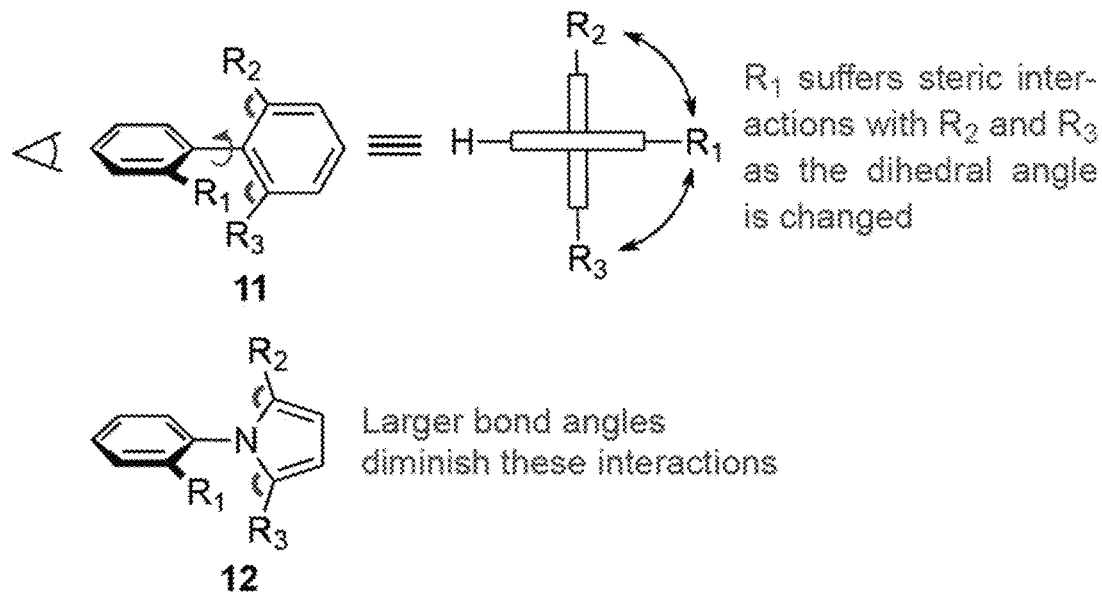
*Fig. 5.3*
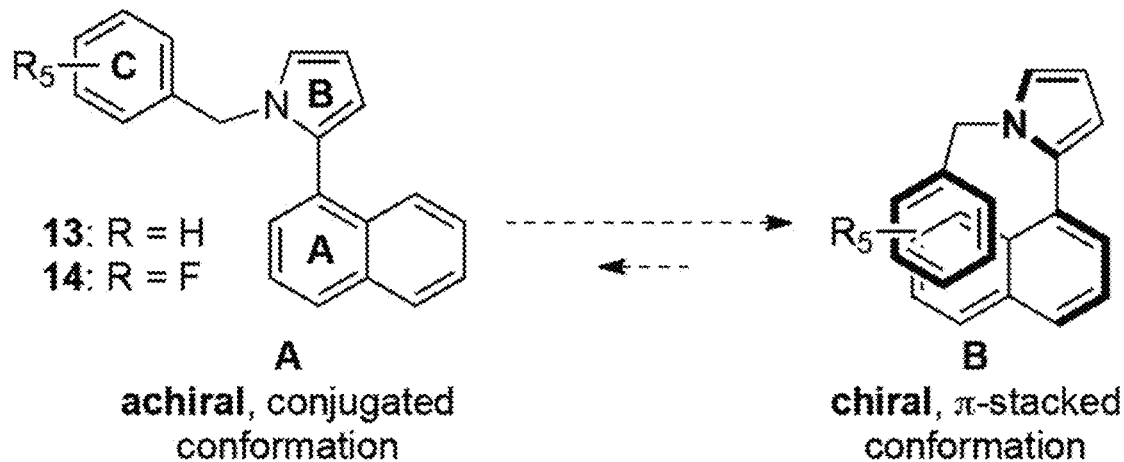
*Fig. 5.4*

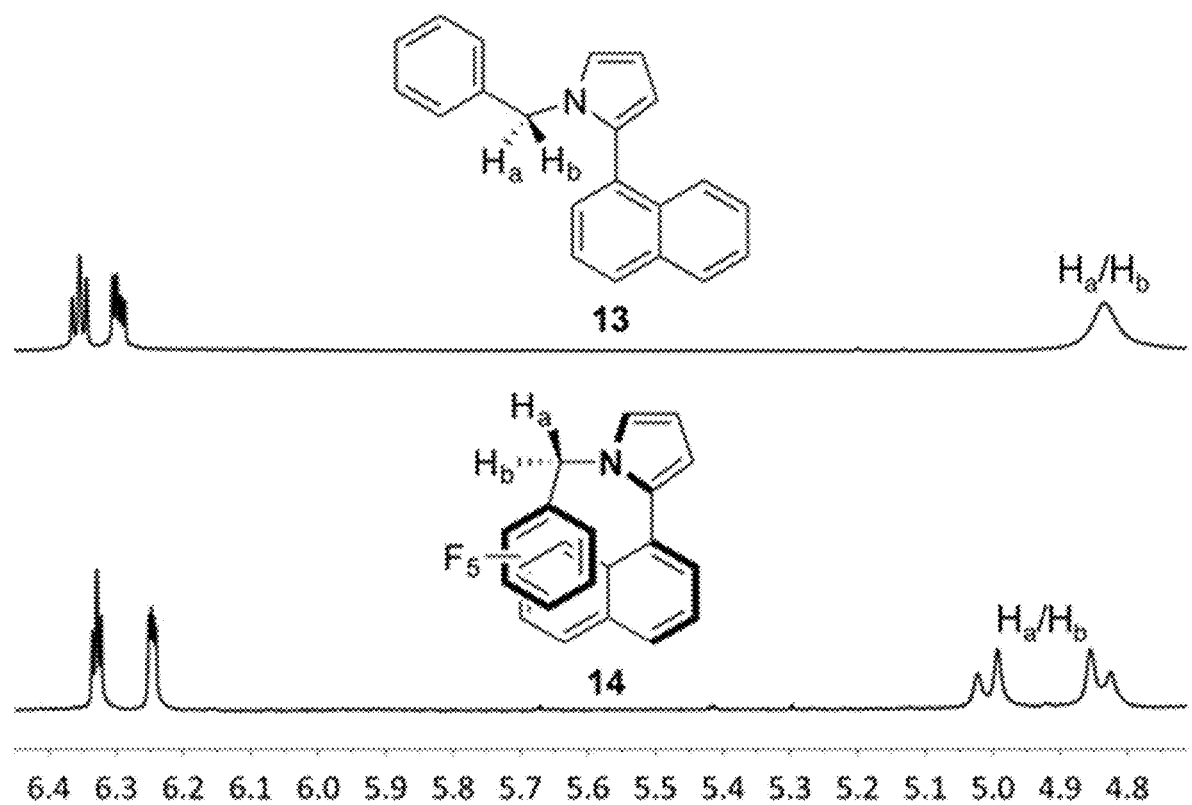
*Fig. 5.5*

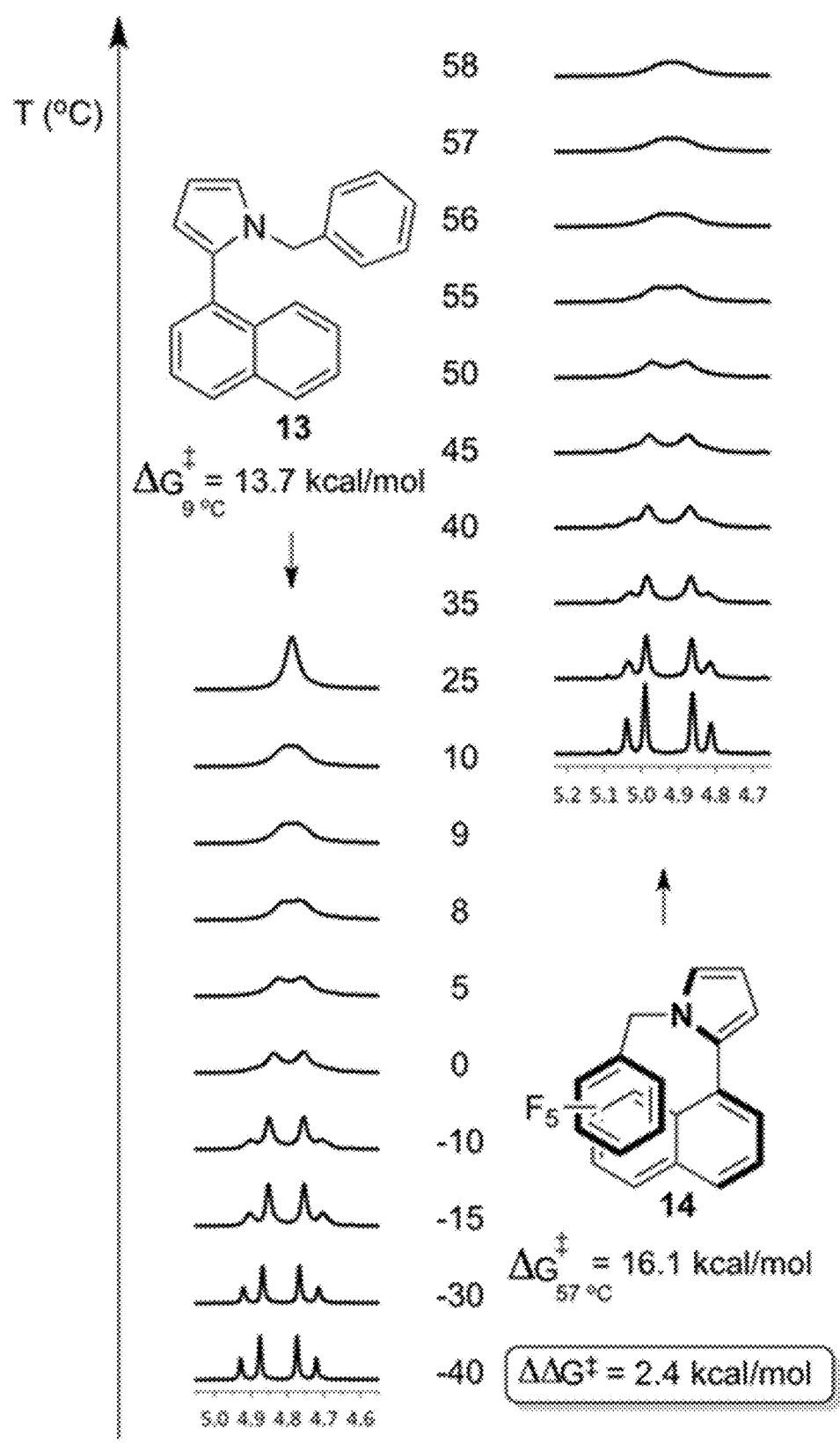
Fig. 5.6

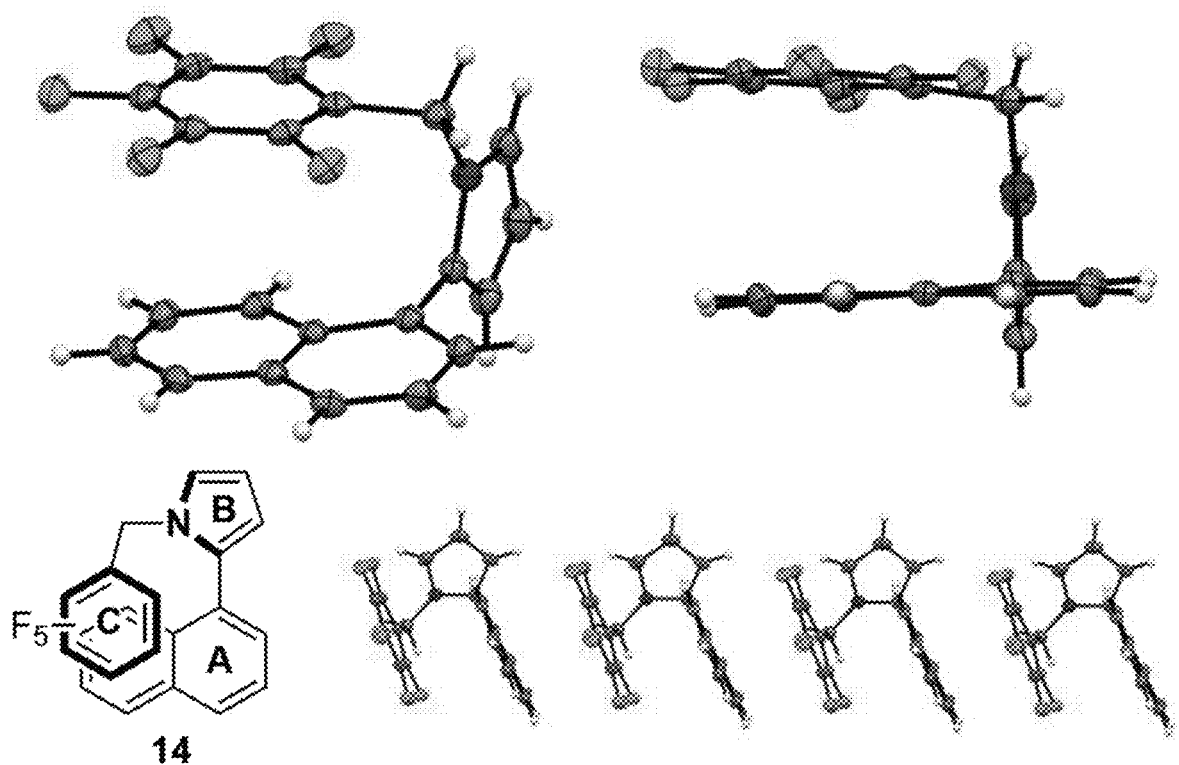
Fig. 5.7

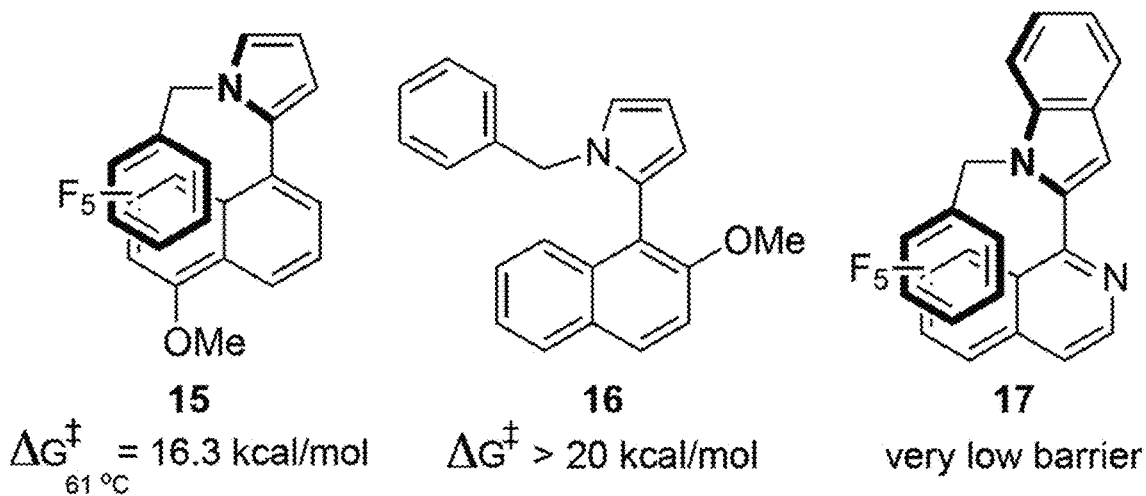
*Fig. 5.8*
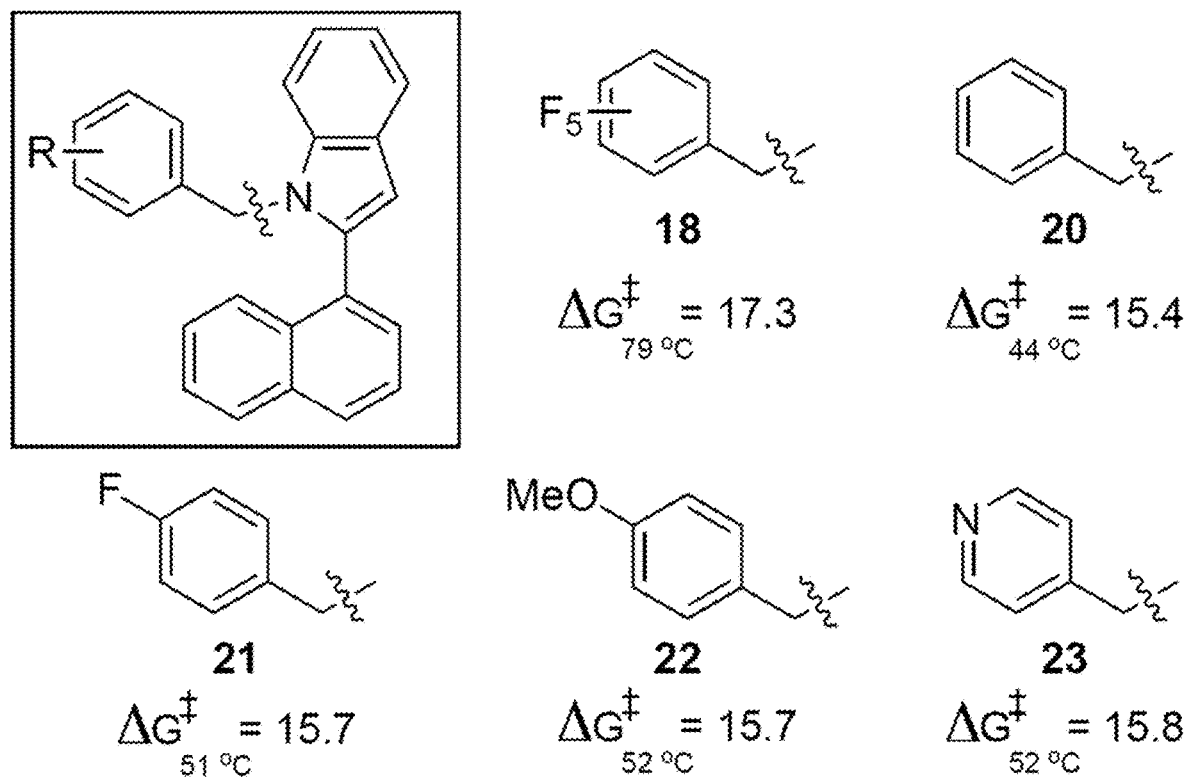
*Fig. 5.9*

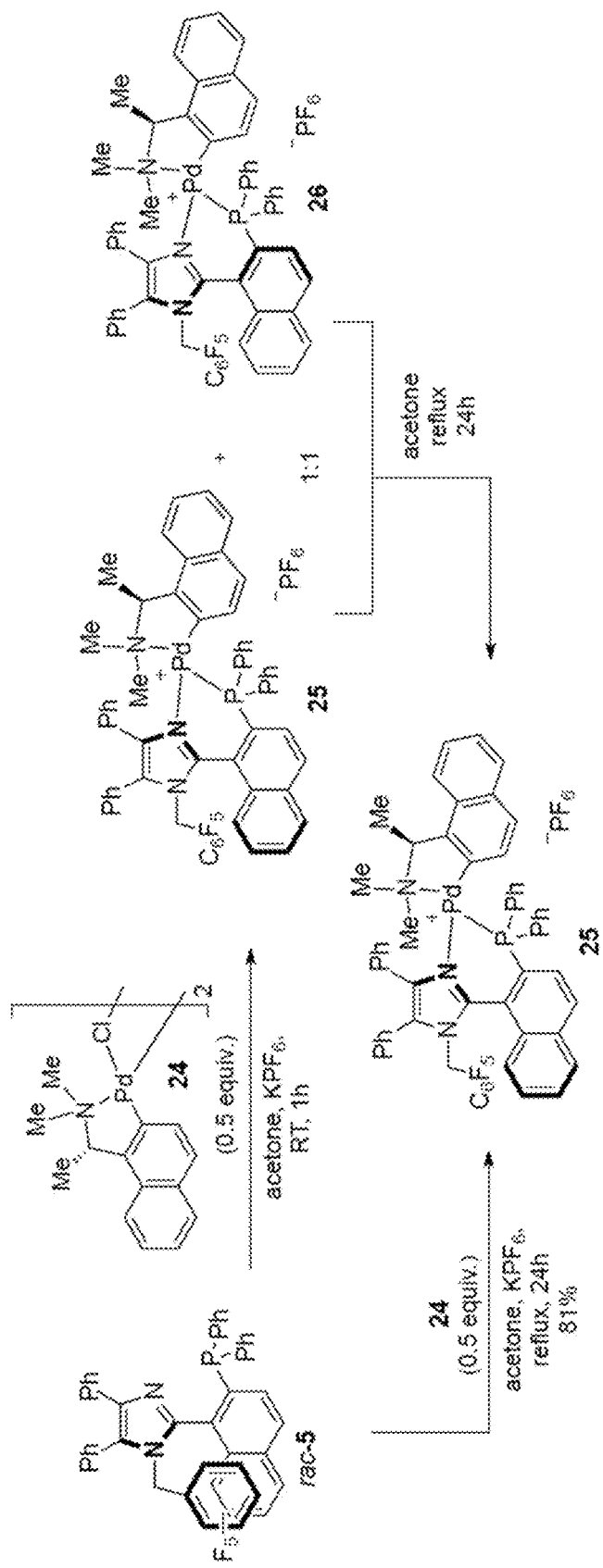
Fig. 5.10

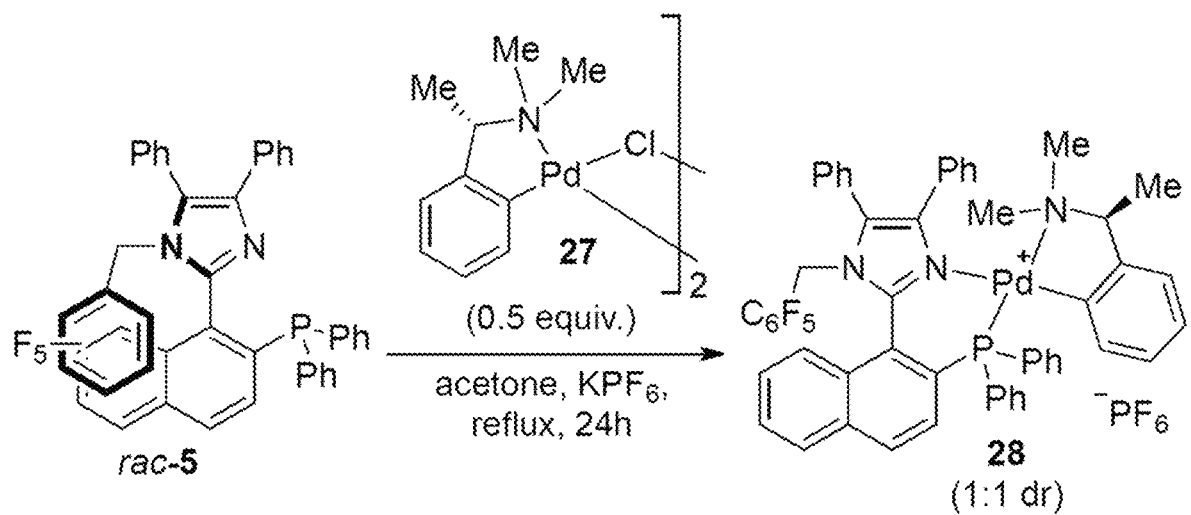
*Fig. 5.11*
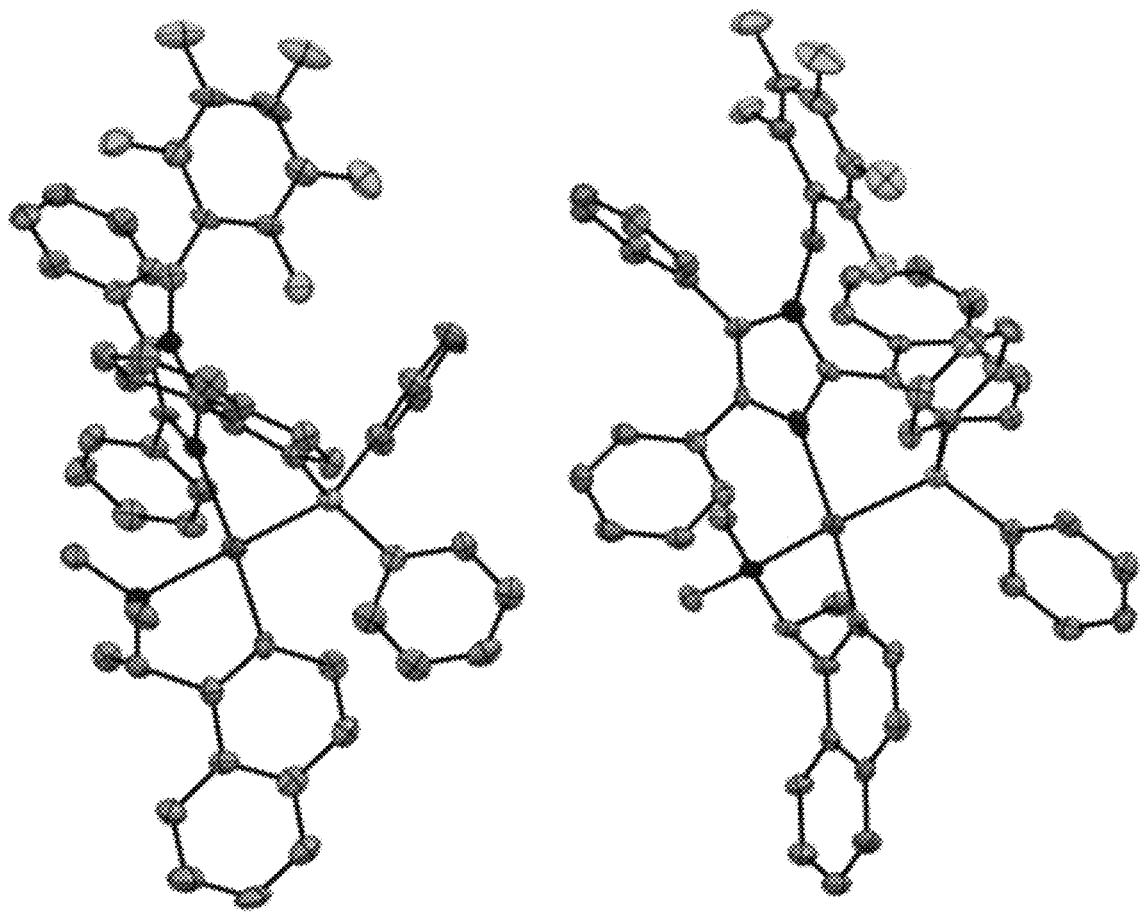
*Fig. 5.12*

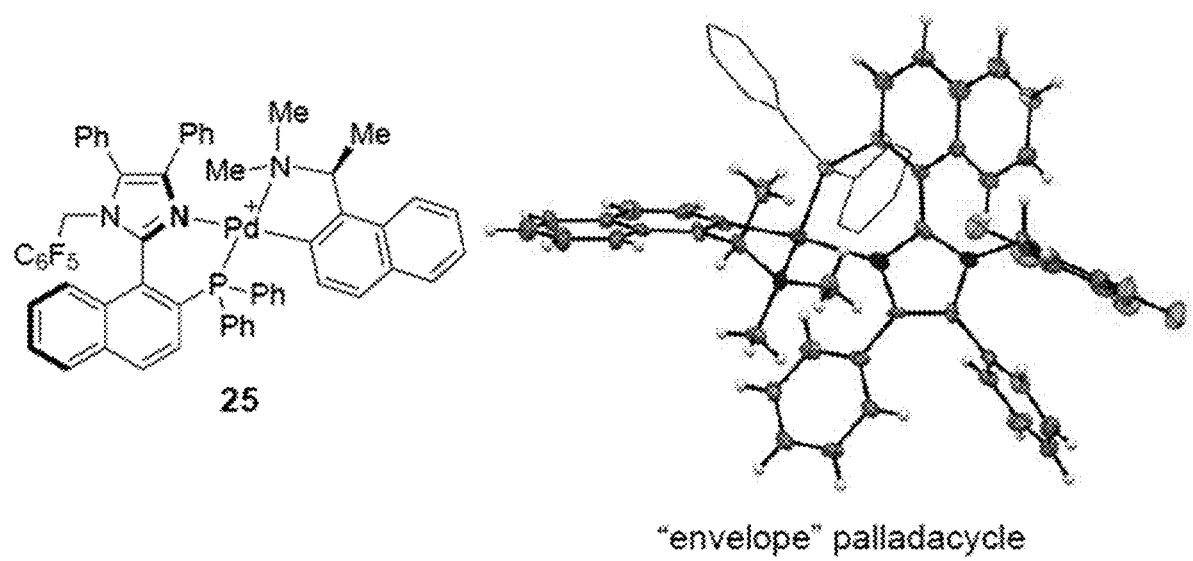
"envelope" palladacycle
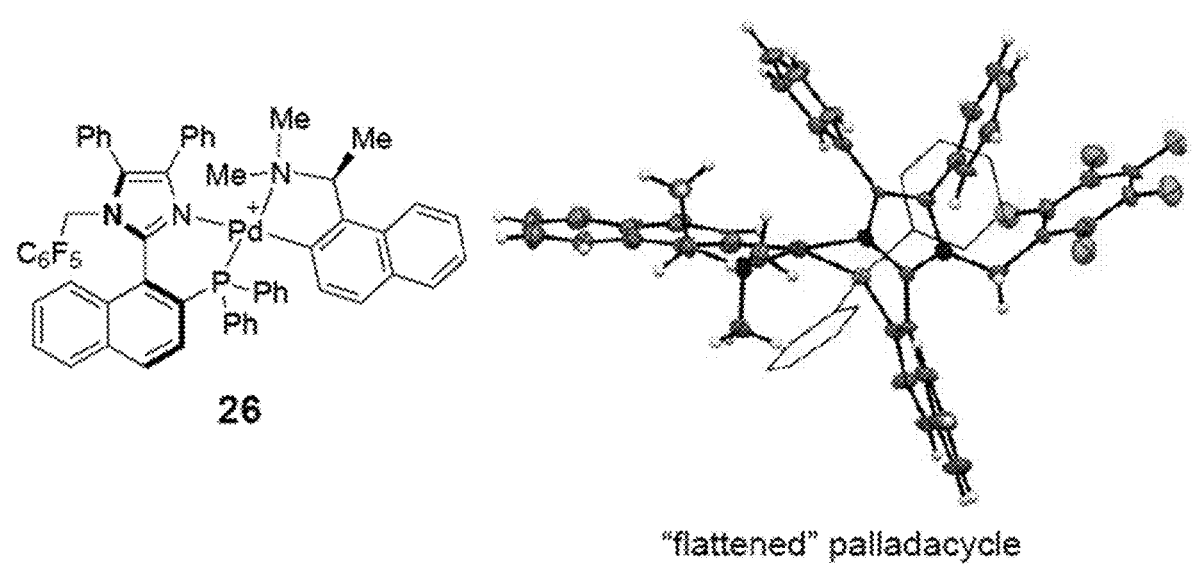
"flattened" palladacycle
*Fig. 5.13*

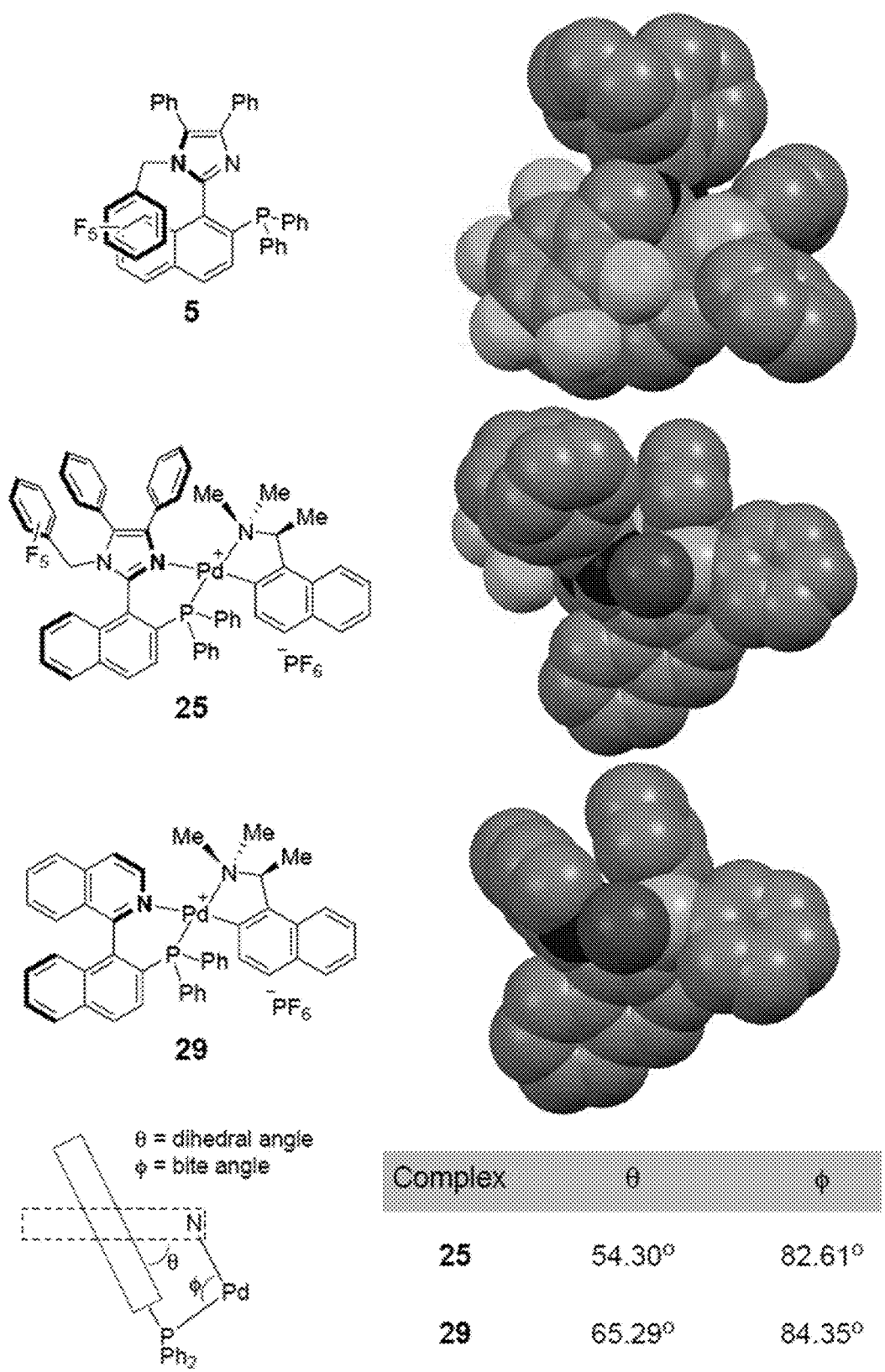
*Fig. 5.14*

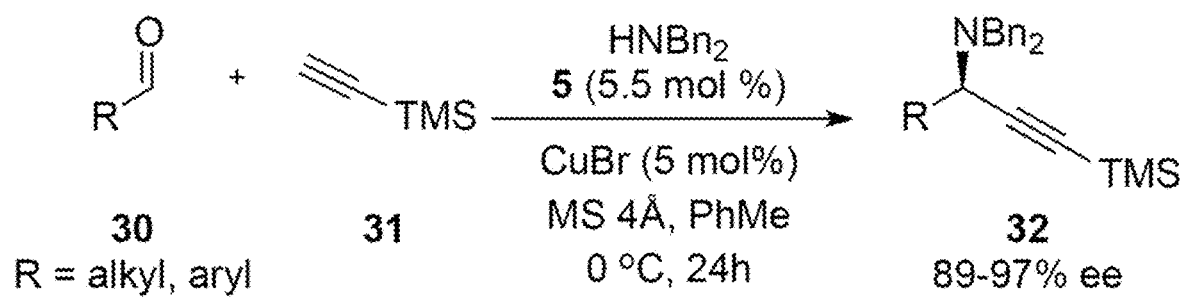
*Fig. 5.15*

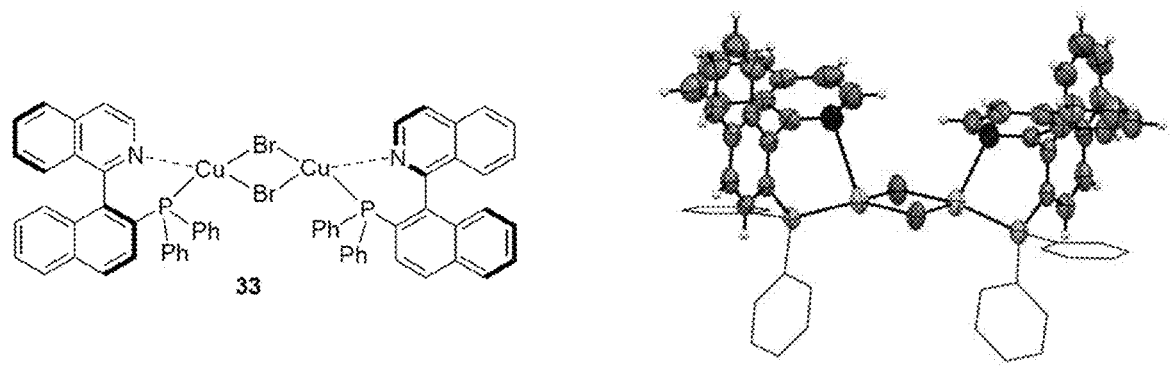
*Fig. 5.16A*
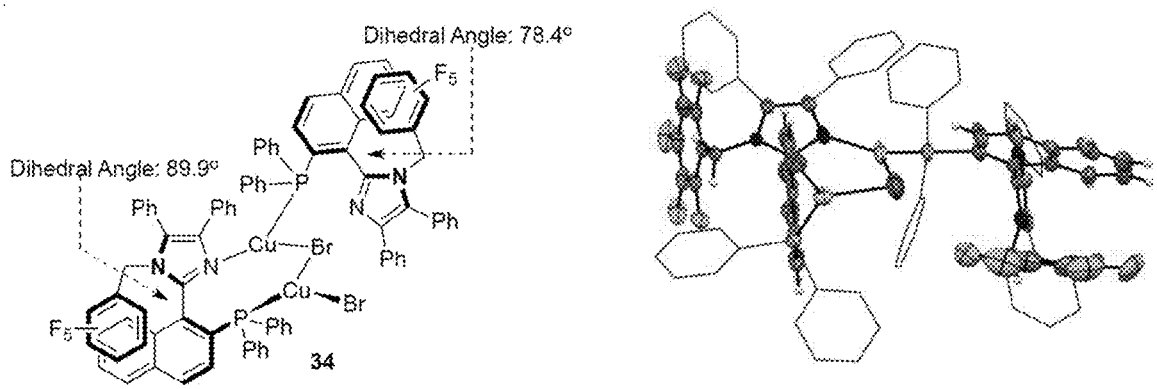
*Fig. 5.16B*
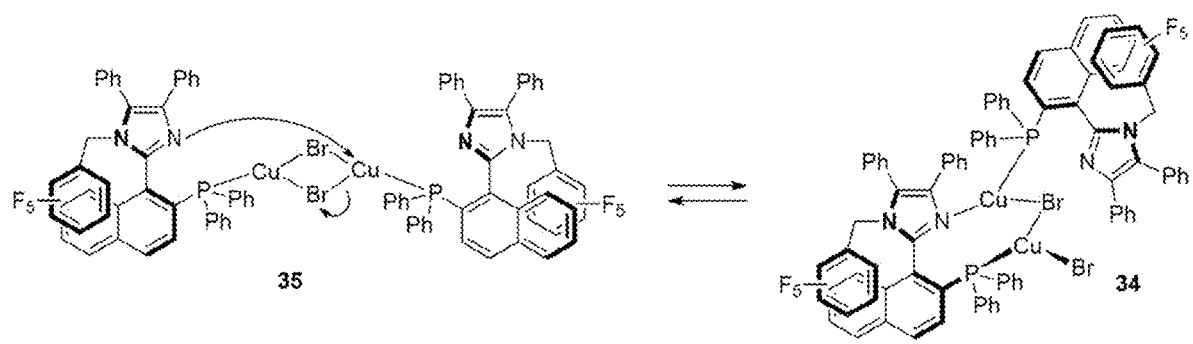
*Fig. 5.16C*

BIARYL LIGANDS, METHODS OF MAKING BIARLYL LIGANDS, AND METHODS OF USE THEREOF

CROSS-REFERENCE TO RELATED APPLICATIONS

This application is a continuation application of U.S. patent application Ser. No. 15/927,505 entitled "BIARYL LIGANDS, METHODS OF MAKING BIARYL LIGANDS, AND METHODS OF USE THEREOF," filed on Mar. 21, 2018, which is a continuation application of U.S. patent application Ser. No. 15/021,053 entitled "BIARYL LIGANDS, METHODS OF MAKING BIARYL LIGANDS, AND METHODS OF USE THEREOF," filed on Mar. 10, 2016 and issued on Jun. 12, 2018 as U.S. Pat. No. 9,994,599.

U.S. patent application Ser. No. 15/021,053 (issued as U.S. Pat. No. 9,994,599) is the 35 U.S.C. § 371 national stage application of PCT Application No. PCT/US2014/055356, filed Sep. 12, 2014. PCT Application No. PCT/US2014/055356 claims priority to U.S. Provisional Patent Application No. 61/877,505 entitled "BIARYL LIGANDS, METHODS OF MAKING BIARYL LIGANDS, AND METHODS OF USE THEREOF," filed on Sep. 13, 2013, and the PCT Application also claims priority to U.S. Provisional Patent Application No. 61/881,480 entitled "BIARYL LIGANDS, METHODS OF MAKING BIARYL LIGANDS, AND METHODS OF USE THEREOF," filed on Sep. 24, 2013.

All of the aforementioned patents or patent applications are entirely incorporated herein by reference.

BACKGROUND

The development of new chiral ligands is essential for enantioselective catalysis and continues to be an important area at the forefront of organic synthesis. Of particular importance are new ligands that introduce fundamental changes in the chiral backbone and/or unique modes of coordination.

SUMMARY

Embodiments of the present disclosure provide for biaryl ligands (also referred to herein as "biaryl compound"), biaryl complexes, methods of making biaryl compounds, methods of making single enantiomers of these biaryl compounds, methods of use (e.g., catalysis), and the like.

One exemplary composition, among others, includes: a single biaryl enantiomer of the following structure:

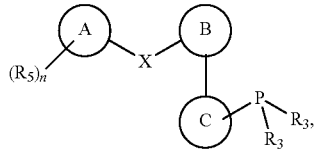

wherein the A ring is selected from a benzenoid, a 5 or 6-membered heteroaromatic ring, or an aryl or heteroaryl fused-ring, system, wherein each of the $R_5$ groups is independently selected from: hydrogen, a halogen group, a cyclic or linear, alkyl group, an aryl group, a —OR group, a —SR group, a —SiR$_3$ group, a NR$_2$ cyclic or linear group, wherein R is selected from: hydrogen, a cyclic or linear, alkyl group, or an aryl group, wherein n is 1 to 5, wherein X is CR$_2$ or SO$_2$; wherein the B ring is selected from a 5-member or fused-ring heteroaromatic system; and wherein the C ring is selected from a benzenoid, a 5 or 6-membered heteroaromatic ring, or an aryl or heteroaryl fused-ring, system, wherein each of the $R_3$ groups is independently selected from: hydrogen, a cyclic or linear, alkyl group, an alkoxide, a phenoxide, an aryl group, or a substituted amine, wherein each R group is independently selected.

One exemplary composition, among others, includes: a single biaryl enantiomer of the following structure:

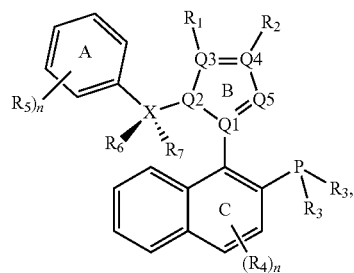

wherein each $R_6$ and $R_7$ group is independently selected from: hydrogen, a cyclic or linear, alkyl group, an aryl group, wherein when X is SO$_2$, $R_6$ and $R_7$ are not present; wherein each Q1, Q2, Q3, Q4, and Q5 are independently selected from C, N, O, or S, wherein one of Q1, Q2, Q3, Q4, and Q5 is selected from N, O, or S, and the other of Q1, Q2, Q3, Q4, and Q5 are selected from C, N, O, or S, wherein $R_1$ and $R_2$ are independently selected from: hydrogen, a halogen group, a cyclic or linear, alkyl group, an aryl group, a —OR group, a —SR group, a —SiR$_3$ group, a NR$_2$ cyclic or linear group, wherein R is selected from: hydrogen, a cyclic or linear, alkyl group, or an aryl group; and wherein each of the $R_4$ groups is selected from: hydrogen, a halogen group, a cyclic or linear, alkyl group, an aryl group, a —OR group, a —SR group, a —SiR$_3$ group, a NR$_2$ cyclic or linear group, wherein R is selected from: hydrogen, a cyclic or linear, alkyl group, alkoxides, phenoxides, aryl groups, or substituted amines, wherein m is 1 to 5.

One exemplary composition, among others, includes: a single biaryl enantiomer of the following structure:

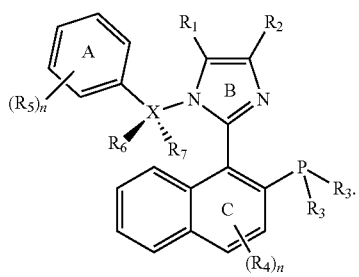

One exemplary method of making a biaryl compound, among others, includes:

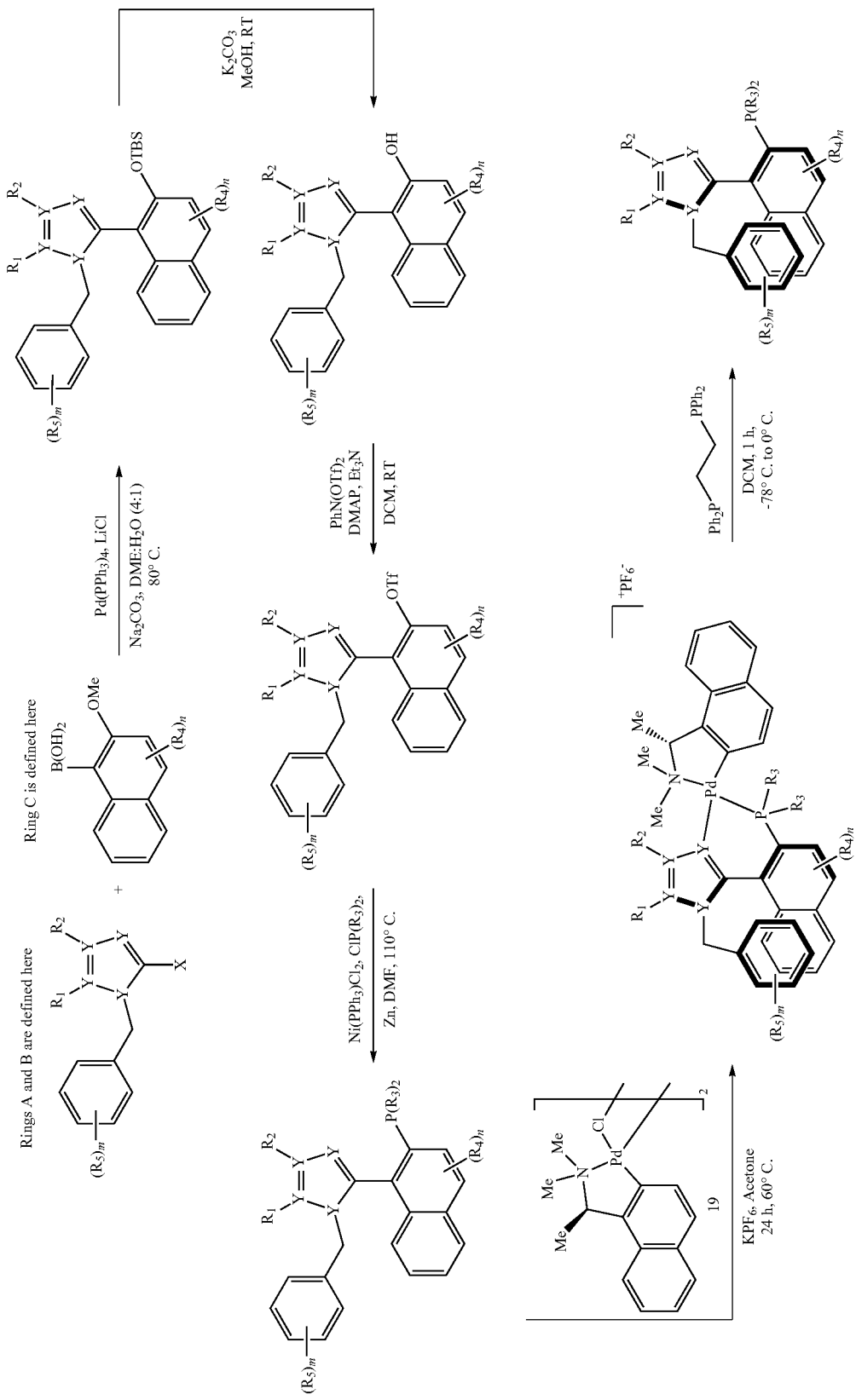

wherein the biaryl product has the following structure:

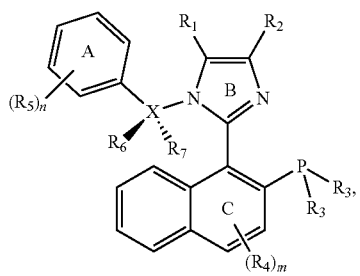

as described herein.

One exemplary method of forming a compound, among others, includes:

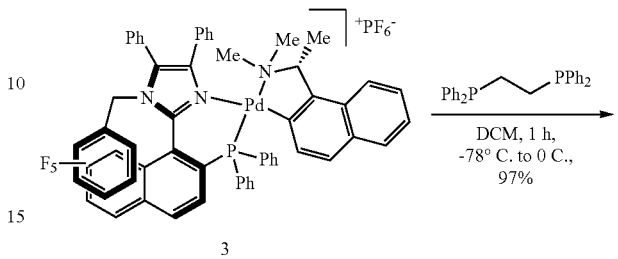

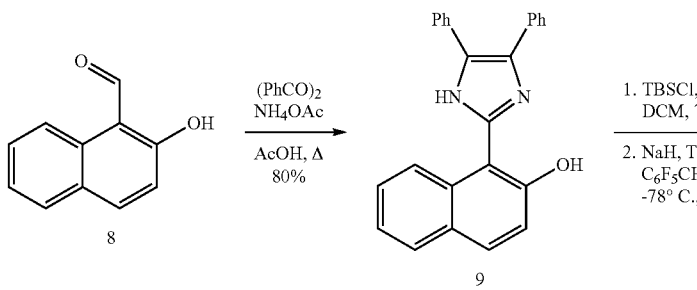

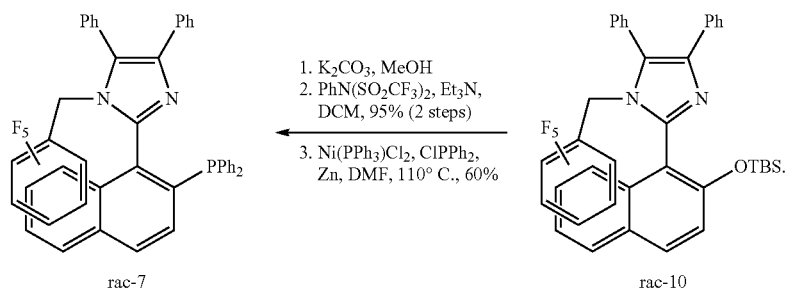

One exemplary method of forming a compound, among others, includes:

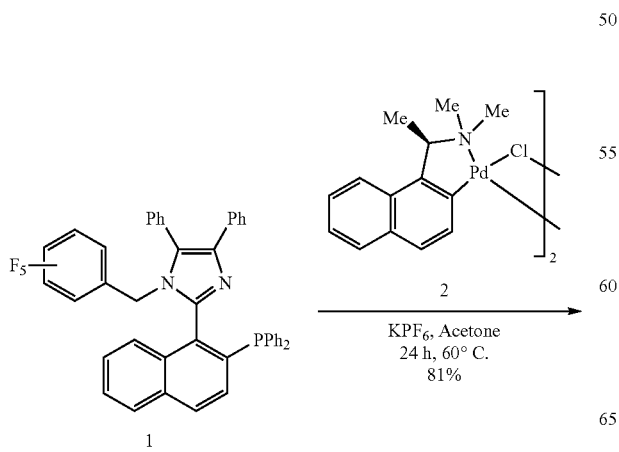

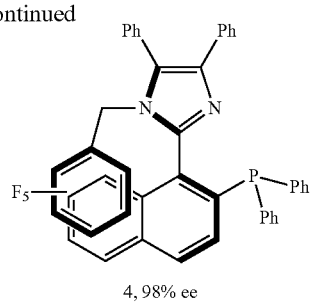

One exemplary method of forming a compound, among others, includes: using a biaryl compound as a catalyst in a reaction selected from one of the following: an enantioselective transformation, an enantioselective $A^3$ coupling, an alkyne addition asymmetric allylic alkylation, and an addition to a aliphatic or an aromatic aldehyde.

One exemplary method, among others, includes:
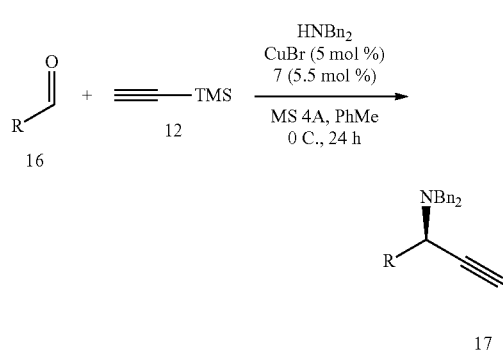
wherein R is shown in Table 1, Example 2, and compound 7 is
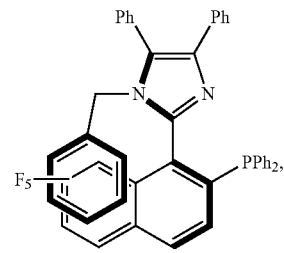
One exemplary method, among others, includes:
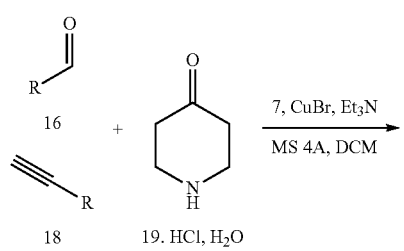
wherein compound 7 is
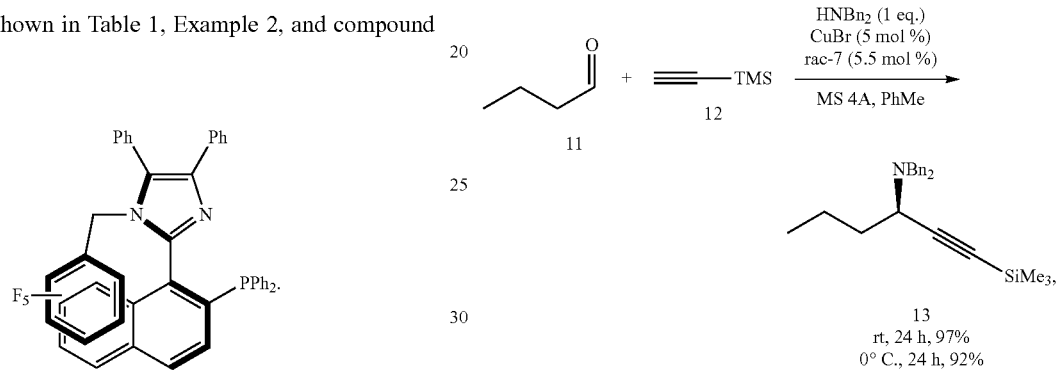
and wherein R is selected from SiMe$_3$ and Ph.
One exemplary method, among others, includes:
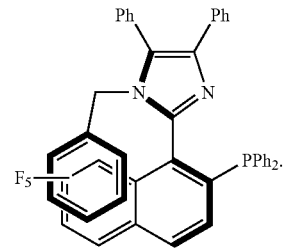
wherein compound rac-7 is
One exemplary method, among others, includes:
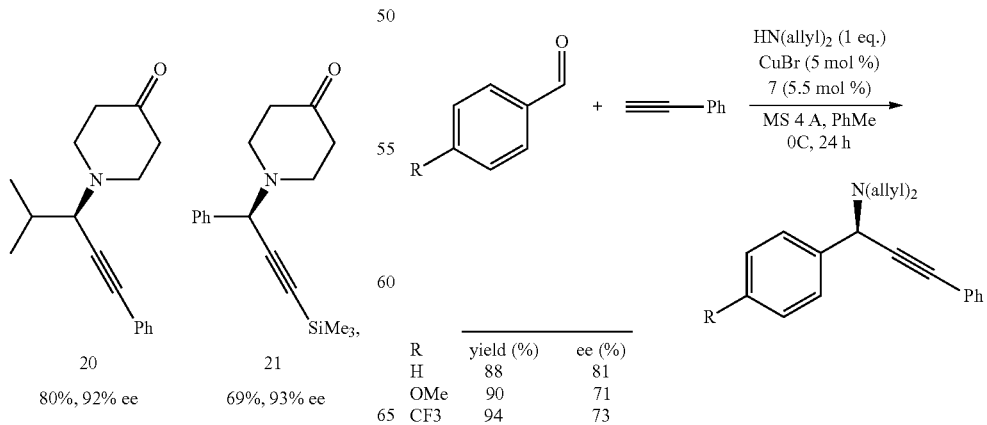
| R | yield (%) | ee (%) |
|---|---|---|
| H | 88 | 81 |
| OMe | 90 | 71 |
| CF3 | 94 | 73 | wherein compound 7 is

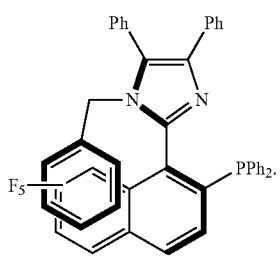

One exemplary composition, among others, includes: a complex having the following structure:

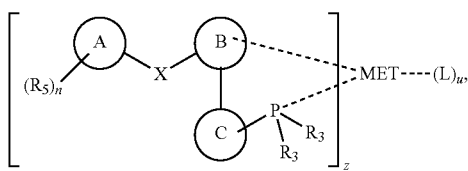

wherein MET is a metal selected from the group consisting of, but not limited to: a transition metal, Fe, Co, Ni, Ru, Rh, Pd, Os, Ir, Pt, Cu, and Au, wherein z is 1 to 3, wherein L refers to a ligand selected from the group consisting of: amide, phenolate, thiolate, halogen, carboxylate, acetylacetonate, phosphine, phosphite, and phosphoramidite, wherein u is 1 to 5, wherein MET is bonded to a N, S, or O group in the B ring.

Another exemplary composition, among others, includes: a complex having the following structure:

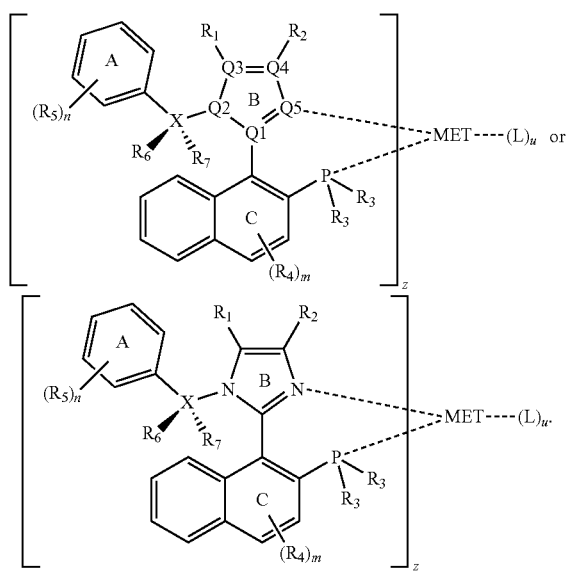

Other compositions, methods, features, and advantages of this disclosure will be or become apparent to one with skill in the art upon examination of the following drawings and detailed description. It is intended that all such additional systems, methods, features, and advantages be included within this description, be within the scope of this disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1.1 illustrates an ortho-substitution of a compound.
FIG. 1.2 illustrates the bond angle effect.
FIG. 1.3 illustrates QUINAP derivatives.
FIG. 1.4 illustrates the bite angle effect.
FIG. 1.5 illustrates strategies for increasing barrier height.
FIG. 1.6 illustrates using π-stacking to stabilize the ground state.
FIG. 1.7 illustrates $^1$H NMR spectra of 11 and 10 at 25° C. in CDCl$_3$.
FIG. 1.8 illustrates the coalescence data for 11 and 10.
FIG. 1.9 illustrates X-ray structure of 10.
FIG. 1.10 illustrates the comparison of pyrrole and indole biaryls.
FIG. 1.11 illustrates the crystal structure of free ligand, 2 perspectives.
FIG. 1.12 illustrates the crystal structures of 20 and BINAP in Pd(II)-complexes (additional ligands omitted for clarity).
FIG. 1.13 illustrates sites of modification.
FIG. 2.1 illustrates that the racemic ligand 1 can ultimately be reacted to form 4 in 98% ee.
FIG. 3.1 illustrates the configurationally unstable ligand 4.
FIG. 3.2 illustrate stabilization of the chiral conformation in 7.
FIG. 3.3 illustrates synthesis of racemic ligand 7.
FIG. 3.4 illustrates deracemization of ligand 7.
FIG. 3.5 illustrates X-Ray crystal structure showing π-stacking.
FIG. 3.6 illustrates alkyne addition with 19.
FIG. 4.1 illustrates transformation of the products 4a, 4i, and 4j to galipinine, angustureine, and cuspareine.
FIG. 4.2 illustrates palladium-catalyzed allylic alkylation.
FIG. 4.3 embodiments of ligands.
FIG. 5.1 illustrates axially chiral P,N-ligands.
FIG. 5.2 illustrates P,N-ligands containing a 5-membered heteroaromatic biaryl.
FIG. 5.3 illustrates geometrical distinctions between 6 and 5-membered rings in a heteroaromatic biaryls.
FIG. 5.4 illustrates using arene-arene interactions to stabilize the chiral conformation in biaryls.
FIG. 5.5 illustrates $^1$H NMR spectra (300 MHz in CDCl$_3$) of 13 and 14.
FIG. 5.6 illustrates the temperature-dependent NMR signals (300 MHz in CDCl$_3$) of the methylene protons in 13 and 14.
FIG. 5.7 illustrates the X-Ray crystal structure of 14.
FIG. 5.8 illustrates the variation of the naphthalene ring.
FIG. 5.9 illustrates the variation of the benzyl group.
FIG. 5.10 illustrates the complexation of racemic ligand rac-5 with palladacycle 24 and equilibration to a single diastereomer 25.
FIG. 5.11 illustrates the complexation with palladacycle 27.
FIG. 5.12 illustrates ortep plot of 2526 cocrystal (25 right, 26 left) with hydrogen atoms and PF6-counterions omitted for clarity.
FIG. 5.13 illustrates conformation analysis of diastereomers 25 and 26 (counterions omitted and phenyl groups displayed in wireframe for clarity).

FIG. 5.14 illustrates comparison between X-ray crystal structures of StackPhos 5, 25, and 29 (chiral auxiliary, hydrogen atoms, and counterions omitted for clarity).

FIG. 5.15 illustrates $A^3$-coupling employing ligand 5.

FIG. 5.16A illustrates ortep plot of QUINAP/CuBr complex 33. FIG. 5.16B illustrates ortep plot of dimer 34. FIG. 5.16C illustrates the proposed formation of complex 34 (phenyl groups shown in wireframe for clarity).

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, catalysis, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "substituted" refers to any one or more hydrogens on the designated atom that can be replaced with a selection from the indicated group, provided that the designated atom's normal valence is not exceeded, and that the substitution results in a stable compound. The term "substituted," as in "substituted alkyl", "substituted aryl," "substituted heteroaryl", and the like means, unless defined otherwise herein, at least that the substituted group can contain in place of one or more hydrogens a group such as alkyl, hydroxy, amino, halo, trifluoromethyl, cyano, —NH(alkyl), —N(alkyl)$_2$, lower alkoxy, lower alkylthio, or carboxy, and thus embraces the terms haloalkyl, alkoxy, fluorobenzyl, and the sulfur and phosphorous containing substitutions referred to below. In an embodiment, "substituted" refer to at least the substituted group can contain in place of one or more hydrogens a group such as halo or C1 to C3 alkyl group.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Unless stated otherwise, "alkyl" or "alkyl group" includes substituted and unsubstituted alkyls. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Unless stated otherwise, "cycloalkyl" includes substituted and unsubstituted cycloalkyls. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "aryl" as used herein, refers to an aromatic monocyclic or multicyclic ring system (fused rings). Unless stated otherwise, "aryl" includes substituted and unsubstituted aryls. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Unless stated otherwise, "heteroaryl" includes substituted and unsubstituted heteroaryls. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "benzenoid" is used herein to denote a substituted benzene ring. Unless stated otherwise, "benzenoid" includes substituted and unsubstituted benzenoids.

The term "alkoxide" is used herein to denote a conjugate base of an alcohol that includes an alkyl group.

The term "phenoixde" is used herein to denote a conjugate base of an alcohol that includes a derivative of benzene.

DISCUSSION

Embodiments of the present disclosure provide for biaryl ligands (also referred to herein as "biaryl compound"), biaryl complexes, methods of making biaryl compounds, methods of making single enantiomers of these biaryl compounds, methods of use (e.g., catalysis), and the like. Embodiments of the present disclosure are advantageous over other biaryls that are commercially available since those of the present disclosure can be readily prepared and tuned, which increases their effectiveness and reducing costs.

Embodiments of the biaryl compound are designed to lower their ground state energy, rendering them chiral. Use of ground state stabilization to render biaryls atropisomeric is previously unknown. In an embodiment, π-stacking (e.g., part or whole of the A ring with part of whole of the C ring) is used to increase the barrier to rotation, which allows highly versatile 5-membered heterocyclic aromatics to be formed. Embodiments can be produced in high enantiomeric excess and they impart high enantioselectivity in asymmetric reactions. Embodiments of these biaryl compounds can be used in asymmetric catalysis. In particular, embodiments of the biaryl compounds disclosed herein can be used in enantioselective transformations such as those described herein, but not limited to, enantioselective $A^3$-coupling, alkyne addition reactions, asymmetric allylic alkylation, and addition to aliphatic and aromatic aldehydes. Additional details are provided herein and in the Examples.

In an embodiment, the single biaryl enantiomer can have the following structure (or shown bonded to a metal):

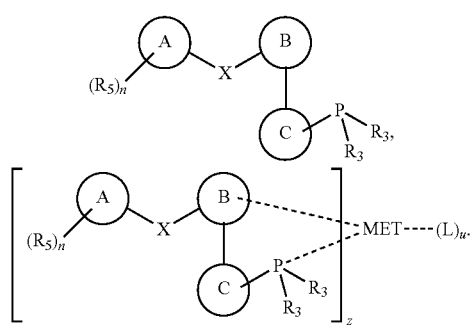

Although each ring (e.g., ring A, B, and C) and R group (e.g., $R_1$ to $R_7$, some of which are not shown above, but in other embodiments) is described separately herein and list several possible groups, any combination of the rings and the corresponding groups described and/or the R groups can be combined to form a plurality of distinct compounds, each of which is intended to be covered by the description provided herein. Each and every possible individual combination is not explicitly disclosed but is intended to be disclosed. MET refers to a metal such as a transition metal, Fe, Co, Ni, Ru, Rh, Pd, Os, Ir, Pt, Cu, Au, or the like, where z can be 1 to 3. L refers to a ligand (e.g., amide, phenolate, thiolate, halogen, carboxylate, acetylacetonate, phosphine, phosphite, phosphoramidite, or the like) and u can be 0 or 1 to 5. In an embodiment, MET can be bonded to one or more ligands. In an embodiment, the MET is bonded to a N, S, or O group in the B ring.

In an embodiment, the A ring (shown in the structure above) can be a benzenoid, a 5 or 6-membered heteroaromatic ring, or an aryl or heteroaryl fused-ring system (e.g., including 5 and/or 6 membered rings). In an embodiment, the A ring can be an aryl group. In an embodiment, each of the $R_5$ groups is independently selected from: hydrogen, a halogen group, a cyclic or linear, alkyl group, an aryl group, a —OR group, a —SR group, a —SiR$_3$ group, a NR$_2$ cyclic or linear group. In an embodiment, each $R_5$ group can be a halogen such as F. In an embodiment, R can be selected from: hydrogen, a cyclic or linear, alkyl group, or an aryl group, wherein n is 1 to 5. In an embodiment X can be $CR_2$ or $SO_2$, where each R group is independently selected.

In an embodiment, the B ring (shown in the structure above) can be selected from a 5-member or fused-ring heteroaromatic system (e.g., including 5 and/or 6 membered rings). In an embodiment, the B ring can include 1 to 5 N, S, O, or a combination of atoms in the ring(s). In an embodiment, the B ring can include 2 N atoms in a 5-membered heteroaromatic ring. In an embodiment, the B ring can include one or more moieties ("R" groups, such as $R_1$ and $R_2$ described herein) bonded to the ring(s).

In an embodiment, the C ring (shown in the structure above) can be a benzenoid, a 5 or 6-membered heteroaromatic ring, or an aryl or heteroaryl fused-ring system (e.g., including 5 and/or 6 membered rings). In an embodiment, the C ring can include an aryl fused-ring system (e.g., naphthyl group). In an embodiment, the $R_3$ groups can be independently: hydrogen, a cyclic or linear, alkyl group, an alkoxide, a phenoxide, an aryl group, or a substituted amine. In an embodiment, each $R_3$ group, independently, can be an aryl group such as phenyl.

In an embodiment, the biaryl compound can include any combination of: the A ring can be an aryl group, each $R_5$ group can be a halogen (e.g., F), the B ring can include 1 to 5 N, S, and/or O atoms in the ring(s) or the B ring can include 2 N atoms in a 5-membered heteroaromatic ring, the C ring can include an aryl fused-ring system, and/or each $R_3$ group can be an aryl group (e.g., phenyl).

In an embodiment, the biaryl compound can have the following structure (or shown bonded to a metal):

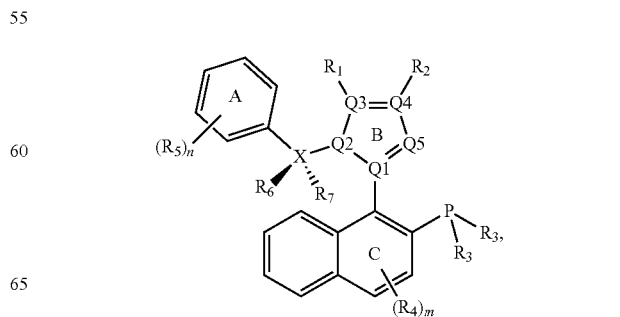

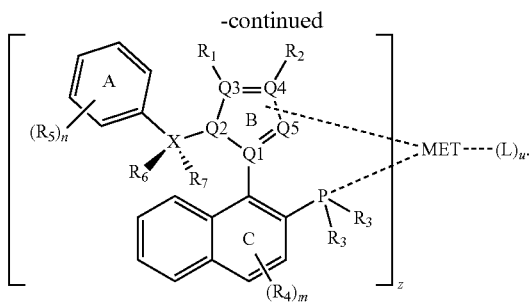

In an embodiment, the A ring (shown in the structure above) can be a benzenoid, a 5 or 6-membered heteroaromatic ring (not shown), or an aryl or heteroaryl fused-ring, system (not shown). In an embodiment, the A ring is a phenyl group. In an embodiment, each of the $R_5$ groups can independently be: hydrogen, a halogen group, a substituted or unsubstituted, cyclic or linear, alkyl group, a substituted or unsubstituted aryl group, a —OR group, a —SR group, a —SiR$_3$ group, a NR$_2$ cyclic or linear group. In an embodiment, R can be: hydrogen, a substituted or unsubstituted, cyclic or linear, alkyl group, or a substituted or unsubstituted aryl group. In an embodiment, each $R_5$ group can be a halogen such as F. Subscript n can be 1 to 5. In an embodiment, X can be C or S. In an embodiment, each $R_6$ and $R_7$ group can be independently: hydrogen, a substituted or unsubstituted, cyclic or linear, alkyl group, a substituted or an unsubstituted aryl group. In an embodiment, $R_6$ and $R_7$ can be hydrogen.

In an embodiment, the B ring (shown in the structure above) can be a 5-member or a fused-ring heteroaromatic (not shown) system. Q1, Q2, Q3, Q4, and Q5 are each independently selected. In an embodiment, at least one of Q1, Q2, Q3, Q4, and Q5 can be N, O, or S, and the other of Q1, Q2, Q3, Q4, and Q5 can be C, N, O, or S. In an embodiment, the B ring can be a 5-membered ring having one N atom and one O or S atom. In an embodiment, the B ring can include 1 to 5 N atoms or 2 to 5 N atoms, in particular, the B ring is a 5-membered ring having 2 N atoms. In an embodiment, a combination of N, O, and/or S atoms can be used in the 5-member or fused-ring heteroaromatic system, where atoms that are not N, O, or S atoms are carbon atoms.

In an embodiment, the biaryl compound structure can include one of the following embodiments:

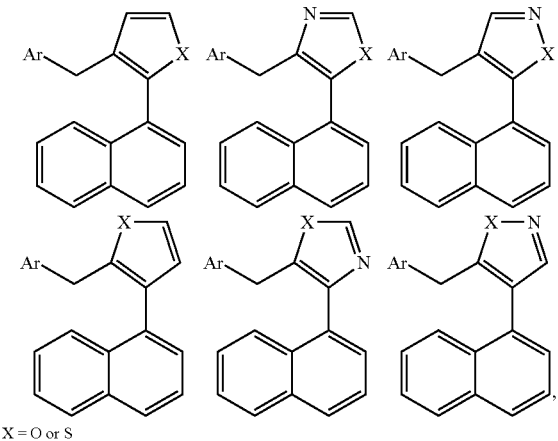

X = O or S where the R groups can be those described herein and positioned as noted herein and the P group is positioned on the C ring such as noted herein.

In an embodiment, each $R_1$ and $R_2$ group can independently be selected from: hydrogen, a halogen group, a substituted or unsubstituted, cyclic or linear, alkyl group, a substituted or unsubstituted aryl group, a —OR group, a —SR group, a —SiR$_3$ group, a NR$_2$ cyclic or linear group. In an embodiment, each of $R_1$ and $R_2$ can be an aryl group such as a phenyl group. In an embodiment, R can be: hydrogen, a substituted or unsubstituted, cyclic or linear, alkyl group, or a substituted or unsubstituted aryl group.

In an embodiment, the C ring (shown in the structure above) can be a benzenoid, a 5 or 6-membered heteroaromatic ring, or an aryl or heteroaryl fused-ring, system. In an embodiment, the C ring can be a naphthyl group including the P group and $R_4$. In an embodiment, each of the $R_4$ groups can independently be selected from: hydrogen, a halogen group, a substituted or unsubstituted, cyclic or linear, alkyl group, a substituted or unsubstituted aryl group, a —OR group, a —SR group, a —SiR$_3$ group, a NR$_2$ cyclic or linear group. In an embodiment, each of the $R_4$ groups is hydrogen. Subscript n can be 1 to 5. In an embodiment, R can be: hydrogen, a substituted or unsubstituted, cyclic or linear, alkyl group, or a substituted or unsubstituted aryl group. In an embodiment, each of the $R_3$ groups can independently be selected from: hydrogen, a cyclic or linear, alkyl group, alkoxides, phenoxides, aryl groups, or substituted amines. In an embodiment, each $R_3$ can be an aryl group such as a phenyl group.

MET refers to a metal such as, but not limited to, transition metals, Fe, Co, Ni, Ru, Rh, Pd, Os, Ir, Pt, Cu, Au, or the like, where z can be 1 to 3. L refers to a ligand (e.g., amide, phenolate, thiolate, halogen, carboxylate, acetylacetonate, phosphine, phosphite, phosphoramidite, or the like) and u can be 0 or 1 to 5. In an embodiment, MET can be bonded to one or more ligands. In an embodiment, the MET is bonded to a N, S, or O group in the B ring, where the position can depend upon the Q1, Q2, Q3, Q4, and Q5. The bond to the B ring is shown as to the center of the B ring, and this indicates that the bond can be to any one of Q1, Q2, Q3, Q4, and Q5, and in particular, to Q5.

In an embodiment, the biaryl compound can have the following structure (or bonded to a metal):

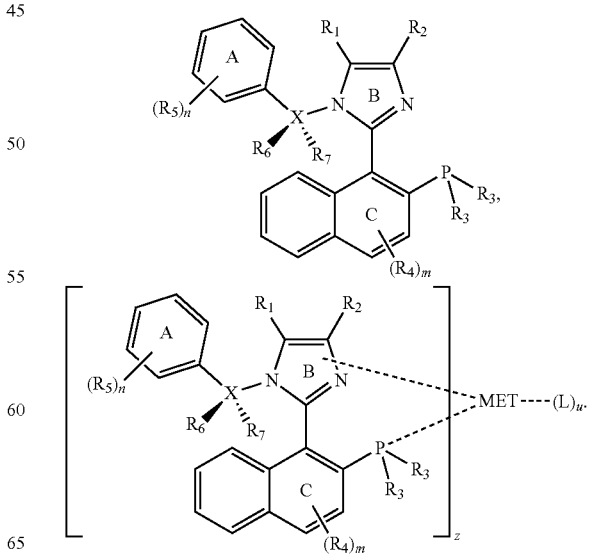

In an embodiment, each $R_5$ can be a halogen such as F. In an embodiment, each $R_3$ group can be an aryl group such as a phenyl group. In an embodiment, each of $R_1$ and $R_2$ can be an aryl group such as a phenyl group. In an embodiment, each $R_4$ is hydrogen. MET refers to a metal such as a transition metal, Fe, Co, Ni, Ru, Rh, Pd, Os, Ir, Pt, Cu, Au, or the like, where z can be 1 to 3. L refers to a ligand (e.g., amide, phenolate, thiolate, halogen, carboxylate, acetylacetonate, phosphine, phosphite, phosphoramidite, or the like) and u can be 0 or 1 to 5. In an embodiment, MET can be bonded to one or more ligands.

In an embodiment, the biaryl compound can include the following:

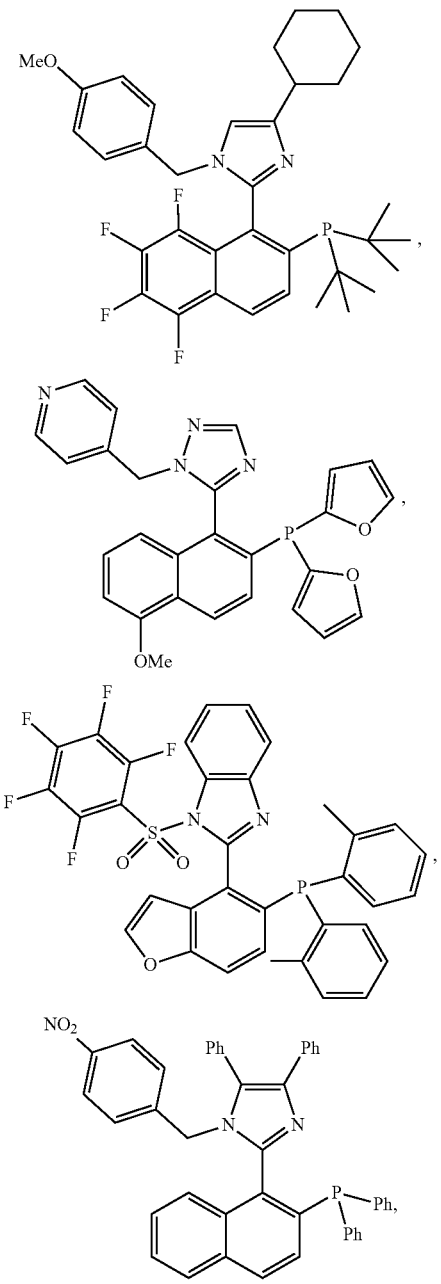

-continued

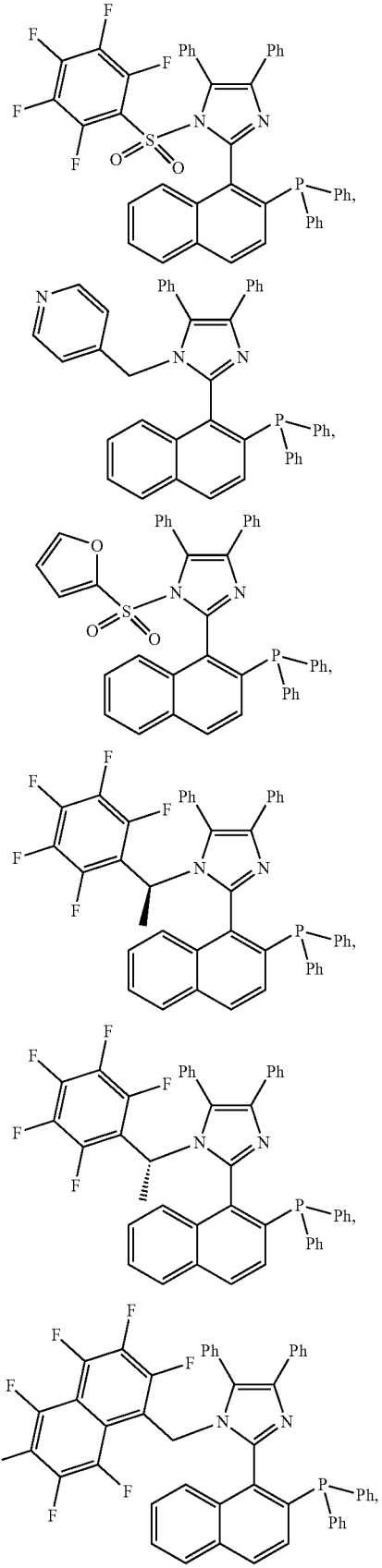

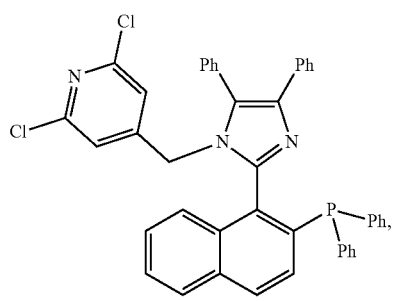
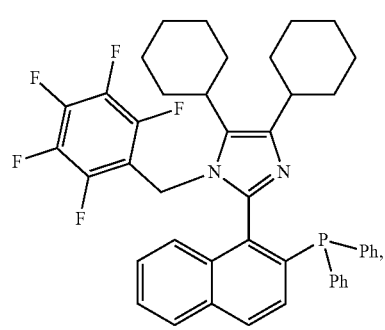
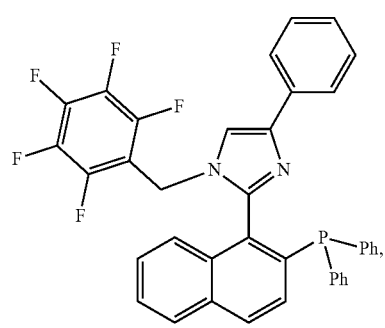
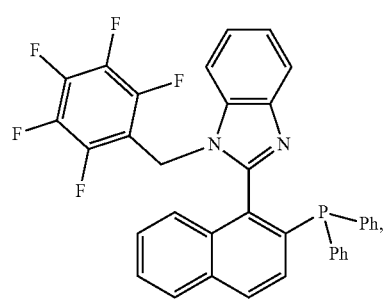
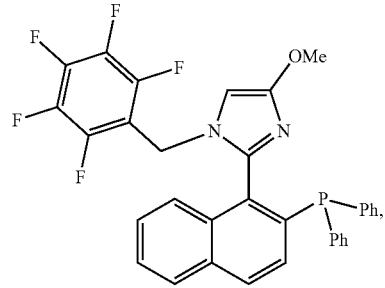
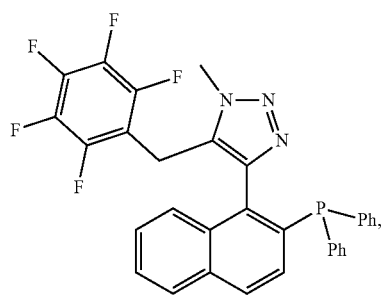
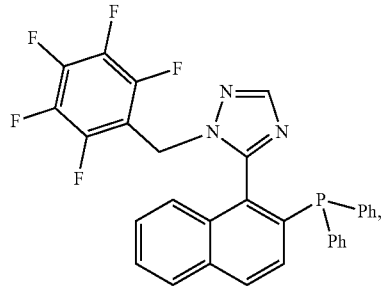
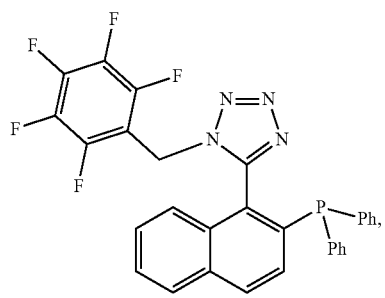
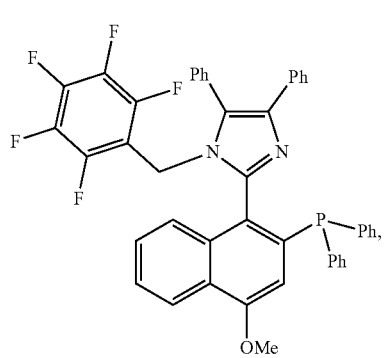
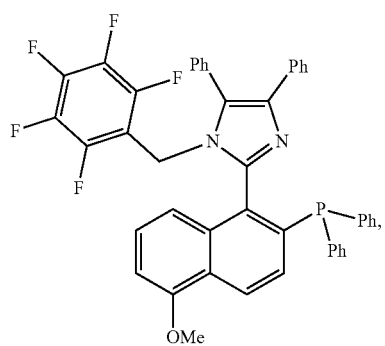

-continued

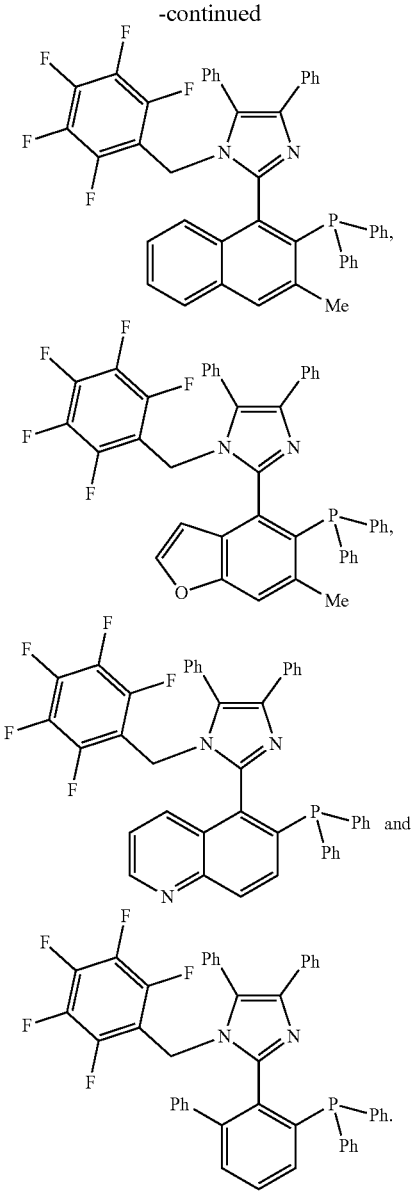

In an embodiment, each of the biaryl compounds described herein can be a mixture of enantiomers (e.g., a racemic mixture) or can be a single enantiomer. In an embodiment, a racemic mixture can be deracemized by formation of a single diastereomer of complex with chiral palladium complex. The decomplexation of the complex to release the biaryl ligand in high ee and chemical yield can be achieved under appropriate conditions, such as those described in the Examples. In addition, conducting the reaction at low temperature provides the biaryl ligand at high ee and is highly reproducible. This biaryl ligand is configurationally stable and the follow provides an efficient method for its preparation as a single enantiomer (both enantiomers are readily available). Additional details regarding the methods for forming a single enantiomer are described in the Examples.

A method of making the biaryl compound having following structure:

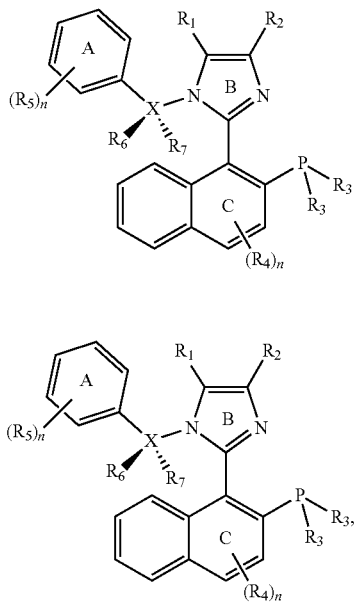

can include the following general scheme.

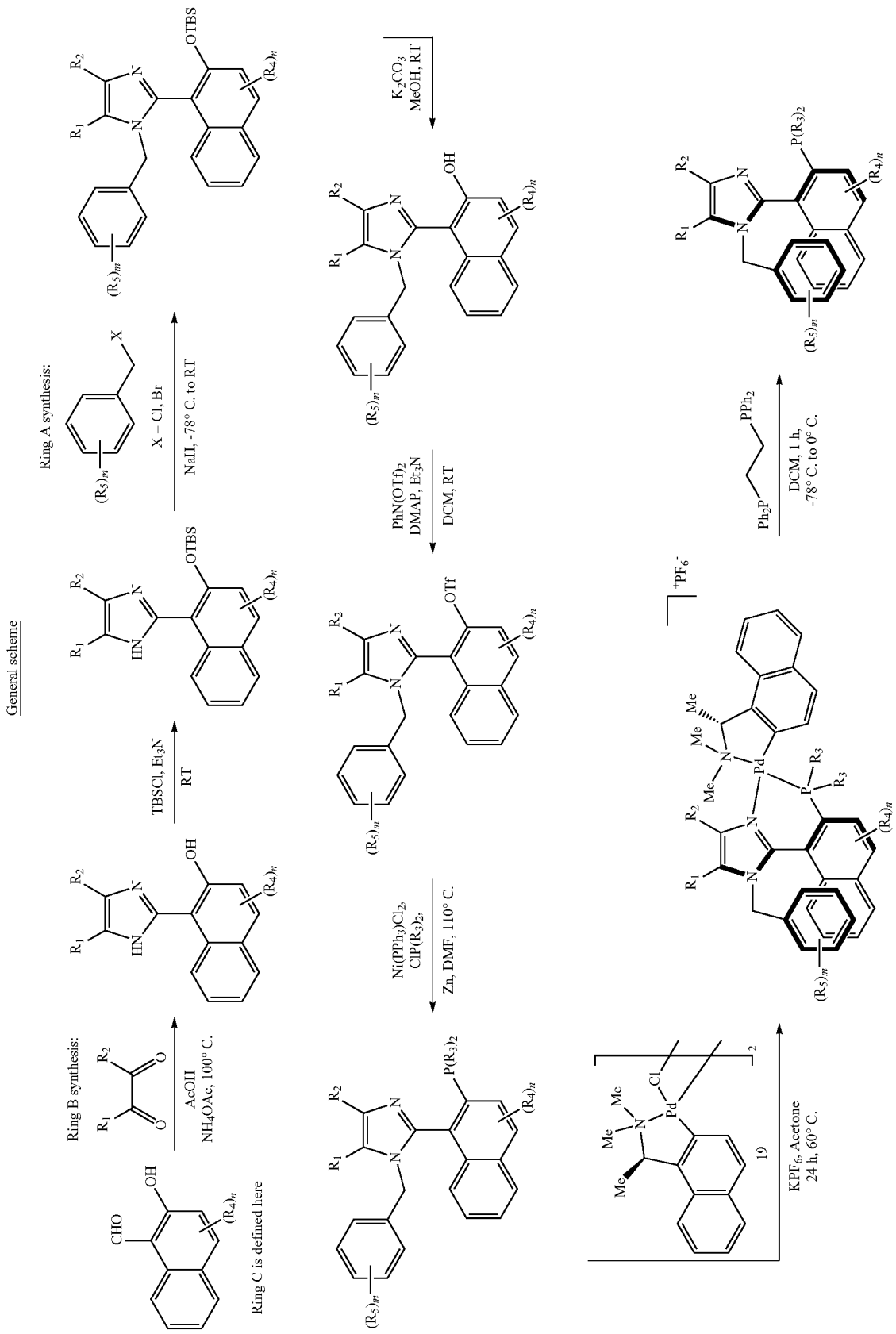

wherein the solvents and reagents used can be substituted with known equivalent solvents and/or reagents to accomplish the same or similar results of forming the biaryl compound.

In an embodiment, a biaryl compound of the present disclosure can be formed using the following reaction sequence:

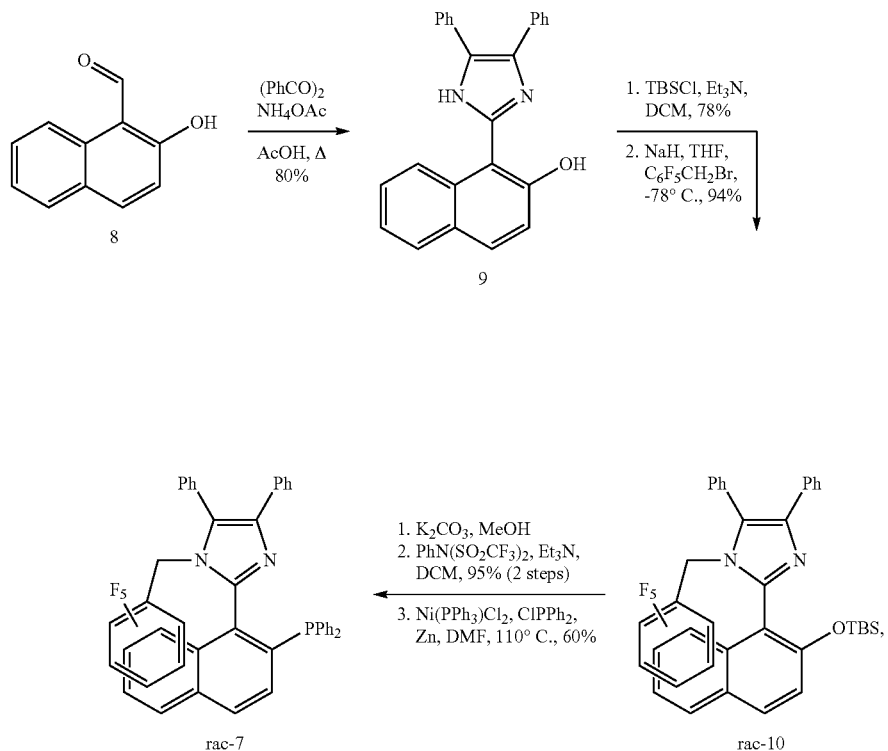

where other alternative reactants and solvents can be used as noted above to form the biaryl compound. The racemic mixture can be deracemized by formation of a single diastereomer as shown below:

where the reactants and solvents can be replaced with appropriate compounds to produce the single diastereomer product. Additional details are provided in the Examples.

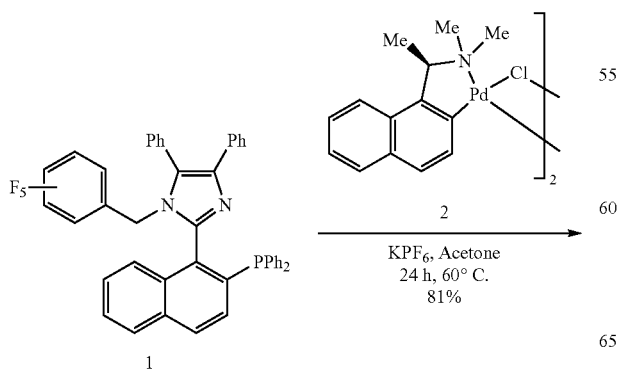

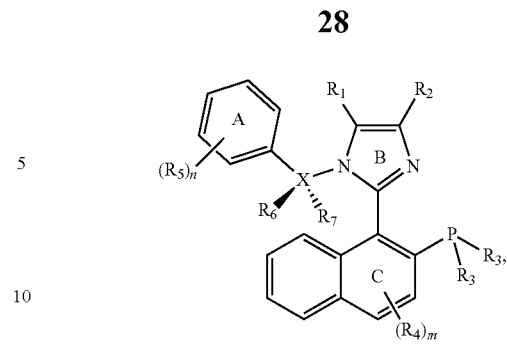

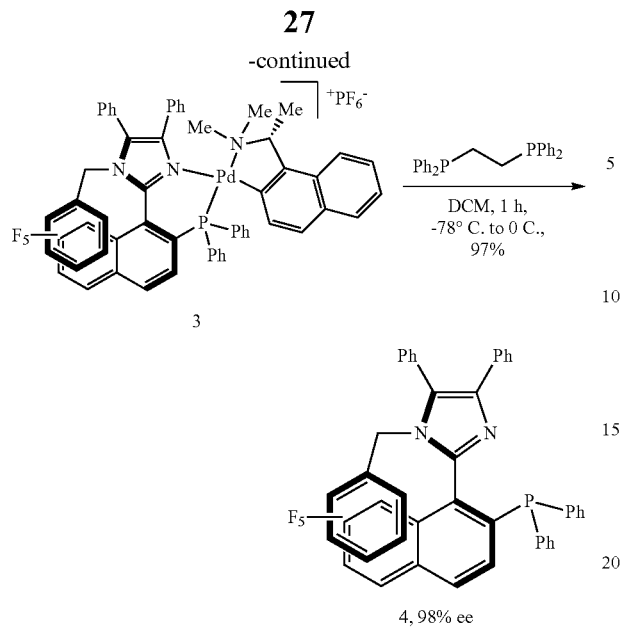

As noted above, biaryl compounds, such as

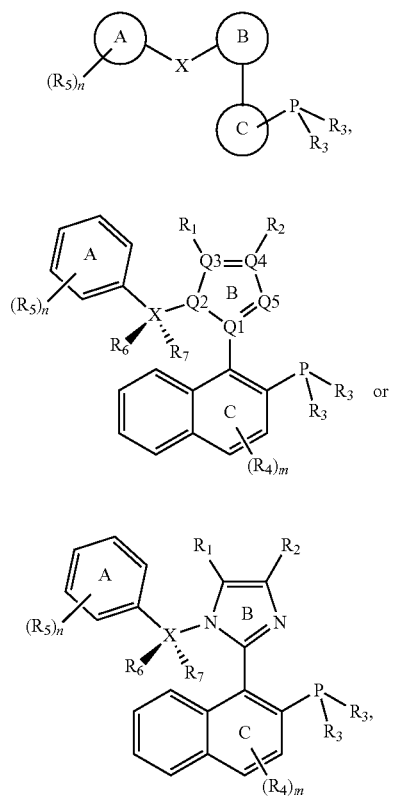

or the biaryl complex counterparts can be used as a catalyst (e.g., asymmetric catalysis). In particular, the biaryl compounds can be used in reactions such as: an enantioselective transformation, an enantioselective $A^3$ coupling, an alkyne addition asymmetric allylic alkylation, an addition to an aliphatic or an aromatic aldehyde. For example, the following are exemplary reactions, where "7" can include anyone of the compounds represented by or "7" can be the compound noted as "7" in Example 3. In addition, other alternative solvents and reactants can be used in place of the shown solvents and reactants as long as they produce the desired product.

In an embodiment, enantioselective $A^3$ coupling can be accomplished using embodiments of the biaryl compound, as shown in the reaction below:

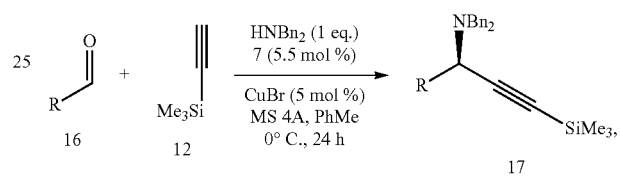

where R can include groups shown in Table 1, Example 3.

In an embodiment, an alkyne addition reaction can be accomplished using embodiments of the biaryl compound, as shown in the reaction below:

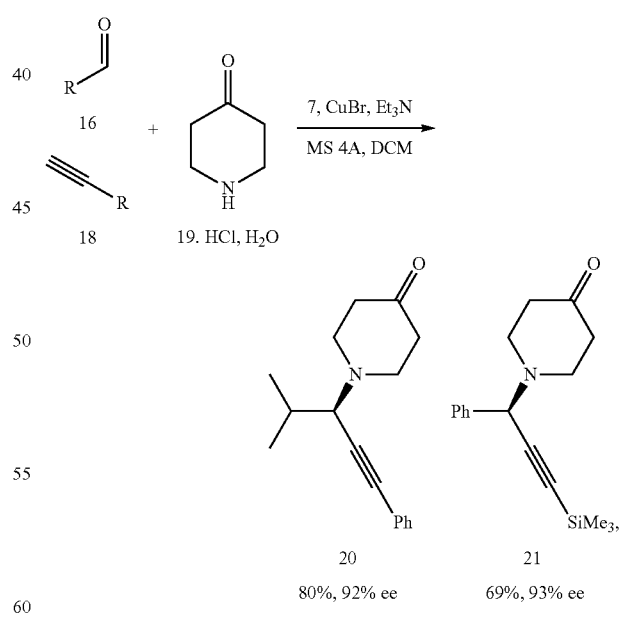

80%, 92% ee 69%, 93% ee, where R is selected from SiMe₃ and Ph.

In an embodiment, an enantioselective $A^3$ coupling can be accomplished using embodiments of the biaryl compound, as shown in the reaction below:

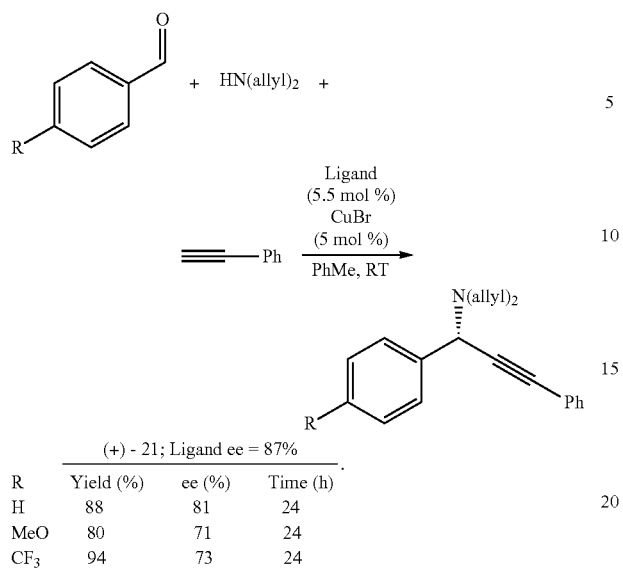

| R | Yield (%) | ee (%) | Time (h) |
|---|---|---|---|
| H | 88 | 81 | 24 |
| MeO | 80 | 71 | 24 |
| CF$_3$ | 94 | 73 | 24 |

(+)-21; Ligand ee = 87%

Now having described embodiments of the present disclosure in general, the following provides more details regarding embodiments of the biaryl compounds, methods of making biaryl compounds, and methods using biaryl compounds.

EXAMPLES

Now having described the embodiments of the disclosure, in general, the example describes some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Introduction

A multitude of academic and industrial processes rely on chiral ligands to establish the stereocenters in fine chemicals.[1] For example, Takasago International produces approximately 3,000 tons of menthol per year using an enantioselective hydrogenation reaction with BINAP as a chiral ligand (see structure below).[2] BINAP belongs to a family of ligands called atropisomers, where the molecule is rendered chiral by restricted rotation about a sigma-bond, as illustrated by the lack of chiral centers in the molecules below.

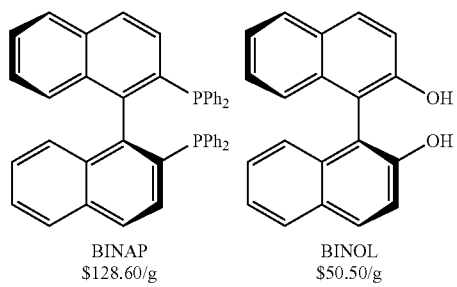

BINAP
$128.60/g

BINOL
$50.50/g

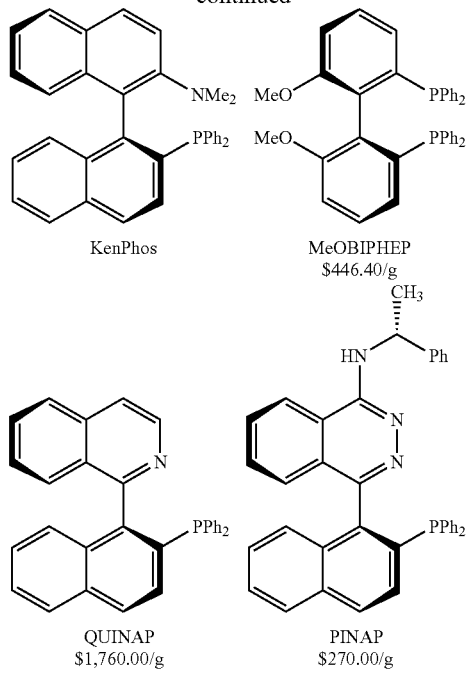

KenPhos

MeOBIPHEP
$446.40/g

QUINAP
$1,760.00/g

PINAP
$270.00/g

Transition metal complexes ligated with BINAP function so incredibly well, in such a vast number of different reactions that it is referred to as a privileged ligand,[3] and many structural variants are built upon this ligand's framework.[2c] The phosphorous atoms have been changed to other heteroatoms such as oxygen and nitrogen to produce ligands such as BINOL and KenPhos. More significantly, the aromatic systems have been modified to benzenoid aromatics (BIPHEP) and heteroaromatics (QUINAP, PINAP).[4,5] In practice, these types of modifications are made to increase the enantioselectivity in a given reaction and, as a consequence, an extremely large number of structural variants with small modifications have been prepared.[2c] These incrementally modified ligands have been successful in many cases, but can be very difficult and costly to prepare when a ligand such as a modified QUINAP ($1,700/g) is needed. More importantly, this strategy has resulted in a significant structural homology within this class of ligands, namely the two aryl rings of the biaryl are always 6-membered aromatics or fused 6-membered aromatic systems. This limits the steric and electronic tuning of these compounds and severely restricts the spectrum of known aromatic systems, which are rife with chemical diversity, to what is available with 6-membered ring systems. Herein we disclose a novel strategy to access new 5-membered heteroaromatic biaryls, demonstrate proof of principle, prepare highly enantioenriched ligands, and substantiate our claim that the ligands will be highly effective in enantioselective transformations with several examples.

BACKGROUND

A perfect ligand system for enantioselective transformations would be able to accommodate both small and large substrates in the "chiral pocket" and impart high selectivity across a range of reactants. Unfortunately, the current state-of-the-art often requires highly tuned congeners to modulate the steric demand in the chiral space about the reactive center to achieve this goal. In principle a "tighter", more sterically demanding, chiral pocket would be needed for smaller substrates and a more open reactive site for larger substrates. While it is easy to increase the steric demand, it is difficult to decrease it and maintain chirality, as described below. With chiral biaryl ligands, in the majority of these structures, rotation about the aryl-aryl σ-bond is hindered by ortho-substituents. As seen in FIG. 1.1, these groups closely protrude into each other's space. It follows that the most common strategy for increasing the barrier to rotation is increasing the bulk of the substituents. Rotation about the aryl-aryl σ-bond is always restricted by steric interactions between substituents, which also function to influence enantioselectivity. To accommodate bulky substrates, the size of the ortho substituents could be reduced but this reduces the biaryl's barrier to rotation. As such, the potential of biaryls bearing less sterically demanding groups and compounds with substantially different structures remains unknown.

A high barrier to rotation due to ortho-substituents relies on both the identity of the substituents and also the bond angles that orient the substituents in close proximity to each other.[6] As can be seen in FIG. 1.2, when 1 is rotated about the biaryl axis, $R_1$ approaches $R_2$ (or $R_3$). Since $R_1$ and $R_2$ are separated by 5 bonds, changes in bond angles in different aryl ring systems change the extent of the steric interactions. In comparing pyrrole 2 to benzene 1, it can be seen that $R_2$ and $R_3$ are much closer to the neighboring aryl ring in 1 than in 2. The 5-membered ring expands the ideal $R_2$—C—N bond angle to 126° in comparison to the 120° in benzene. This moves the groups apart, reducing steric interactions. A countless number of 5-membered heteroaromatics with varied steric and electronic properties are known, but this difficulty hinders their incorporation into biaryl ligands. This is highly unfortunate because heterocycles are much more easily prepared and modified than benzenoid aromatics.

We became interested in this area because changing the bond angles of the aromatic systems would also allow for a previously unexplored design modification of the chiral pocket, possibly creating a larger chiral space and most certainly a different class of ligand. Intriguing work from Brown and co-workers on QUINAP derivatives demonstrated that indole 3 and metal complexes thereof racemize rapidly (FIG. 1.3).[7] Although 5-membered biaryl heterocycles such as 3 are predicted to be useful ligands, they cannot be prepared enantiomerically pure. Increasing the steric bulk could overcome this, but is counterproductive to preparing ligands to accommodate larger substrates, which necessitates a new innovative strategy.

While steric effects are important for catalysis, the conformation of biaryls is also important because changing the dihedral angle $θ_1$ by rotation about the aryl-aryl bond (arrow a) influences the ligand-metal-ligand bite angle $θ_2$ as shown in FIG. 1.4.[8] Changing from 6- to 5-membered aromatics (e.g. QUINAP vs. 3) alters the bond angles and would be predicted to cause a significant change in the bite angle by moving the chelating groups "outward". This is schematically represented by the b arrows in FIG. 1.4, but systematic studies are lacking because altering the bond angles by "opening up" the substituents also reduces the barrier to rotation leading to loss of chirality.

Employing heterocyclic chiral biaryls has two other salient features of note. Firstly, heterocyclic phosphines have been reported to be greatly beneficial in many instances, such as the use of tri(2-furyl)phosphine in Heck reactions.[9] The second advantage is that the literature is rich with methods for the synthesis of heterocycles with a high degree of chemical diversity, suggesting that modular syntheses of a series of highly tunable ligand families will be available.

These potential applications suggest a fundamental question: How can aromatics with different ring sizes be incorporated into biaryls with sufficiently high barriers to rotation? More broadly, is there a novel strategy or design principle other than steric obstruction of bond rotation that could be employed? Graphically represented in FIG. 1.5, the strategy of increasing steric interactions to increase the barrier to rotation is like moving from energy curve a for racemization to one fitting b. If stabilizing interactions that favor the chiral ground state conformation were built into the structure, rotation about the sigma-bond would require that the energy contribution from these interactions also be overcome. This is like moving from energy curve a to c. By stabilizing the ground state, the barrier to rotation is also increased. Surprisingly, this simple concept has not been explored. The research outlined in here explores this premise in the context of designing new ligands and catalysts.

Results Our central hypothesis is that the barrier to rotation in biaryl systems can be increased by incorporating design elements that stabilize the ground state of these molecules. The stabilizing interaction explored here is π-stacking, but π-cation interactions, hydrogen bonding interactions, or even the introduction of covalent bonds can also be envisioned to serve this purpose.[10] As can be seen in FIG. 1.6, our system is comprised of biaryl rings A and B, and a C-ring appended for π-stacking. The system will be in equilibrium between a planar conformation 4 (A and B planar) or stacked conformation 5 (A and C π-stacked). Our supposition is that conjugation and π-stacking will cause 4 and 5 to be energy minima and our hypothesis is that stabilizing interactions in 5 will render this the lowest energy conformation.

Instead of relying on chiral probes to determine racemization rates, this system has the advantage that the appearance of $H_a$ and $H_b$ in 4 and 5 should be diagnostic in the ¹H NMR. In 4, $H_a$ and $H_b$ are enantiotopic and therefore would appear as a singlet, while in 5, $H_a$ and $H_b$ are diastereotopic with unique signals in the ¹H NMR spectrum. The difference in ¹H NMR spectra should make identifying which conformation is present straightforward, but also is advantageous because the barrier to rotation should be easily measured using variable temperature NMR methods.[11] Additionally, there is no need to prepare enantiomerically pure samples and the method is non-destructive so the barrier can easily be measured in a variety of solvents without the need for a new sample. The only requirement for use of the coalescence method is that $H_a$ and $H_b$ must be distinct signals that coalesce.

To test this hypothesis we chose model compounds 10 and 11 for comparison. These biaryl compounds were easily prepared from boronic acid 6[12] and bromonaphthalene 7 (Scheme 1.1), Suzuki coupling[13] provided 8, which was deprotected[14] to give 9 in 59% yield over two steps. The desired biaryl 11 was then accessed by simple benzylation. From 9, the pentafluorophenyl compound 33 was also readily prepared.

Scheme 1.1. Preparation of model compounds.

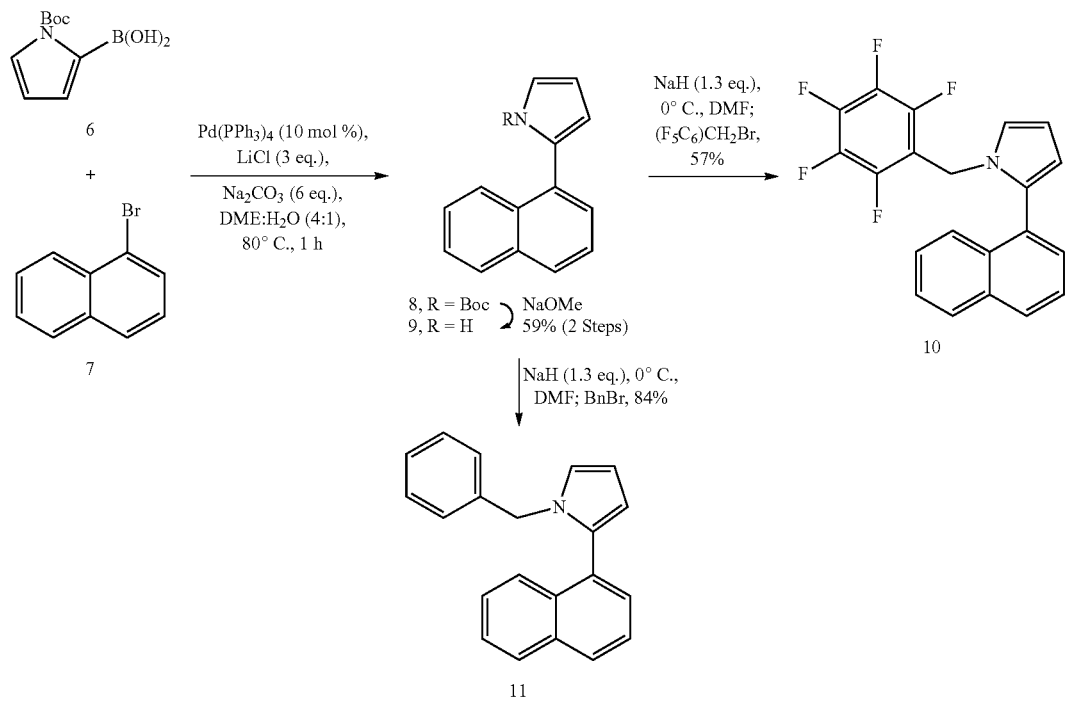

These two compounds are the basis for the initial test of our hypothesis. It is important to determine the portion of the barrier to rotation that can be attributed to π-stacking and how much inherent to the system. For this, pairs of compounds such as 10 and 11 need to be employed. Since fluorine and hydrogen are similar in size,[15] the difference in barrier height, $\Delta\Delta G^{\ddagger}$, can be interpreted as the electronic contribution and attributed to π-stacking.

As can be seen in the $^1$H NMR spectra (FIG. 1.7), the benzylic protons are a singlet in 11 and an AB pattern in 10. On the NMR timescale, there is free rotation about the aryl-aryl bond in 11, while rotation is restricted in 10. This demonstrates that changing the electronics of the system can bias the conformation to give the non-conjugated arrangement with smaller aromatic rings without bulky ortho-substituents. The barrier to rotation was determined and the coalescence temperature is strikingly different (FIG. 1.8). While the signals in 11 coalesce at 9° C., 10 had to be heated to 57° C. From these data, the barrier to rotation for 11 in CDCl$_3$ is 13.9 kcal/mol and for 10, 16.3 kcal/mol.

The spectrum indicates that 10 is not planar and the barrier dictates that it is not locked in a single conformation in solution. To gain further evidence of π-stacking, an X-ray structure was obtained (FIG. 1.9). The dihedral angle between the A- and B-rings is 880 and the A- and C-rings are π-stacked with a distance of 3.26 Å. The stacking is parallel and offset, but the rings are not perfectly parallel with the C-ring slightly canted away from the naphthalene. Similar experiments were also performed on fluorinated and non-fluorinated indole derivatives and the results were quite surprising. Interestingly, the coalescence temperatures are much higher with indoles (FIG. 1.10). To reach coalescence, 12 required heating to nearly 80° C.; a 17.6 kcal/mol barrier. It was previously thought that the B-ring linker would not influence the barrier height. This result clearly indicates the contrary and suggests that varying the heterocyclic B-ring is a worthy endeavor as it is a significant contributor to the barrier height.

We now have several pairs of heterocyclic biaryls (fluorinated/non-fluorinated). In each case the fluorinated, π-stacked compounds have a higher barrier to rotation. It is important to note that a barrier height of 17.6 kcal/mol is not sufficient for atropisomerism. However, these model studies demonstrate that π-stacking is indeed possible and that it increases the barrier height by ~2-3 kcal/mol. In functional molecules, there will be an increase in the steric component and inclusion of the π-stacking aryl group will provide an additional ~2-3 kcal/mol. Additionally, π-stacking should position the substituent away from the reactive center, furthering the goal of providing a chiral biaryl ligand that can accommodate larger substrates.

Results—Ligands and Catalysts

While the model compounds demonstrate that the concept is feasible, no functional groups are built into the molecules for further applications. There are a small number of known biaryl, C$_2$-symmetric, bis-phosphine ligands with 5-membered aromatics but these utilize traditional steric interactions to render them atropisomeric.[2c] As stated above, our interest in this area stems from the hypothesis that relatively unhindered C$_1$-symmetric compounds such as 3[7,16] (for which no reactions are currently known due to configurational instability) will be excellent ligands in enantioselective reactions.

Synthesis and Configurational Stability: We decided to prepare the novel phosphine-substituted imidazole 18 as it should be chiral and function as a P,N-ligand for enantioselective transformations (Scheme 1.2). The synthesis begins with commercially available 14 and after several straightforward steps provides triflate 17. Interestingly, 16 is chiral and its enantiomers can be separated by HPLC, but the corresponding non-fluorinated analogue is achiral with a coalescence temperature of 94° C. Conversion of 17 to 18 was accomplished by Ni-catalyzed cross-coupling.[17] This synthesis is scalable (multigram) and large quantities of the ligand are available.

Scheme 1.2. Synthesis of racemic 18.

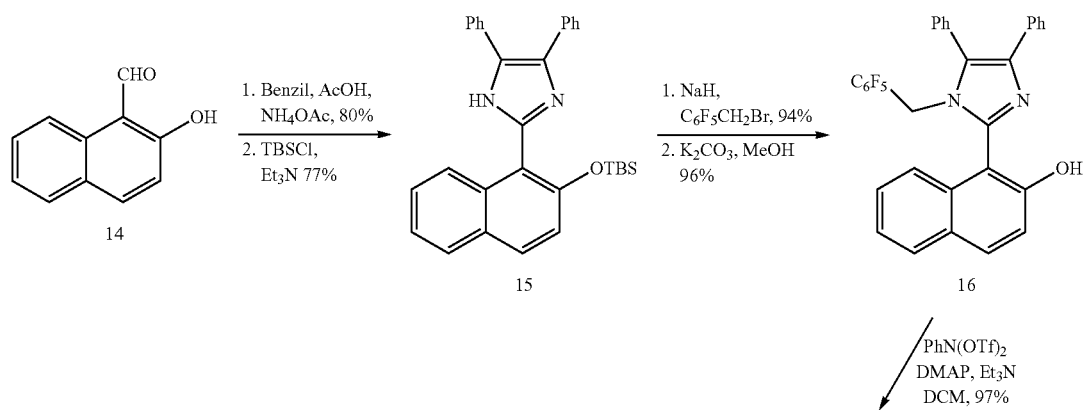

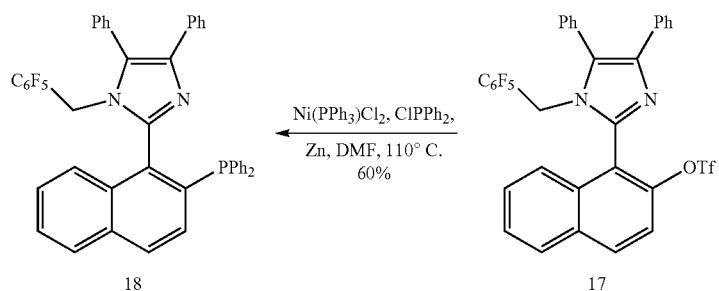

With a good source of the racemic ligand in hand, what remains for applications in enantioselective catalysis is determination of the configurational stability, resolution of the enantiomers, and preparation of metal complexes. P,N-ligands such as QUINAP and derivatives are commonly resolved by complexation with a chiral Pd-complex, separation of the diastereomers, and decomplexation to reveal the enantiomers of the ligand.[4,7,18] This route is fairly wasteful as a chiral complex is needed to recover half of the material. This is likely the reason for the high cost of QUINAP. As a first attempt, resolution was attempted using the same method. Unfortunately, all attempts to separate the enantiomers resulted in less than adequate results. This drove us to study the dynamic behavior of the ligand. Interestingly, we discovered that instead of resolution and recovery of half the material, all of the material could be converted to a single diastereomer of the ligand. Accordingly, the ligand 18 is converted to two diastereomeric palladium complexes by simply stirring with 19, however upon refluxing in acetone overnight, 20 is isolated as a single diastereomer as judged by $^1$H NMR spectroscopy (Scheme 1.3).

Scheme 1.3. Deracemization of ligand 18.

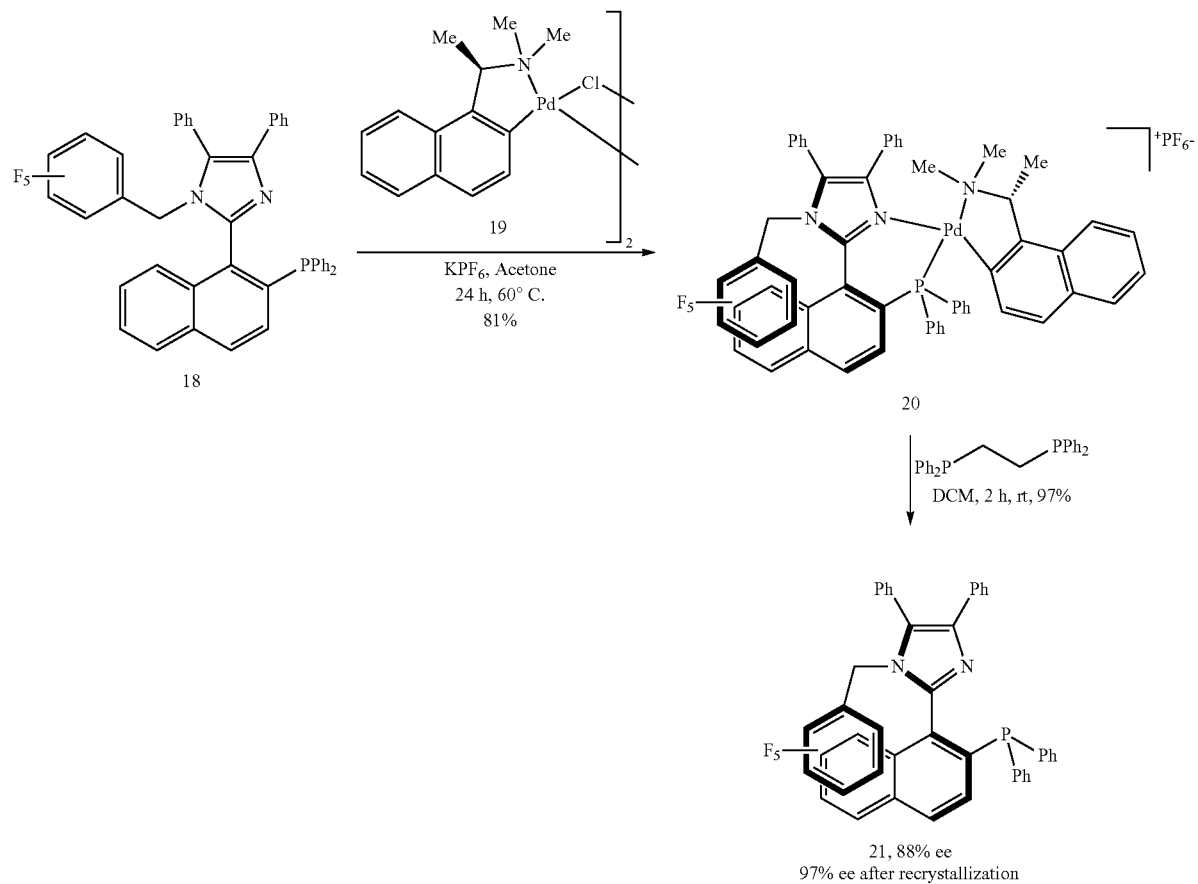

Free, deracemized ligand is then readily liberated from complex 20 by treatment with dppe to provide scalemic 21 in 88% ee (94:6 enantiomeric ratio). The ee of the ligand is readily determined by oxidation of the phosphine to the phosphine oxide and analysis by HPLC using a chiral stationary phase (Scheme 1.4).

Scheme 1.4 Oxidation and determination of ligand ee.

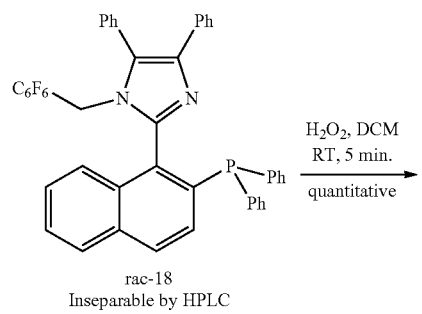

-continued

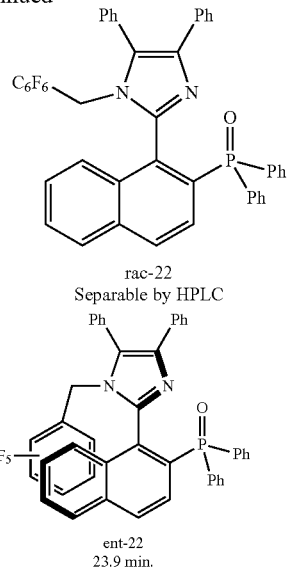

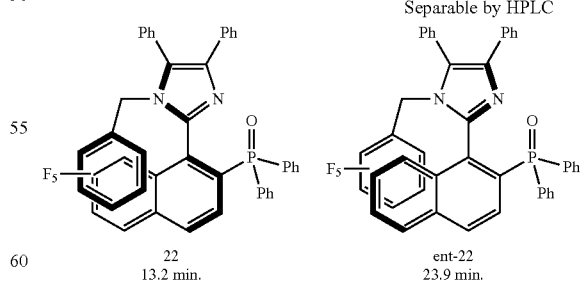

Column: CHIRALPAK® IA
Flow Rate: 1 ml/min
Eluent: 10% $^i$PrOH in Hexanes
$T_R$ = 13.2 min. and 23.9 min.

For use as a ligand, the ee needs to be increased even further. Using this recrystallization procedure, the ligand has been obtained in 97% ee and a superior procedure is outlined in Example 2.

Several important points warrant mention. Firstly, the free ligand is configurationally stable. The free ligand can be stored indefinitely as a solid without any decrease in ee. We have tested samples over several months now and see no indication of loss of ee. Secondly, the C-ring is π-stacked in the free ligand as can be seen in the crystal structure in FIG. 1.11.

Furthermore, we were able to obtain a crystal structure of the palladium complex 20. Much to our surprise, the X-ray structure of 20 revealed that this complex presents chiral space similar to that observed in BINAP complexes, which function well in an extremely large number of enantioselective reactions. This was unexpected as the ligands are extremely different in structure. As can be seen in FIG. 1.12, two phenyl groups (wireframed) adopt a propeller-like orientation about the metal center (Pd; pink) with empty space in the NE and SW quadrants. In BINAP-complexes, enantiodifferentiation is attributed to this arrangement. BINAP is a C₂-symmetric bis-phosphine with the open coordination sites being equivalent. Here we also have electronic differentiation of the coordination sites trans to P and N atoms, further controlling the chiral space for catalysis.

The data above demonstrates that heterocyclic biaryls with 5-membered ring components can be easily prepared, rendered chiral without incorporation of bulky ortho-substituents, prepared in optically pure form, and incorporate functional groups for use as ligands. What remains is demonstration that these compounds can effectively be used as ligands to catalyze enantioselective transformations. With ligand 21 in hand, some preliminary screening was done to see if it can induce enantioselectivity. Asymmetric allylic alkylation was chosen so that comparison could be made to QUINAP and BINAP, which have been referenced extensively above. Employing enantiopure BINAP and QUINAP, the product is obtained in 90% and 95% ee respectively (Scheme 1.5).[19] Using 21 (92% ee), the ee of the product is 89%. It should be noted that none of these are the best ligand for this specific transformation, but these data demonstrate that the ligands are effective at inducing enantioselectivity: 92% ee 21 functions as well as enantiopure BINAP and should surpass it when the ee is the same.

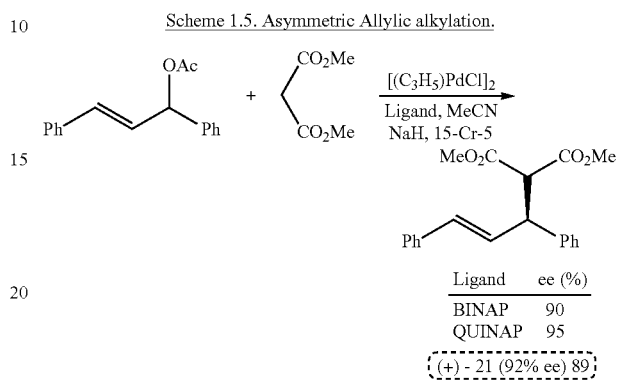

Scheme 1.5. Asymmetric Allylic alkylation.

| Ligand | ee (%) |
|---|---|
| BINAP | 90 |
| QUINAP | 95 |
| (+) - 21 (92% ee) | 89 |

We are interested in using these complexes to address limitations in current state-of-the-art systems. Knochel has reported employing QUINAP in three-component reactions.[20] Aromatic aldehydes were the most challenging substrates in his reports, displaying low reactivity and enantioselectivity. In these reactions ligand 21 was employed and using this novel compound in 87% ee (obtained prior to learning how to increase it's ee) it outperformed enantiopure QUINAP in both reactivity and selectivity (Scheme 1.6). Using our ligand in 87% ee, both electron deficient and electron rich aromatic aldehydes function well in the reaction. This is in contrast to the current stat-of-the-art where the reactions are low yield after long reaction times and provide the products in low enantiomeric excess. With this increased reactivity, it is likely that lower reaction temperatures can be employed.

Scheme 1.6. Cu-catalyzed three-component reactions.

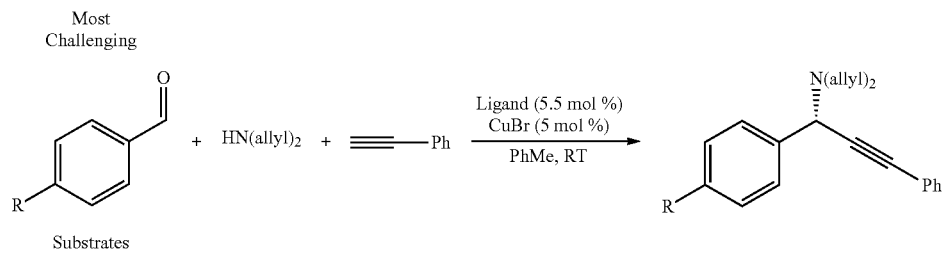

| | (+) - 21; Ligand ee = 87% | | | (R)-QUINAP; Ligand ee = > 99% | | |
|---|---|---|---|---|---|---|
| R | Yield (%) | ee (%) | Time (h) | Yield (%) | ee (%) | Time (h) |
| H | 88 | 81 | 24 | 91 | 70 | 96 |
| MeO | 80 | 71 | 24 | 76 | 60 | 120 |
| CF₃ | 94 | 73 | 24 | 43 | 63 | 120 |

As can be seen in Scheme 1.7, we have also worked on aliphatic aldehydes, with success. Using our ligand, now in 97% ee, the reaction functions quite well providing the product in 96% ee. It should be noted that this reaction was performed at 0° C. and was complete in 24 h.

Scheme 1.7. Addition to aliphatic aldehydes with high ee.

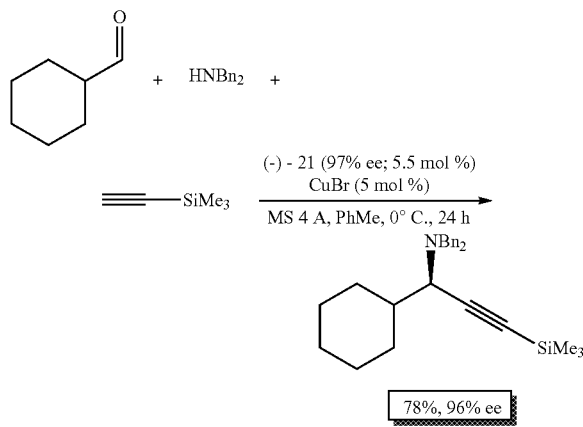

The reaction was also performed using aromatic aldehydes, dibenzylamine, and trimethylsilyl acetylene with ligand 21 in 97% ee. Again high chemical and optical yield was observed.

As can be seen above, ligand 21 functions extremely well and this is currently the most reactive and appears to be the most highly selective system for the so-called $A^3$-coupling reaction.[21]

The true power of this strategy is the ability to readily prepare interesting new ligand classes using this design principle. The current structure is also highly modular and one could envision a myriad of modifications that could easily be prepared (FIG. 1.13).

In summary, we have prepared anew class of 5-membered heteroaromatic ligands with the ground state stabilized via π-stacking. These ligands are readily prepared, isolated in high ee, are configurationally stable, and function to impart high ee in organometallic reactions. Additionally, they are highly modular and can be readily modified for either fine-tuning or to create a variety of different types of novel ligand classes.

REFERENCES

1. Noyori R. (Ed.), Asymmetric Catalysis in Organic Synthesis, Wiley, New York, 1994.
2. A) Noyori, R.; Takaya, H. BINAP: An Efficient Chiral Element for Asymmetric Catalysis. *Acc. Chem. Res.* 1990, 23, 345-350. B) Berthod, M.; Mignani, G.; Woodward, G.; Lemaire, M. Modified BINAP: The How and the Why. *Chem. Rev.* 2005, 105, 1801-1836. C) Shimizu, H.; Nagasaki, I.; Saito, T. Recent advances in biaryl-type bisphosphine ligands. *Tetrahedron* 2005, 61, 5405-5432.
3. A) Yoon, T. P.; Jacobsen, E. N. Privileged Chiral Catalysts. *Science* 2003, 299, 1691. B) Qi-Lin Zhou (Ed.), Privileged Chiral Ligands and Catalysts, Wiley-VCH, Weinheim, 2011.
4. Alcock, N. W.; Brown, J. M.; Hulmes, D. I. Synthesis and Resolution of 1-(2-Diphenylphosphino-lnaphthyl)isoquinoline; a P—N Chelating Ligand for Asymmetric Catalysis. *Tetrahedron: Asymmetry* 1993, 4, 743-756.
5. Knopfel, T. F.; Aschwanden, P.; Ichikawa, T.; Watanabe, T.; Carreira, E. M. Readily available biaryl P,N ligands for asymmetric catalysis *Angew. Chem., Int. Ed.* 2004, 43, 5971-5973.
6. Alkorta, I.; Elguero, J.; Roussel, C.; Vanthuyne, N.; Piras, P. Atropisomerism and Axial Chirality in Heteroaromatic Compounds. *Adv. Heterocycl. Chem.* 2012, 105, 1-188.
7 Claridge, T. D. W.; Long, J. M.; Brown, J. M.; Hibbs, D.; Hursthouse, M. B. Synthesis of 1-Methyl-2-diphenylphosphino-3-(1'-isoquinolyl)indole; an Easily Racemised Ligand giving Insights into Catalytic Asymmetric Allylation. *Tetrahedron* 1997, 53, 4035-4050.
8. Birkholz, M.-N.; Freixa, Z.; van Leeuwen, P. W. N. M. Bite angle effects of diphosphines in C—C and C—X bond forming cross coupling reactions. *Chem. Soc. Rev.*, 2009, 38, 1099-1118.
9. Andersen, N. G., Keay, B. A. 2-Furyl Phosphines as Ligands for Transition-Metal-Mediated Organic Synthesis *Chem. Rev.* 2001, 101, 997-1030.
10. A) Meyer, E. A., Castellano, R. K.; Diederich, F. Interactions with Aromatic Rings in Chemical and Biological Recognition. *Angew. Chem., Int. Ed.* 2003, 42, 1210-1250; B) Salonen, L. M., Ellermann, M., Diederich, F. Aromatic Rings in Chemical and Biological Recognition: Energetics and Structures. *Angew. Chem., Int. Ed* 2011, 50, 4808-4842.
11 Sutherland, I. O. The investigation of the kinetics of conformational changes by nuclear magnetic resonance spectroscopy. Annu. Rep. *NMR Spectrosc.* 1971, 4, 71-235.
12. Haynes, S. W.; Sydor, P. K.; Stanley, A. E.; Song, L.; Challis, G. L. Role and substrate specificity of the *Streptomyces coelicolor* RedHenzyme in undecylprodiginine biosynthesis. *Chem. Commun.*, 2008, 1865-1867.
13. Clift, M. D.; Thomson, R. J. Development of a Merged Conjugate Addition/Oxidative Coupling Sequence. Application to the Enantioselective Total Synthesis of Metacycloprodigiosin and Prodigiosin R1. *J Am. Chem. Soc.* 2009, 131, 14579-14583.
14. Hasan, I.; Marinelli, E. R.; Lin, L. C. C.; Fowler, F. W.; Levy, A. B. Synthesis and Reactions of N-Protected 2-Lithiated Pyrroles and Indoles. The tert-Butoxycarbonyl Substituent as a Protecting Group. *J. Org. Chem.* 1981, 46, 157-164.
15. Schlosser, M.; Michel, D. Introduction of fluorine into organic molecules: why and how. *Tetrahedron* 1996, 52, 99-108.
16. Figge, A., Altenbach, H. J., Brauerb, D. J., Tielmannc, P. Synthesis and resolution of 2-(2-diphenylphosphinylnaphthalen-1-yl)-1-isopropyl-1Hbenzoimidazole; a new atropisomeric P,N-chelating ligand for asymmetric catalysis. *Tetrahedron: Asymmetry* 2002, 13, 137-144.
17. Kwong, F. Y.; Chan, A. S. C.; Chan, K. S. Chelating Retardation Effect in Nickel Assisted Phosphination: Syntheses of Atropisomeric P,N Ligands. *Tetrahedron* 2000, 56, 8893-8899.
18. A) Otsuka, S.; Nakamura, A.; Kano, T.; Tani, K. Partial Resolution of Racemic Tertiary Phosphines with an Asymmetric Palladium Complex. *J. Am. Chem. Soc.* 1971, 93, 4301-4303; B) Tani, K.; Brown, L. D.; Ahmed, J.; Ibers, J. A.; Yokota, M.; Nakamura, A.; Otsuka, S. Chiral Metal Complexes. 4. Resolution of Racemic Tertiary Phosphines with Chiral Palladium(II) Complexes. The Chemistry of Diastereomeric Phosphine Pd(II) Species in Solution, and the Absolute Configuration of [(S)-

Isopropyl-tert-butylphenylphosphine]-[(R)—N,N-dimethyl-a-(2-naphthyl)-ethylamine-3C,N]chloropalladium (II) Determined by X-Ray Diffraction. *J. Am. Chem. Soc.* 1977, 99, 7876-7886. C) Allen, D. G.; Mclaughlin, G. M.; Robertson, G. B.; Steffen, W. L.; Salem, G.; Wild, S. B. Resolutions with metal complexes. Preparation and resolution of (R,S)-methylphenyl(8-quinolyl)phosphine and its arsenic analog. Crystal and molecular structure of (+)$_{589}$-[(R)-dimethyl(1-ethyl-naphthyl)aminato-C$^2$,N][(S)-methylphenyl(8-quinolyl)phosphine]palladium(II) hexafluorophosphate. *Inorg. Chem.* 1982, 21, 1007-1014.
19. A) Brown, J. M.; Hulmes, D. I.; Guiry, P. J. Mechanistic and Synthetic Studies in Catalytic Allylic Alkylation with Palladium Complexes of 1-(2-Diphenylphosphino-1-naphthyl)isoquinoline. *Tetrahedron* 1994, 50, 4493-4506. B) Yamaguchi, M.; Shima, T.; Yamagishi, T.; Hida, M. Palladium-catalyzed asymmetric allylic alkylation using dimethyl malonate and its derivatives as nucleophile. *Tetrahedron: Asymmetry* 1991, 2, 663-666.
20. A) Gommermann, N.; Koradin, C.; Polbom, K.; Knochel, P. Enantioselective, Copper(I)-Catalyzed Three-Component Reaction for the Preparation of Propargylamines. *Angew. Chem. Int. Ed* 2003, 42, 5763-5766; B) Gommermann, N.; Knochel, P. Practical Highly Enantioselective Synthesis of Propargylamines through a Copper-Catalyzed One-Pot Three-Component Condensation Reaction. *Chem. Eur. J.* 2006, 12, 4380-4392.
21. Peshkov, V. A.; Pereshivko, O. P.; Van der Eycken, E. V. A walk around the A$^3$-coupling. *Chem. Soc. Rev.* 2012, 41, 3790-3807.
22. McCartney, D.; Guiry, P. J. The asymmetric Heck and related reactions. *Chem. Soc. Rev.* 2011, 40, 5122-5150.
23. Marion, N.; Diez-Gonzalez, S.; Nolan, S. P. N-heterocyclic carbenes as organocatalysts *Angew. Chem., Int. Ed.* 2007, 46, 2988-3000.

Example 2

One challenge outlined above centers around isolating the ligand in high enantiomeric excess. The following shows conditions that reproducibly provide the ligand in 98% ee. As can be seen in FIG. 2.1, the racemic ligand 1 can be deracemized by formation of a single diastereomer of complex 3 with chiral palladium complex 2 at 60° C. The development is that decomplexation of 3 to release the ligand 4 in high ee and chemical yield can be achieved under the illustrated conditions. Running the reaction at low temperature is provides 4 in 98% ee that is reproducible. This ligand is configurationally stable and the follow provides an efficient method for its preparation as a single enantiomer (both enantiomers are readily available).

Example 3

Brief Introduction

A new strategy for increasing the barrier to rotation in biaryls has been developed that allows for the incorporation of 5-membered aromatic heterocycles into chiral atropisomers. Using this concept, an imidazole-based biaryl P,N-ligand has been designed and prepared as a single enantiomer. This ligand performs exceptionally well in the enantioselective A$^3$ coupling, demonstrating the potential of this new design element.

Background

The chiral biaryl structural motif is an important component found in a diverse array of catalysts for enantioselective synthesis[1]. Ligands built on the binaphthalene and biphenyl backbone are regularly employed in a variety of reactions with such success that BINAP 1 and BINOL are referred to as privileged ligands[1]. The atropisomeric backbone in the vast majority of chiral biaryl ligands is comprised of substituted or fused benzenoid aromatics that rely on ortho-substitution to hinder rotation about the biaryl bond.[3] Although reducing the steric demand by removing substituents from the 2- or 8-positions lowers the barrier to rotation and hence reduces configurational stability,[4] P,N-ligands such as QUINAP 2[5] and PINAP 3[6] have successfully been prepared and employed in enantioselective transformations.[7,8] It is well-known that changing the dihedral and bite angles of the biaryl can drastically affect ligand performance and the success of 2 and 3 can be attributed to modifying these parameters as well as changing the donating properties of the ligand.[9]

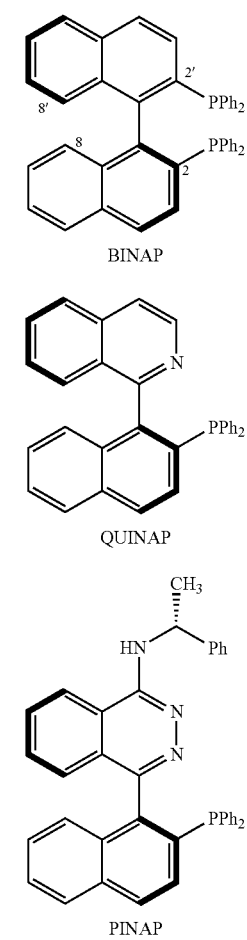

Atropisomeric P,N-ligands have proven to be highly selective,[7] but making structural modifica-tions for fine tuning of the ligand is challenging and relatively few derivatives are known.[8] In contrast to the substituted or fused 6-membered aromatics commonly encountered, 5-membered heteroaromatics would offer a new unexplored chemical diversity and be much easier to prepare and modify using established methods.[10] One potential problem is that ortho-substituents on 5-membered rings are not held as closely in space to the adjacent aromatic group due to the modified bond angles of the ring-system. This may lead to a reduced barrier to rotation and loss of chirality. In his seminal work, Brown encountered this difficulty when 4, an indole version of QUINAP, was prepared and found to not be configurationally stable (FIG. 3.1).[11] While this may potentially be overcome by the incorporation of increasingly large ortho-substituents,[12] the central dogma for inducing atropisomerism, we hypothesized that a fundamental new approach to increasing the barrier to rotation could be developed to enable new classes of highly reactive and selective catalysts. More specifically, we hypothesized that the barrier to rotation in biaryls can be increased by stabilizing the chiral ground state conformation instead of destabilizing the planar transition state leading to racemization (FIG. 3.1). Surprisingly, to the best of our knowledge, this strategy has never been explored. Herein we report our findings in this area including the design, synthesis, deracemization, and successful implementation of a chiral imidazole-based biaryl P,N-ligand for enantioselective copper acetylide addition.

The design of our ligand centers around the in-corporation of a 5-membered electron rich aromatic heterocycle that contains a coordinating atom and functional elements that stabilize the chiral conformation. At the outset we envisioned an imidazole-based system, providing a basic coordination site and a second nitrogen atom that could be appended with a group to stabilize the chiral conformation 7 through π-stacking interactions (FIG. 3.2). This would provide a unique P,N-ligand with modified bite and dihedral angles.

The synthesis of racemic 7 was achieved in several straightforward steps starting with 2-hydroxy-1-naphthaldehyde 8, whereby the requisite heterocycle and phosphino groups were readily introduced (FIG. 3.3). In the event, condensation of 8 with ammonium acetate and benzil furnished 9 in 80% yield[13]. The free alcohol was then protected as the TBS ether and the resulting imidazole alkylated with pentafluorobenzyl bromide to yield 10. The alcohol was then deprotected, converted to the triflate, and coupled[14] to produce rac-7 in ca. 33% overall yield from commercial materials. We were encouraged to find an AB pattern for the benzylic protons in the $^1$H NMR spectrum of rac-7, indicating that they are diastereotopic on the NMR timescale.

With a good source of 7 established, albeit racemic, it seemed prudent to perform a preliminary ligand acceleration effect study. To this end, rac-7 was employed in a copper-catalyzed A$^3$-coupling[15] of butyraldehyde, trimethylsilylacetylene, and dibenzylamine (eq. 1). Much to our delight, amine product 13 was isolated in 97% yield after 24 h at room temperature. Structurally, ligand 7 is significantly different than the known biaryl P,N-ligands such as QUINAP where 13 is obtained in 88% after 120 h[16,6]. Extended reaction times of several days to a week are commonly observed using these ligands.17 With rac-7, the reactivity was enhanced to such an extent that the reaction could even be performed at 0° C., providing 13 in 92% yield after 24 h (eq. 1). This should be advantageous for achieving high selectivities, and attempts were next made to obtain the ligand as a single enantiomer.

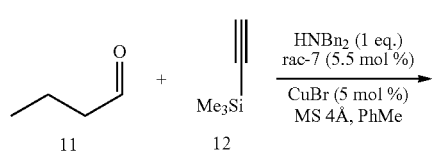

(1)

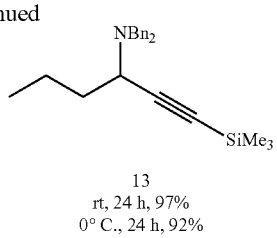

13
rt, 24 h, 97%
0° C., 24 h, 92%

For QUINAP, and derivatives containing only axial chirality, non-racemic material is typically obtained by resolution involving coordination to a chiral Pd-salt, crystallization, and decomplexation[5,11,18]. Unfortunately, this strategy did not provide satisfactory results and 7 could only be obtained in 85-90% ee. Fortunately, instead of resolving 7, after extensive optimization it was found that the racemic compound could be converted to a single enantiomer in a two-step process, in effect deracemizing it. To achieve this, rac-7 was treated with complex 14 and KPF$_6$ in refluxing acetone for 24 h to provide 15 in 81% yield as a single diastereomer whose structure was confirmed by X-ray crystallography (FIG. 3.4)[20]. The free ligand was then obtained in high yield and 98% ee after treatment with dppe.[21]

Interestingly, the inclusion of KPF$_6$ is vital to the success of the reaction as two non-interconverting diastereomers are observed in the absence of this additive. Control experiments were performed to study this issue and an equal mixture of two diastereomers is formed when KPF$_6$ is omitted, but under otherwise identical reaction conditions. Additionally, re-complexation of 7 (98% ee) to 14 results in a single diastereomer that does not revert to the same 1:1 mixture of diastereomers upon heating.

It is important to note that 7 is configurationally stable and samples of the ligand have been stored for several months with no loss of optical purity. One further question regarding the structure involves the role of the C$_6$F$_5$ group and π-stacking. Evidence of π-stacking was obtained early on when X-ray quality single crystals were grown from a sample of rac-7 and the structure solved (FIG. 3.5) The F$_5$-phenyl group is π-stacking with the naphthalene ring at a mean distance of 3.36 Å in a parallel, offset stack.[22] This demonstrates that π-stacking is possible in the solid state, but does not necessarily indicate that it has any influence on the barrier to rotation in solution. Literature protocols used to study π-stacking involve modification of the substitution on one of the aromatic rings.[22] To probe this issue, a comparison of barrier heights between 7 and a compound that would maintain the steric profile but perturb the ability to π-stack was needed. In accord with literature precedent, the corresponding non-fluorinated compound was chosen because if the effect was purely steric, no significant difference would be expected. If π-stacking is indeed involved in the solution phase, a significant difference in barrier height should be observed.

To make the necessary comparisons, 7-H$_5$ was prepared from 8 using the route outlined above.[19] Interestingly, the penultimate non-fluorinated palladium complex 15-H$_5$ was configurationally unstable, and the 1:1 diastereomeric mixture of complexes prepared from racemic 7-H$_5$ converged on a single diastereomer upon standing at room temperature for 24 h. When 7-H$_5$ was liberated from the Pd-complex, it was obtained in 52% ee, a stark contrast to 7 which was isolated in 98% ee. Racemization studies were performed[23] on both 7-H₅ and 7 to obtain their barriers to rotation and it was found that 7-H₅ has a half life of 22 min at 75° C. in DCE whereas 7 has a half-life of 8.70 h.[19] This corresponds to $\Delta\Delta G^{\ddagger}_{75°\,C.}=2.2$ kcal/mol,[19] which is a value that is within the range of previously reported values for π-stacking[22] and demonstrates that the electronic perturbation by simple inclusion of the flourine atoms significantly increases the barrier to rotation.

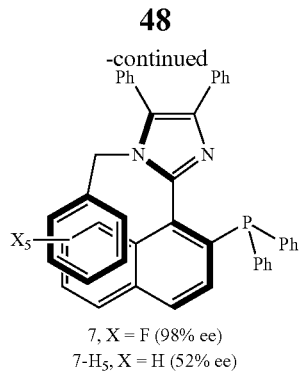

7, X = F (98% ee)
7-H₅, X = H (52% ee)

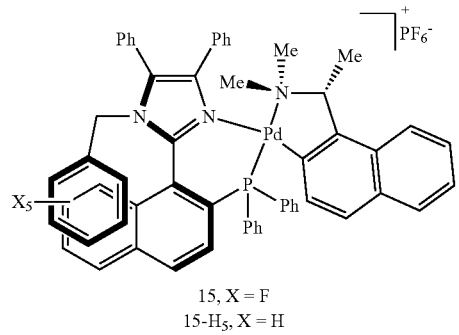

15, X = F
15-H₅, X = H

With this new chiral non-racemic ligand 7 in hand, attention was turned to testing its performance in an enantioselective transformation. To this end, 7 was employed in the enantioselective A³ coupling. As can be seen in Table 3.1, the reactions were highly enantioselective over a range of aldehydes. As might be expected,[15] with aliphatic aldehydes α-substitution increases selectivity (e.g. entry 1 vs. 4). It, is also noteworthy that, using 7, these conditions work well for aromatic aldehydes, which are the most challenging substrates for the reaction.[17] Remarkably, the presence of electron-donating or withdrawing groups have little effect on selectivity (entries 5-9), nor does the reaction temperature. When 16g was allowed to react at 0° C., the reaction was very slow, yielding 17g in only 15% after 4 days, but in 95% ee (entry 8). Increasing the temperature to 22° C. restored the reactivity to an acceptable level (70% yield after 24 h) and had little effect on the ee (entry 9). In comparison, the previous best yield obtained with this electron deficient aldehyde was 43% after 4 days to obtain the product in 63% ee.[17a]

TABLE 3.1

Enantioselective A³-coupling employing 7.[a]

| entry | aldehyde | product | yield (%)[b] | ee (%) |
|---|---|---|---|---|
| 1 | 16a (cyclohexanecarboxaldehyde) | 17a | 95 | 97[c] |
| 2 | 16b (isobutyraldehyde) | 17b | 92 | 95[c] |

TABLE 3.1-continued

Enantioselective A³-coupling employing 7.[a]

| entry | aldehyde | product | yield (%)[b] | ee (%) |
|---|---|---|---|---|
| 3 | 16c | 17c | 94 | 91 |
| 4 | 11 | 13 | 92 | 89[c] |
| 5 | 16d | 17d | 80 | 94[c] |
| 6 | 16e | 17e | 77 | 94[d] |
| 7 | 16f | 17f | 60 | 94[c,d] |
| 8 | 16g | 17g | 15 | 95[c,d] |
| 9 | | | 70 | 92[c,e] |

Carreira has also developed modified conditions to employ the amine 19, which is readily deprotected.[24] With these conditions, using the PINAP ligand, they report that aromatic aldehydes do not provide satisfactory results.[24] In contrast, ligand 7 enables the use of both aliphatic and aromatic aldehydes with high enantioselectivity (FIG. 3.6).

These results lead to the conclusion that 7 is the best ligand for the enantioselective A³-coupling to date, displaying the highest levels of reactivity and selectivity over the broadest range of substrates. More importantly, these results demonstrate the potential of the new design element exemplified by 7.

In summary, we have developed a new concept for increasing the barrier to rotation in biaryls whereby the chiral ground state conformation is stabilized by π-stacking interactions. This strategy was successfully applied to the design of ligand 7, a new chiral biaryl P,N ligand incorporating a 5-membered electron rich heteroaromatic. The ligand is straightforward to prepare and has been demonstrated to be a superb catalyst for the enantioselective A³ coupling reaction. More importantly, this design concept should be broadly applicable and enable a new class of 5-membered heteroaromatic biaryls to be prepared as catalysts for a range of reactions.

REFERENCES 1. (a) Comprehensive Asymmetric Catalysis, Vol. 1-3 (Eds.: E. N. Jacobsen, A. Pfaltz, H. Yamamoto), Springer, Berlin, 1999. (b) Shimizu, H.; Nagasaki, I.; Saito, T. Tetrahedron 2005, 61, 5405-5432; (c) McCarthy, M.; Guiry, P. J. Tetrahedron 2001, 57, 3809-3844.
2. (a) Yoon, T. P.; Jacobsen, E. N. Science 2003, 299, 1691-1693. (b) Qi-Lin Zhou (Ed.), Privileged Chiral Ligands and Catalysts, Wiley-VCH, Weinheim, 2011.
3. (a) Noyori, R.; Takaya, H. Acc. Chem. Res. 1990, 23, 345-350. (b) Berthod, M.; Mignani, G.; Woodward, G.; Lemaire, M. Chem. Rev. 2005, 105, 1801-1836; (c) Brunel, J. M. Chem. Rev. 2005, 105, 857-897; (d) Chen, Y.; Yekta, S.; Yudin, A. K. Chem. Rev. 2003, 103, 3155-3211.
4. Oki, M. Top. Stereochem. 1983, 14, 1-76.
5. (a) Alcock, N. W.; Brown, J. M.; Hulmes, D. I. *Tetrahedron: Asymmetry* 1993, 4, 743-756; (b) Lim, C. W.; Tissot, O.; Mattison, A.; Hooper, M. W.; Brown, J. M.; Cowley, A. R.; Hulmes, D I.; Blacker, A. J. Org. Process Res. Dev. 2003, 7, 379-384.
6. Knopfel, T. F.; Aschwanden, P.; Ichikawa, T.; Watanabe, T.; Carreira, E. M. Angew. Chem., Int. Ed. 2004, 43, 5971-5973.
7. For leading references on enantioseletive hydroboration, see: (a) Carroll, A.; O'Sullivan, T. P.; Guiry, P. J. Adv. Synth. Catal. 2005, 347, 609-631; (b) Doucet, H.; Fernandez, E.; Layzell, T. P.; Brown, J. M. Chem. Eur. J. 1999, 5, 1320-1330; For diboration: (c) Morgan, J. M.; Miller, S. P.; Morken, J. P. J. Am. Chem. Soc. 2003, 125, 8702-8703; For conjugate addition: (d) Fujimori, S.; Knopfel, T. F.; Zarotti, P.; Ichikawa, T.; Boyall, D.; Carreira, E. M. Bull. Chem. Soc. Jpn. 2007, 80, 1635-1657; (e) Knopfel, T. F.; Zarotti, P.; Ichikawa, T.; Carreira, E. M. J. Am. Chem. Soc. 2005, 127, 9682-9683; For [3+2] dipolar cycloaddition: (f) Lim, A. D.; Codelli, J. A.; Reisman, S. E. Chem. Sci., 2013, 4, 650-654; (g) Chen, C.; Li, X.; Schreiber, S. L. J. Am. Chem. Soc. 2003, 125, 10174-10175; For allylic alkylation: (h) Brown, J. M.; Hulmes, D. I.; Guiry, P. J. Tetrahedron 1994, 50, 4493-4506 and references cited therein.
8. (a) Kostas, I. D. Curr. Org. Synth., 2008, 5, 227-249; (b) Guiry, P. J.; Saunders, C. P. Adv. Synth. Catal. 2004, 346, 497-537.
9. (a) Carroll, M. P.; Guiry, P. J.; Brown, J. M. Org. Biomol. Chem., 2013, 11, 4591-4601; (b) Birkholz, M.-N.; Freixa, Z.; van Leeuwen, P. W. N. M. Chem. Soc. Rev. 2009, 38, 1099-1118.
10. Li, J. J. In Name Reactions in Heterocyclic Chemistry; Wiley-VCH: Weinheim, 2004.
11. Claridge, T. D. W.; Long, J. M.; Brown, J. M.; Hibbs, D.; Hursthouse, M. B. Tetrahedron 1997, 53, 4035-4050.
12. There are several reports of 5-membered aromatic chiral biaryl ligands with bulky ortho-substituents. See: (a) Berens, U.; Brown, J. M.; Long, J.; Selke, R. Tetrahedron: Asymmetry 1996, 7, 285-292; (b) Benincori, T.; Brenna, E.; Sannicolò, F.; Trimarco, L.; Antognazza, P.; Cesarotti, E.; Demartin, F.; Pilati, T. J. Org. Chem. 1996, 61, 6244-6251; (c) Benincori, T.; Brenna, E.; Sannicolò, F.; Trimarco, L.; Antognazza, P.; Cesarotti, E.; Zotti, G. J. Organomet. Chem. 1997, 529, 445-453; (d) Benincori, T.; Cesarotti, E.; Piccolo, O.; Sannicolò, F. J. Org. Chem. 2000, 65, 2043-2047; (e) Benincori, T.; Piccolo, O.; Rizzo, S.; Sannicolò, F. J. Org. Chem. 2000, 65, 8340-8347; (f) Andersen, N. G.; Parvez, M.; Keay, B. A. Org. Lett. 2000, 2, 2817-2820; (g) Benincori, T.; Gladiali, S.; Rizzo, S.; Sannicolò, F. J. Org. Chem. 2001, 66, 5940-5942; (h) Figge, A.; Altenbach, H. J.; Brauer, D. J.; Tielmann, P. *Tetrahedron: Asymmetry* 2002, 13, 137-144 for leading references. For a review see: (i) Alkorta, I.; Elguero, J.; Roussel, C.; Vanthuyne, N.; Piras, P. Adv. Heterocycl. Chem. 2012, 105, 1-188.
13. Eseola, A. O.; Obi-Egbedi, N. O Spectrochim. Acta A 2010, 75, 693-701.
14. Kwong, F. Y.; Chan, A. S. C.; Chan, K. S. Tetrahedron 2000, 56, 8893-8899.
15. (a) Peshkov, V. A.; Pereshivko, O. P.; Van der Eycken, E. V. Chem. Soc. Rev. 2012, 41, 3790-3807; (b) Yoo, W.-J.; L. Zhao, L.; Li, C.-J. Aldrichimica Acta 2011, 44, 43-51.
16. Gommermann, N.; Knochel, P. Chem. Commun. 2004, 2324-2325.
17. (a) Gommermann, N.; Koradin, C.; Polbom, K.; Knochel, P. Angew. Chem. Int. Ed. 2003, 42, 5763-5766; (b) Gommermann, N.; Knochel, P. Chem. Eur. J. 2006, 12, 4380-4392.
18. Li, Y.-M.; Kwong, F.-Y.; Yu, W.-Y.; Chan, A. S. C. Coord. Chem. Rev. 2007, 251, 2119-2144.
19. Anderson, N. G. Org. Process Res. Dev. 2005, 9, 800-813.
20. The ee of 7 was measured by HPLC after oxidation to the corresponding phosphine oxide. See SI for detailed information.
21. (a) Meyer, E. A.; Castellano, R. K.; Diederich, F. Angew. Chem., Int. Ed. 2003, 42, 1210-1250; (b) Salonen, L. M.; Ellermann, M.; Diederich, F. Angew. Chem., Int. Ed. 2011, 50, 4808-4842; (c) Gung, B. W.; Xue, X.; Zou, Y. J. Org. Chem. 2007, 72, 2469-2475.
22. Muller, C.; Pidko, E. A.; Staring, A. J. P. M.; Lutz, M.; Spek, A. L.; van Santen, R. A.; Vogt, D. Chem. Eur. J. 2008, 14, 4899-4905.
23. Aschwanden, P.; Stephenson, C. R. J.; Carreira, E. M. *Org. Lett.* 2006, 8, 2437-2440.

Example 4

Ligand 7 from Example 3 above has been named StackPhos and this ligand has been demonstrated to be excellent for enantioselective copper-catalyzed addition of acetylides to quinolinium salts, as seen in Table 4.1 below.

TABLE 4.1

| Entry | Solvent | T [° C.] | t [h] | Yield [b][%] | ee [%] |
|---|---|---|---|---|---|
| 1 | Toluene | rt | 18 | 50 | — |
| 2 | ACN | rt | 18 | 55 | — |
| 3 | DCM | rt | 4 | 92 | — |

TABLE 4.1-continued

| Entry | Solvent | T [° C.] | t [h] | Yield [b][%] | ee [%] |
|---|---|---|---|---|---|
| 4 | DCM | rt | 4 | 90 | 93 |
| 5 | DCM | 0° C. | 18 | 80 | 95 |
| 6 | DCM | −20° C. | 22 | 74 | 98 |

[a] Entries 1-3 were performed with racemic ligand.
[b] Yields of isolated products.
Ligand = StackPhos The scope of the reaction was studied and it was found that the reaction works exceedingly well over a broad range of substrates. Most notably, a variety of alkynes worked in the reaction including aryl, silyl, alkyl, and ester substituted acetylenes. Note the highlighted functional groups in the Table 4.2 below. This is highly useful and it is also noteworthy that with most other ligands, only a single type of alkyne functions well in the reaction. StackPhos is exceptional in this regard with even alkyl-substituted alkynes functioning quite well

TABLE 4.2

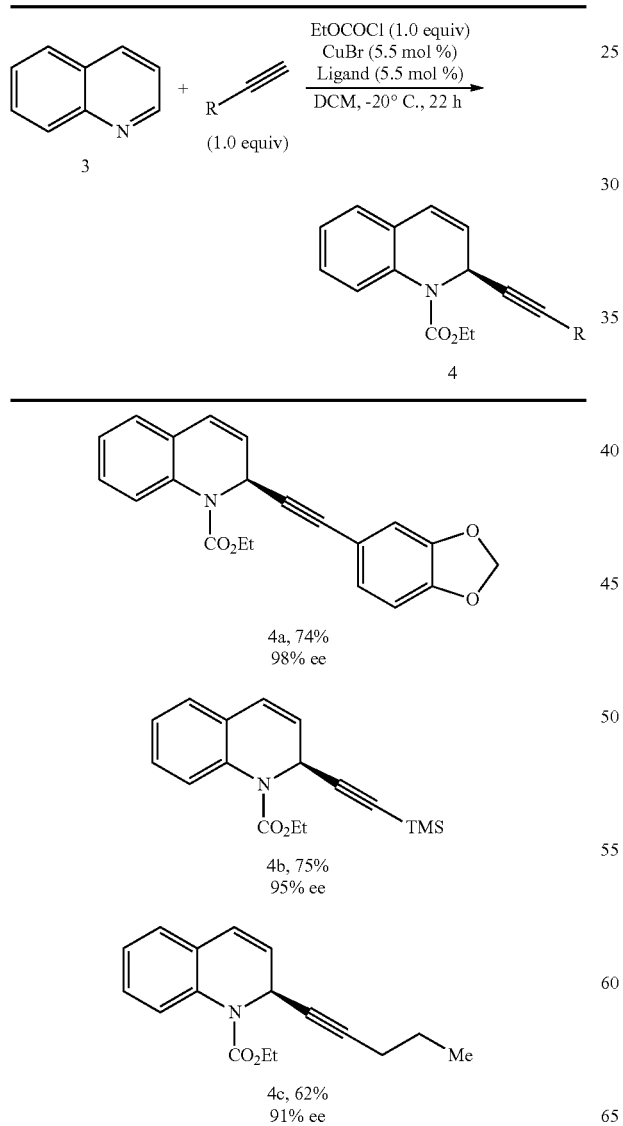

TABLE 4.2-continued

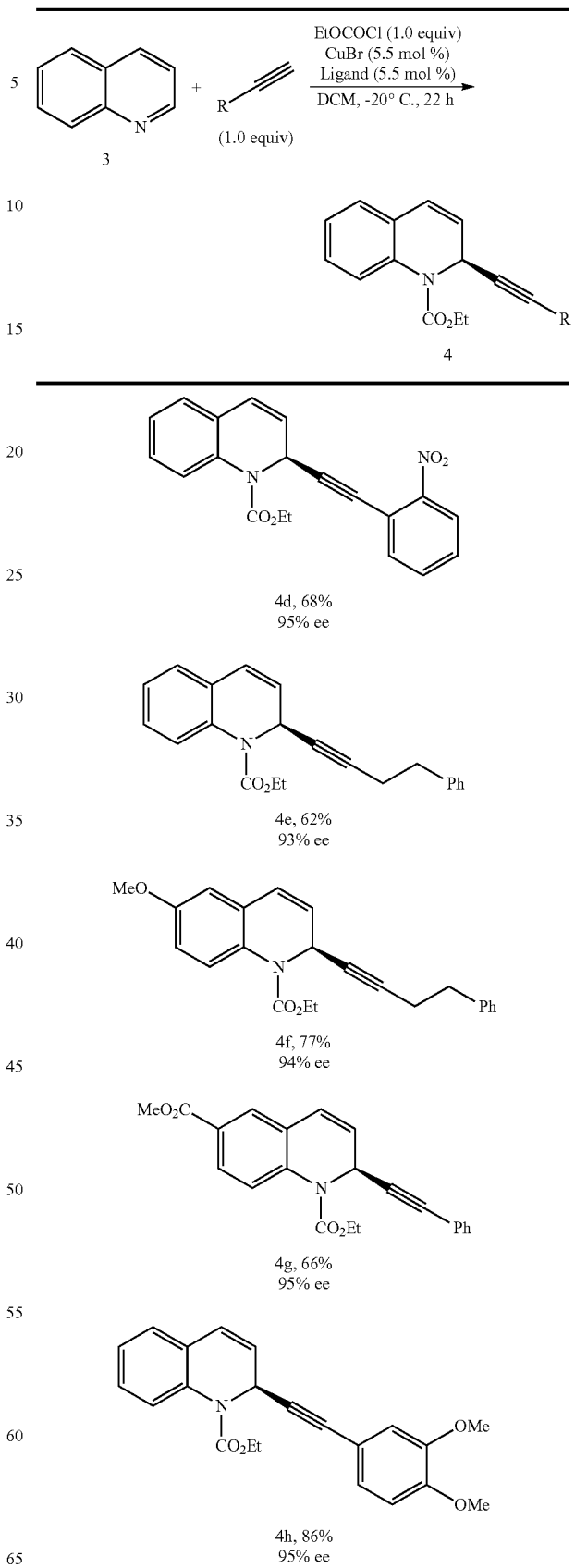

TABLE 4.2-continued

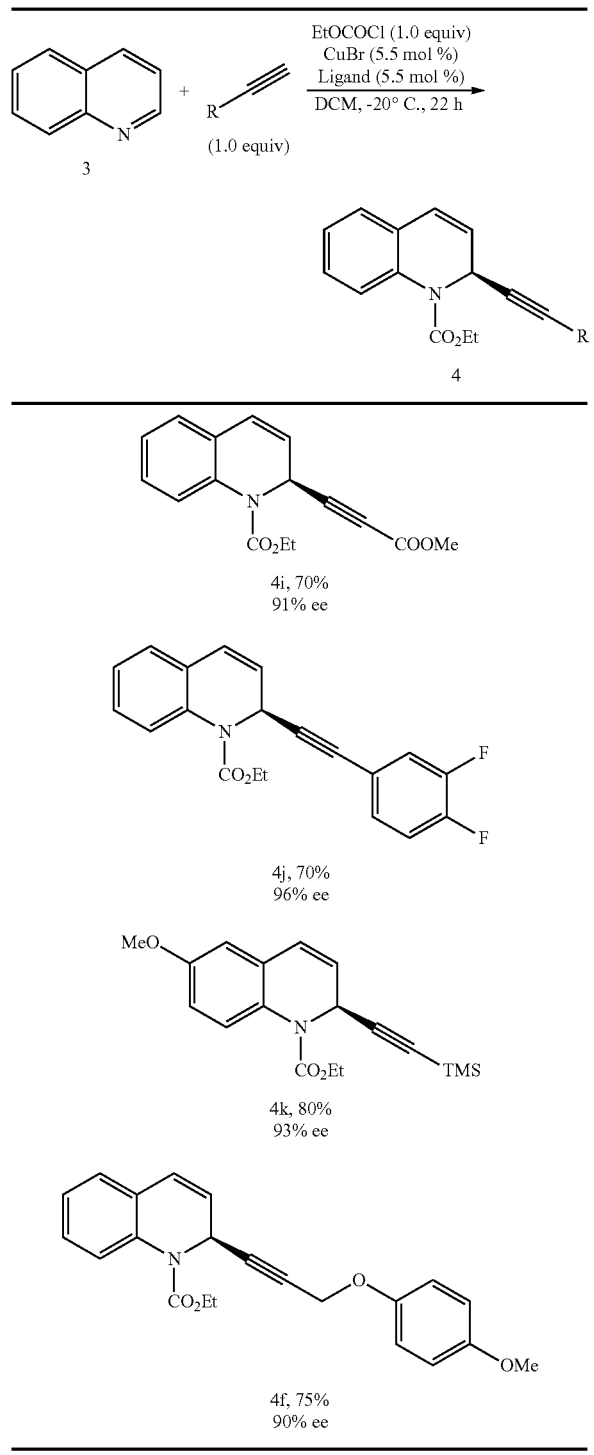

4i, 70%
91% ee 4j, 70%
96% ee 4k, 80%
93% ee 4f, 75%
90% ee

As a demonstration of the methodology and to determine the absolute configuration of the products produced by the specific enantiomer of StackPhos illustrated, three natural products were prepared. As seen in FIG. 4.1, transformation of the products 4a, 4i, and 4j to galipinine, angustureine, and cuspareine was straightforward and produced in high overall yield.

Allylic Alkylation

We have also used the ligand for palladium-catalyzed allylic alkylation, which illustrates that derivatives can be readily prepared in high enantiomeric excess. In this work, we have prepared the ligand (FIG. 4.2), which illustrates the derivative can be produced.

In addition to the ligands shown thus far, we prepared other ligands such as those in FIG. 4.3.

Enantioselective Hydrogenation

StackPhos complexes of palladium and copper for catalysis have prepared and characterized. We have also prepared an Iridium complex: [(StackPhos)Ir(COD)]BPh4 for enantioselective hydrogenation.

Example 5

Brief Introduction:

A new strategy for increasing the barrier to rotation in biaryls is described, and it is demonstrated that arene-arene interactions can contribute to this barrier by stabilization of the chiral conformation. Using this concept, it was found that incorporation of a perfluorinated aromatic provides an increase of ~2 kcal/mol in the barrier to rotation about the biaryl bond. This approach allowed for the inclusion of a 5-membered heterocycle in the biaryl backbone of Stack-Phos, a chiral imidazole-based P,N-ligand. The preparation of this ligand as a single enantiomer and structural analysis of palladium and copper complexes thereof are discussed in detail. These studies establish the advantages of this class of ligands such as a unique mode of coordination in Cu-complexes and a readily prepared biaryl moiety enabled by inclusion of the 5-membered heteroaromatic.

Background:

The development of new chiral ligands is essential for enantioselective catalysis and continues to be an important area at the forefront of organic synthesis.[1] Of particular importance are new ligands that introduce fundamental changes in the chiral backbone and/or unique modes of coordination. Following the seminal reports by Brown and co-workers on QUINAP in 1993,[2] the development of axially chiral P,N-ligands has continued and modified ligands such as Quinazolinap,[3] Pyphos,[4] and PINAP[5] have been demonstrated to perform extremely well in a variety of asymmetric transformations.[6] Recently, we communicated the design and synthesis of StackPhos 5,[7] an imidazole-based P,N ligand that exceled in the $A^3$-coupling reaction.[8]

The design of StackPhos was inspired by the lack of examples of atropisomeric P,N-ligands containing 5-membered heteroaromatics in the backbone, despite the extremely facile synthesis of these moieties and potential for unique ligation properties. This type of ligand has been explored in achiral scaffolds and proved to be a promising class of bidentate ligands. Examples of achiral benzimidazole- (6[9] and 7[10]) and pyrazole-based (8[11]) P,N-ligands have been reported and their function in catalysis demonstrated by application to reactions such as cross-coupling.[12] Interestingly, attempts have been made to render these biaryl ligands chiral. P,N-ligand 9 was prepared by Brown and its resolution attempted, but unfortunately this system is stereochemically labile precluding application in asymmetric catalysis.[13] There is, however, one example of an axially chiral P,N-ligand containing a 5-membered heterocycle-BIMNAP 10.[14] Although 10 is known, there are no reports of its use as a ligand in a catalytic reaction. The fact that no other examples of such P,N-ligands exist is probably related to the challenges of preparing configurationally stable biaryls with smaller ring sizes.[15] As a consequence, such $C_1$-symmetric axially chiral P,N-ligands have not been widely explored in asymmetric catalysis.

In light of this, we decided to address the issue by using a fundamentally different approach to controlling the conformation in axially chiral 5-membered heteroaromatic biaryls, namely ground state stabilization. In fact, the name StackPhos was inspired by the intramolecular π-stacking interactions that contribute to the configurational stability of the chiral biaryl. Herein we report the first studies on controlling the axial chirality of heteroaromatic biaryls by ground state stabilization and detail how using this concept affects the performance of StackPhos, underscoring the practical relevance of this new design element.

Results and Discussion:
System Design

The chiral biaryl motif is present in a myriad of important molecules used in areas as disparate as catalysis and medicine.[1,16] Interestingly, the majority of the axially chiral biaryls are comprised of 6-membered benzenoid or benzo-fused ring systems. In fact, these are the most prevalent chiral biaryls found in both natural[16b] and synthetic systems.[17] There are a number of reasons for this, but one vitally important element of these structures relates to how the molecules are rendered chiral. More specifically, rotation about the aryl-aryl bond is restricted by steric intrusion of ortho-substituents and this is affected by the bond angles of the arene. It follows that the geometrical differences between 6- and 5-membered rings will then alter the distances between the interacting groups of an atropisomer and therefore affect the ease of bond rotation. As illustrated in FIG. 5.3, the larger bond angles between the substituents in a 5-membered ring will result in a less restricted biaryl bond.[15] This is perhaps a contributing factor as to why the vast majority of optically active biaryl atropisomers are comprised of 6-membered rings and 5-membered rings are infrequently encountered.

As these interactions are essential for atropisomerism, the principal, if not only, strategy currently taken to increase the barrier to rotation in biaryls involves the incorporation of bulky ortho substituents to increase the transition state energy. In contrast, we hypothesized that stabilizing the ground state energy would also increase the barrier and this approach should be advantageous because it would remove the requirement for sterically demanding substituents. Surprisingly, to the best of our knowledge, this simple concept has not been explored in the context of 5-membered heteroaromatics or biaryl atropisomerism in general.

To study the feasibility of this idea, a model system comprised of three aromatic units designed to π-stack in an intramolecular fashion was designed. As illustrated in FIG. 5.4, a very simplistic conformational analysis shows the compound in equilibrium between an achiral conformation A and the chiral conformation B. In addition to steric interactions, the position of this equilibrium should be governed by conjugation (favoring A) and attractive arene-arene interactions (favoring B). If stabilizing arene-arene interactions would predominate, the equilibrium could be shifted to the right and favor the chiral conformation. It should also be noted that in chiral biaryls, conjugated conformation A would be the transition state for racemization.

Preliminary Studies

To favor the chiral conformation B, the appropriate arene moieties must be chosen to effect the desired interaction. Perfluoroaromatics are well known to bind strongly to other arenes 18 and, based on these precedents, biaryl 14 was prepared in addition to the non-fluorinated control compound 13.[20] Analysis of the methylene protons Ha and Hb by 1H NMR in each molecule should give insight into the barrier to rotation and to our delight, the methylene group of 13 appeared as broad singlet while 14 exhibited an AB pattern (FIG. 5.5). This behavior is consistent with restricted rotation about the biaryl bond in 14 on the 1H NMR time scale, rendering the methylene protons diastereotopic.

The barriers to rotation of 13 and 14 were then measured using the coalescence method.[21] FIG. 5.6 shows the $^1$H NMR (expanded in the methylene peak region) for compounds 13 and 14 at different temperatures and, as expected, the AB system observed for the methylene peak of 14 gradually coalesced to a broad singlet at elevated temperatures. Upon cooling, the broad singlet observed for 13 gradually separated into an AB system. Careful analysis of the spectra provided a coalescence temperature of 9° C. and 57° C. for 13 and 14, respectively—a remarkable difference. The $\Delta G^\ddagger$ for interconversion of $H_a$ and $H_b$ between the two chemical sites was calculated and the free energies of activation at the coalescence temperatures were found to be 13.7 kcal/mol and 16.1 kcal/mol for compounds 13 and 14, respectively. Comparing the calculated energies for bond rotation in compounds 13 and 14 gives a $\Delta\Delta G^\ddagger$ of 2.4 kcal/mol. By analogy to the previously described models, this energy can be attributed to intramolecular π-stacking interactions[21b] and this value is in agreement with other π-stacking energies involving pentafluoroaromatic moieties.[18] Remarkably, although distal to the biaryl σ-bond, simply perturbing the electronics increased the rotational barrier by nearly 2.5 kcal/mol.

Further evidence of π-stacking was obtained after X-ray quality single crystals of 14 were obtained and analyzed (FIG. 5.7). Unfortunately, compound 13 is a viscous oil, precluding further direct comparison. In the solid state, the arene-arene interaction in 14 appears to occur in the parallel-displaced arrangement.[18] The two aromatic groups are parallel to each other with the benzyl arene centered over the edge of the naphthalene. The dihedral angle that defines the planes of the A- and B-rings is 880 and the A- and C-rings have an interplane distance of 3.26 Å, which is the distance between the averaged planes of the two slightly canted aromatics. Interestingly, this is closer than the interplane distance of 3.4 Å found in the well-known $C_6H_6$ and $C_6F_6$ co-crystal,[22] likely due to constraints imparted by the C—N bond length in this intramolecular interaction. There are also intermolecular π-stacking interactions between alternating naphthalene and pentafluorobenzene rings in the solid state (FIG. 5.7).

While these results provide a proof-of-principle demonstration that arene-arene interactions can indeed function as desired, it was important to understand how electronic and steric factors affect the system before moving from model compounds to functional molecules. To this end, the influence of substituents on the naphthalene were briefly studied with the hope that the barrier could be increased to the point where atropisomerism may be possible. Biaryl 15 was prepared with the intention of adding an electron-donating methoxy group to enhance the interaction between the electron-rich naphthalene ring and an electron-poor pentafluorobenzyl group. Based on the X-ray structure of 14, substitution at 5-position of the naphthalene should directly increase the electron density, but surprisingly, the barrier to rotation in 15 was very similar to compound 14 ($\Delta G^\ddagger$=16.3 kcal/mol and $T_c$=61° C.) suggesting that the pentafluorobenzyl moiety dominates the interaction regardless of the nature of the naphthalene ring (FIG. 5.8). Gung and co-workers observed the same trend when studying π-stacking interactions involving strongly electron deficient aromatic rings.[23]

Positioning a methoxy group ortho to the biaryl bond presented a very high barrier to rotation in 16, even in the absence of the pentafluorophenyl group. The $^1$H NMR spectrum of this compound in C2D2Cl4[24] exhibited an AB system that did not coalesce at 120° C. and the barrier could not be determined.[25] The isoquinoline derivative 17, on the other hand, exhibited a very low barrier to rotation that also could not be determined by the coalescence method.[25] These results clearly demonstrate that sterics are also important, with groups as small as hydrogen significantly contributing to the barrier to rotation.

Although 17 exhibited an extremely low barrier, the indole 18 was prepared for comparison to 14 (FIG. 5.9). Surprisingly, the coalescence temperature and the barrier to rotation increased considerably by changing the B-ring to an indole (from 16.1 to 17.3 kcal/mol). These data show that the nature of the heterocycle affects the barrier to rotation of these compounds and suggests that a "buttressing effect" might be playing a role.[26] To further investigate this rationale, a 5-substituted pyrrole that maintained the π-system but altered the sterics was prepared (FIG. 5.9). As expected, the barrier to rotation increased to 16.5 kcal/mol. While this change is not of the same magnitude as changing to the indole, it demonstrated that substitution at this position could prove to be important for increasing the barrier.

Further modifications were made to probe the influence of substituents on the benzyl group. As can be seen in FIG. 5.9, while the perfluoro derivative 18 had a substantially higher barrier than the des-fluoro analog 20, no significant difference was observed between any of the other compounds, including the mono-fluoro derivative 21. These data were somewhat unexpected, underscoring the complexity of the system.

The information gleaned from the model studies was quite instructive and could be used to increase the barrier in functional molecules as follows. Firstly, the highest barrier to rotation observed was 17.3 kcal/mol. It is important to note that, by definition,[27] an atropisomer has a barrier of at least ~22 kcal/mol at room temperature, so a combination of sterics and electronics will likely be necessary to increase the barrier to at least this level and, for all practical purposes, higher. When appending a group to induce stabilizing arene-arene interactions, the pentafluorophenyl benzyl group is a good choice because it obviates the need for changing the electronics of the naphthalene ring by substitution. These studies showed that by including this moiety, an increase of at least 2 kcal/mol can be achieved. Finally, inclusion of a group ortho to the benzyl group on the heterocycle, while removed from the arene-arene interaction, can actually increase the barrier to rotation (as in 18 and 19). These energetic contributions can be crucial when developing new ligands for asymmetric catalysis. Indeed, our recent report demonstrated that an extra 2.2 kcal/mol of stabilization was essential vide infra.[7]

Ligand Design

StackPhos (5, FIG. 5.1), a 5-membered heterocyclic biaryl, was designed to include the important structural elements identified above to increase the barrier to rotation, rendering it chiral. With the goal of producing an atropisomeric P,N-ligand, it was decided that a phosphine-substituted naphthalene moiety and a 5-membered heterocycle containing a basic nitrogen would be incorporated for coordination. The nitrogen heterocycle would be an imidazole to permit both coordination and facile incorporation of a pentafluorophenyl group for π-stacking. Furthermore, this group was predicted to obviate the need for substitution of the naphthalene ring as described above, allowing it to retain the same elements as successful ligands such as BINAP, QUINAP, etc. The choice of imidazole also was thought to be advantageous because a substituent at the 5-position could be introduced to enforce a buttressing effect and raise the barrier to rotation. Other potentially attractive salient features were the ability to include substituents in the 4-position to protrude into the space defining the ligand's chiral binding pocket and a facile heterocycle synthesis by condensation. As described previously, preparation of racemic StackPhos was achieved from readily available starting materials in 33% overall yield.[7] Evidence that the design elements established by the studies described above influenced the barrier to rotation was obtained by measuring $\Delta\Delta G^\ddagger_{75°C.}$=2.2 kcal/mol between StackPhos and the des-fluoro analog as well as X-ray crystallography.[7] The experimental barrier to rotation of StackPhos was observed to be 28.4 kcal/mol,[7] and hence it is atropisomeric. For catalysis, a single enantiomer was needed and this proved to be extremely challenging; however, the design of the ligand proved to be quite uniquely advantageous and the ligand was prepared as a single enantiomer through a novel deracemization process, which is described in full detail below.

Deracemization of the P,N-Ligand

The resolution of axially chiral P,N-ligands usually requires the use of a chiral palladium complex dimer such as 24 (for structure, see FIG. 5.11).[2,28] Upon complexation of the P,N-ligand with 24, a 1:1 mixture of diastereomers is formed and separated by fractional crystallization. After decomplexation of the chiral palladium moiety, a single enantiomer of the ligand is obtained. This method works exceedingly well over a wide range of axially chiral P,N-ligands.[29] To this end, we performed an experiment at ambient temperature in acetone in which the racemic ligand rac-5 and the palladium dimer 24 were mixed in the presence of potassium hexafluorophosphate, and a 1:1 mixture of diastereomers 25 and 26 was observed (FIG. 5.10). This equimolar mixture was isolated and fractional crystallization was attempted, however, after extensively screening conditions this method proved to be unsuccessful. Interestingly, during attempts to optimize this separation process, it was realized that the ratio of diastereomers would slightly change and this was seemingly not due to a fractional crystallization. This observation was made when conditions at higher temperatures were employed and this suggested that it may be possible to interconvert the two diastereomers. Brown's indole-based P,N-ligand 9 (FIG. 5.2) readily gives a single diastereomer when treated with chiral palladium complex 24 at room temperature,[13] but QUINAP complexes do not interconvert even at elevated temperatures.[28] Based on this data, we were encouraged to heat the diastereomeric mixture to possibly equilibrate the system to a single diastereomer, although this would rely on a significant energy difference between 25 and 26.

To probe this, a 1:1 mixture of diastereomers 25/26 in acetone was heated at 60° C. for 24 h. To our delight, a single diastereomer was observed as judged by $^1$H NMR. To evaluate the practicality of this process, the experiment was performed on a larger scale by mixing racemic phosphine 5 with palladium complex 24 and KPF$_6$ in acetone. After refluxing the mixture for 24 hours the solution was filtered off, the solvent removed, and a single diastereomer was observed in the NMR of the crude reaction mixture. A single recrystallization gives the pure diastereomer 25 in 81% yield (FIG. 5.10). As both enantiomers of 24 are available, this process allows the rapid conversion of racemic ligand to a single enantiomer of 25, without the classical problem of losing 50% of the material during a kinetic resolution process.

Interestingly, this equilibration process was fairly demanding and required that the chiral amine resolving agent 24 contained the naphthalene substituent. Attempts were made to utilize the phenyl substituted palladium complex 27 but resulted in only a 1:1 mixture of diastereomers under the equilibrating conditions described above (FIG. 5.11). Brown also observed the requirement for the naphthalene while studying palladium complexes formed from QUINAP.[2,30] Resolution of QUINAP employing complex 24 was achieved with success whereas 27 did not generate separable palladium complexes. It's believed that the fused benzene ring changes the conformational requirements, and consequently, a greater difference in energy for the pair of diastereomers is observed making the fractional crystallization more facile using the naphthalene-based system.[30] With complex 28, the 5-membered palladacycle in the auxiliary must allow the benzylic methyl group more degrees of freedom, diminishing the energy difference between the diastereomers. In 25/26, the benzylic methyl groups likely have a greater conformational constraint through interaction with the peri H of the naphthalene resulting in a larger energy difference between diastereomers.

As the deracemization phenomenon is unique to this imidazole-based P,N-ligand system, it seemed prudent to gain a more thorough understanding of the important factors involved. The structural differences responsible for the difference in stability between the two diastereomers 25 and 26 were probed using X-ray crystallography when single crystals of an equimolar mixture of 25 and 26 were obtained and the structure solved. The X-ray structure of the crystals revealed a 1:1 packing of the two diastereomers (FIG. 5.12) and allowed for a conformational analysis to provide insight into the crucial steric interactions responsible for the difference in energy. For clarity, the crystal structures of each diastereomer are depicted separately in FIG. 5.13. The most striking difference between the two structures is the conformation of the 5-membered palladacycle. In the more stable isomer 25 it has adopted an "envelope" conformation whereas it is "flattened" in 26. This planarity likely introduces strain to the system, raising its energy and thereby favoring diastereomer 25 under equilibrating conditions.

Analysis of StackPhos and complexes thereof With a good source of 25 in hand, the overall goal was to obtain StackPhos 5 in high ee for use as a ligand for asymmetric catalysis; however, the structural features of ligand metal complexes such as 25 are also of interest as they may provide later insight into catalytic reactions.[31] To this end, as described above, 25 was isolated as a single diastereomer and crystallized to obtain a separate X-ray structure in the absence of 26 (FIG. 5.14). Interestingly, in the solid state, the pentafluorobenzyl group of 25 is pointed away from the naphthalene ring instead of interacting with this moiety through the predicted arene-arene observed in the crystal structure of the free ligand StackPhos 5.[7] Instead, the fluorinated aromatic ring is π-stacking with the phenyl group in the 5-position of the imidazole. A possible explanation for this is that the small dihedral angle observed in the biaryl moiety (54.3°) is required to bind to the metal in a bidentate fashion. Consequently, to accommodate this the pentafluorophenyl must rotate away from the naphthalene moiety to avoid repulsive steric interactions. In other words, upon complex formation, bond rotation decreases the dihedral angle preventing the π-stacking interaction observed in the free phosphine.[7] In the case of the free StackPhos, a much larger dihedral angle is observed (84.9°) allowing for what must be a more highly stabilizing arene-arene interaction with the naphthalene.[7]

The motivation for this work was to provide a new type of heterocyclic P,N-ligand that moves from a 6-membered aryl moiety to a 5-membered heteroaromatic. At the outset we thought that this would be advantageous for a number of reasons related to ease of synthesis and tuning of the ligand, but the shift to a 5-membered ring would likely also have profound effects on the structures of complexes of StackPhos and presumably also catalysts thereof. For comparison to a 6-membered heterocyclic P,N-ligand, the X-ray crystal structure of palladium complex 25 was analyzed and compared to the analogous QUINAP complex 29.[30] The structures are displayed in FIG. 5.10 and have the same stereochemistry with respect to both the atropisomer and the resolving agent. The dihedral angles θ and bite angles φ are listed for both structures. Although the bite angle φ is slightly smaller in 25, the dihedral angle θ is significantly smaller (>10° difference) probably due to the smaller 5-membered imidazole ring. The chiral environment around the metal center in both P,N-ligands are shown with space filling structures. The selected views illustrate that a significant difference in the steric profile of the complexes is present, which both originates from and is most pronounced in the region about the imidazole moiety. Interestingly, the phenyl group at the 4-position of this 5-membered heterocycle helps to generate a bulky chiral environment reminiscent of BINAP.[32] Decomplexation and release of a single enantiomer of StackPhos With a good synthesis of a single diastereomer of 25 in hand, what remained was to isolate free StackPhos by decomplexation. With the demonstration of the stereochemical lability of 25, albeit at elevated temperatures, isolating StackPhos without erosion of the ee was of concern with the potential for this problem to originate either by epimerization or racemization at the complex or free ligand stages respectively. While most axially chiral P,N-ligands have a high barrier that prevents racemization,[28,33] for StackPhos this was initially an unknown and a careful analysis of the enantiomeric excess of free ligand would be needed after decomplexation. Unfortunately, all attempts to analyze the ee of rac-5 by HPLC using a chiral stationary phase were unsuccessful; however, after oxidation of rac-5 to the corresponding phosphine oxide a baseline separation was observed.[34,35]

To isolate free StackPhos, decomplexation was effected by reaction of ent-25 with one equivalent of dppe.[36] This enantiomer of 25 was utilized so that direct comparison to known copper complexes could be made vide infra. The initial experiments were conducted at ambient temperature in dichloromethane and 5 was recovered in high yield after column chromatography (Table 5.1, Entry 1). Surprisingly, the enantiomeric excess of StackPhos 5 ranged from 88 to 92% with these conditions and clearly this procedure needed improvement.

TABLE 5.1

Optimization of the decomplexation reaction.[a]

[Structure of ent-25 complex with dppe, DCM, 1 h arrow to structure 5]

| Entry | Temp (° C.) | yield (%) | ee (%) |
|---|---|---|---|
| 1 | 22 | 90-100 | 88-92 |
| 2 | 0 | 95 | 90 |
| 3 | −78 | no reaction | — |
| 4 | −78to0 | 97 | 98 |

[a]The ee was determined by HPLC after oxidation to the phosphine oxide.

At this stage is was unclear whether the low ee material was a result of having small amounts of the minor diastereomer (ent-26) present in the starting complex, if ent-26 was being formed under the conditions, or even if StackPhos may be epimerizing to a small extent. Despite this uncertainty, reducing the temperature could potentially improve the optical purity if the problem was a small loss of ee during the decomplexation process. Interestingly, at 0° C., no improvement was observed in terms of yield or enantiomeric excess and at −78° C. there was no reaction due to low solubility of dppe in $CH_2Cl_2$ using a solid addition protocol (Table 5.1, entries 2 and 3). Fortunately, it was found that adding solid dppe to a solution of 25 at −78° C. and warming the mixture to 0° C. would release the ligand in 98% enantiomeric excess after one hour. The absolute stereochemistry of StackPhos was determined by X-ray crystallography of palladium complex 25 with known absolute configuration.[36] StackPhos as a ligand for enantioselective catalysis In our previous communication, it was shown that StackPhos was an excellent ligand for the enantioselective $A^3$-coupling reaction, furnishing the propargylamine products 32 in high yields and enantioselectivities over a broad range of substrates, including alkyl and aryl aldehydes (FIG. 5.15).[7] With StackPhos, the catalyst formed in situ exhibited a much greater reactivity and allowed for the use of electron deficient aldehydes and overcoming the limitations in scope associated with QUINAP, the benchmark ligand for this reaction.[37] Since the reactions were faster and could be performed at 0° C., this improvement in reactivity prompted us to study a 5.CuBr complex to glean insight into the factors responsible.

Fortunately, using enantiomerically pure StackPhos and CuBr, X-ray quality single crystals could be grown and the structure was solved. Interestingly, this analysis revealed the structure to be a dimeric complex $[CuBr\{(S)\text{-}5\}]_2$ 34 which greatly differed from that of the QUINAP.CuBr complex 33.[38,39] With StackPhos, the two P,N-ligands present in 34 are clearly different with one coordinating in a bidentate fashion and the other monodentate. Interestingly, the bidentate P,N-ligand is coordinated to two different copper atoms that are bridged with a bromine atom, forming an eight-membered ring (FIGS. 5.16A-5.16C).[40] The formation of this large ring allows for a dihedral angle of 89.9° in the biaryl moiety. Consequently, the intramolecular π-stacking interaction between the pentafluorobenzyl moiety and naphthalene is feasible because this type of coordination does not force unfavorable steric interaction between the two arene moieties. Interestingly, the monodentate P,N-ligand is also stacking and the dihedral angle is 78.4°.

Although this structural information comes from the solid state, it implies that formation of a more traditional bidentate complex between StackPhos and CuBr may be unfavorable. In solution, by analogy to QUINAP complex 33, the analogous structure 35 was hypothesized to potentially explain greater reactivity. If StackPhos is monodenatate, this may provide for a more accessible metal center with the solid state structure 34 being produced by coordination of an imidazole nitrogen of 35 to copper and displacement of a bromine atom as shown below. By changing the 6-membered isoquinoline heterocycle to the 5-membered imidazole present in StackPhos, the mode of coordination is greatly influenced. In this setting, it provides an enhancement in reaction rate providing the products in high ee. This demonstrates that the incorporation of 5-membered heterocycles into the chiral biaryl backbone can be enormously beneficial and provide enhancements to catalysis that are inaccessible by maintaining the 6-membered arene biaryl motif.

In summary, the studies described here detail a new strategy to increase the barrier to rotation in biaryl atropisomers. Model studies demonstrate that by simply including aromatics that form stabilizing arene-arene interactions, the barrier to rotation can be increased by ~2 kcal/mol. Incorporation of this simple design element should be applicable to a wide variety of biaryls, enabling an increase in barrier without the need to increase steric demand about the biaryl bond. The present study describes how utilizing this concept enabled the incorporation of an imidazole, a 5-membered heteroaromatic arene, into StackPhos, a new chiral biaryl P,N-ligand. Interestingly, this ligand π-stacks in the originally anticipated mode in the free ligand, but the interaction is replaced by a different arene-arene interaction upon forming palladium complex 25. This is extremely fortuitous as it then permits a unique deracemization process novel amongst this class of ligands. After decomplexation, the stabilizing arene-arene interaction between the pentafluorobenzyl and naphthyl moieties is reformed to provide StackPhos as a configurationally stable ligand.

Complexes of StackPhos with palladium and copper were prepared and structural comparison is made to complexes of the highly successful ligand QUINAP to probe the differences between 5- and 6-membered heteroaromatics. Interestingly, these data suggest that the imidazole plays an important role in defining the chiral space through its substituents and by changing the dihedral angle required for bidentate coordination. These influences appear to be extremely important and significantly different than known ligands.

From a broader perspective, this previously unexplored class of ligands should provide a unique, highly tunable scaffold for the development of new chiral ligands and catalysts for enantioselective reactions. The expansion of this new design element to the synthesis of additional new ligands and catalysts has emerged in our group in combination with the investigation of new enantioselective reactions enabled by these ligands.

REFERENCES 1. (a) Comprehensive Asymmetric Catalysis, Vol. 1-3 (Eds.: E. N. Jacobsen, A. Pfaltz, H. Yamamoto), Springer, Berlin, 1999. (b) Qi-Lin Zhou (Ed.), Privileged Chiral Ligands and Catalysts, Wiley-VCH, Weinheim, 2011.
2. Alcock, N. W.; Brown, J. M.; Hulmes, D. I. *Tetrahedron: Asymmetry* 1993, 4, 743-756.
3. (a) McCarthy, M.; Goddard, R.; Guiry, P. J. *Tetrahedron: Asymmetry* 1999, 10, 2797-2807. (b) Connolly, D. J.; Lacey, P. M.; McCarthy, M.; Saunders, C. P.; Carroll, A.-M.; Goddard, R.; Guiry, P. *J. J. Org. Chem.* 2004, 69, 6572.
4. Kwong, F. Y.; Chan, A. S. C.; Chan, K. S. *Tetrahedron* 2000, 56, 8893-8899.
5. Knopfel, T. F.; Aschwanden, P.; Ichikawa, T.; Watanabe, T.; Carreira, E. M. Angew. Chem., Int. Ed. 2004, 43, 5971-5973.
6. Fernández, E.; Guiry, P J.; Connole, K. P. T.; Brown, J. M. *J. Org. Chem.* 2014, 79, 5391-5400.
7. Cardoso, F. S. P.; Abboud, K. A.; Aponick, A. *J. Am. Chem. Soc.,* 2013, 135, 14548-14551.
8. (a) Peshkov, V. A.; Pereshivko, O. P.; Van der Eycken, E. V. *Chem. Soc. Rev.* 2012, 41, 3790-3807. (b) Yoo, W.-J.; L. Zhao, L.; Li, C.-J. *Aldrichim. Acta* 2011, 44, 43-51.
9. Chung, K. H.; So, C. M.; Wong, S. M.; Luk, C. H.; Zhou, Z.; Lau, C. P.; Kwong, F. Y. *Chem. Commun.* 2012, 48, 1967-1969.
10. Song, B.; Knauber, T.; Gooßen, L. J. *Angew. Chem., Int. Ed.* 2013, 52, 2954-2958.
11. Singer, R. A.; Caron, S.; McDermott, R. E.; Arpin, P.; Do, N. M. *Synthesis* 2003,11, 1727-1731.
12. (a) Fromm, A.; van Wüllen, C.; Hackenberger, D.; Gooßen, L. *J. Am. Chem. Soc.,* 2014, 136, 10007-10023. (b) Wong, S. M.; So, C. M.; Chung, K. H.; Lau, C. P.; Kwong, F. Y. *Eur. J. Org. Chem.* 2012, 4172-4177.
13. Claridge, T. D. W.; Long, J. M.; Brown, J. M.; Hibbs, D.; Hursthouse, M. B. *Tetrahedron* 1997, 53, 4035-4050.
14. Figge, A., Altenbach, H. J., Brauerb, D. J., Tielmannc, P. *Tetrahedron: Asymmetry* 2002, 13, 137-144.
15. Alkorta, I.; Elguero, J.; Roussel, C.; Vanthuyne, N.; Piras, P. Atropisomerism and Axial Chirality in Heteroaromatic Compounds. *Adv. Heterocycl. Chem.* 2012, 105, 1-188.
16. (a) Clayden, J.; Moran, W. J.; Edwards, P. J.; LaPante S. R. *Angew. Chem. Int. Ed.* 2009, 48, 6398. (b) Bringmann, G.; Gulder, T.; Gulder, T. A. M.; Breuning, M. *Chem. Rev.* 2011, 111, 563-639.
17. Bringmann, G.; Price Mortimer, A. J.; Keller, P. A.; Gresser, M. J.; Garner, J.; Breuning, M. *Angew. Chem., Int. Ed.* 2005, 44, 5384-5427.
18. (a) Meyer, E. A., Castellano, R. K.; Diederich, F. *Angew. Chem., Int. Ed* 2003, 42, 1210-1250. (b) Salonen, L. M., Ellermann, M., Diederich, F. *Angew. Chem., Int. Ed.* 2011, 50, 4808-4842.
19. Intentionally skipped
20. Ohkubo, M.; Hayashi, D.; Oikawa, D.; Fukuhara, K.; Okamoto, S.; Sato, F. *Tetrahedron Lett.* 2006, 47, 6209-6212.
21. (a) O. Sutherland, *Annu. Rep. NMR Spectrosc.,* 1971, 4, 71. (b) Mati, I. K.; Cockroft, S. L. *Chem. Soc. Rev.* 2010, 39, 4195-4205.
22. (a) Patrick, R.; Prosser, G. S. *Nature* 1960, 187, 1021. (b) Williams, J. H.; Cockcroft, J. K.; Fitch, A. N. *Angew. Chem., Int. Ed. Engl.* 1992, 31, 1655-1657.
23. Gung, B. W.; Xue, X. W.; Zou, Y. *J. Org. Chem.* 2007, 72, 2469-2475.
24. For a matter of comparison, the barrier to rotation of 20 in $C_2D_2Cl_4$ and $CDCl_3$ were measured and it was observed that they are comparable when using these solvents.
25. The practical range for barriers determined using the coalescence method is defined by the temperature limitations of the NMR probe.
26. (a) Bott, G.; Field, L.-D.; Sternhell, S. *J. Am. Chem. Soc.* 1980, 102, 5618-5626. (b) Rieger, M.; Westheimer, F. H. *J. Am. Chem. Soc.* 1950, 72, 19-28.
27. Oki, M. *Top. Stereochem.* 1983, 14, 1-76.
28. Lim, C. W.; Tissot, O.; Mattison, A.; Hooper, M. W.; Brown, J. M.; Cowley, A. R; Hulmes, D I.; Blacker, A. J. *Org. Process Res. Dev.* 2003, 7, 379-384.
29. Li, Y.-M.; Kwong, F.-Y.; Yu, W.-Y.; Chan, A. S. C. *Coord. Chem. Rev.* 2007, 251, 2119-2144.
30. Alcock, N. W.; Hulmes, D. I.; Brown, J. M. *J. Chem. Soc., Chem. Commun.* 1995, 395-397.
31. (a) Carroll, M. P.; Guiry, P. J.; Brown, J. M. *Org. Biomol. Chem.* 2013, 11, 4591-4601. (b) Birkholz, M.-N.; Freixa, Z.; van Leeuwen, P. W. N. M. *Chem. Soc. Rev.* 2009, 38, 1099-1118.
32. Noyori, R.; Takaya, H. *Acc. Chem. Res.* 1990, 23, 345-350.
33. (a) Guiry, P. J.; Saunders, C. P. *Adv. Synth. Catal.* 2004, 346, 497-537. (b) Carroll, M. P.; Guiry, P. J. *Chem. Soc. Rev.* 2014, 43, 819.
34. For separation of racemic phosphine oxide in a P,N-ligand see: Kwong, F. Y.; Yang, Q.; Mak, T. C. W.; Chan, A. S. C.; Chan, K. S. *J. Org. Chem.* 2002, 67, 2769-2777.
35. This oxidation was performed in quantitative yield using hydrogen peroxide in dichloromethane and was performed in an analytical fashion. For full details, see ref 7.
36. The palladium complex ent-25 was prepared analogously to 25 as shown in Scheme 3.
37. (a) Gommermann, N.; Koradin, C.; Polbom, K.; Knochel, P. *Angew. Chem. Int. Ed.* 2003, 42, 5763-5766. (b) Gommermann, N.; Knochel, P. *Chem. Eur. J.* 2006, 12, 4380-4392.
38. Koradin, C.; Gommermann, N.; Polbom, K.; Knochel, P. *Chem. Eur. J.* 2003, 9, 2797-2811.
39. For a similar complex, Quinazolinap-CuCl, see: Fleming, W. J.; Muller-Bunz, H.; Lillo, V.; Fernandez, E.; Guiry, P. J. *Org. Biomol. Chem.* 2009, 7, 2520-2524.
40. For an example of a bidentate ligand bridging two coppers, see: Shishkov, I. V.; Rominger, F.; Hofmann, P. *Dalton Trans.* 2009, 1428-1435.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the measurement technique and the type of numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

The invention claimed is:

1. A method of making a biaryl compound, comprising:

wherein the biaryl product has the following structure:

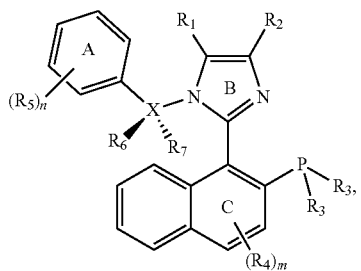

wherein each of the $R_5$ groups is independently selected from the group consisting of: hydrogen, a halogen group, a 3 to 10 carbon atom cyclic alkyl group, a 1 to 20 carbon atom linear alkyl group, an aryl group, a —OR group, a —SR group, a —SiR$_{(3)}$ group, a NR$_{(2)}$ cyclic group, and a NR$_{(2)}$ linear group, wherein each R is independently selected from the group consisting of: hydrogen, a 3 to 10 carbon atom cyclic alkyl group, a 1 to 20 carbon atom linear alkyl group, and an aryl group, wherein n is 1 to 5, wherein X is C or S, wherein each $R_6$ and $R_7$ group is independently selected from the group consisting of: hydrogen, a 3 to 10

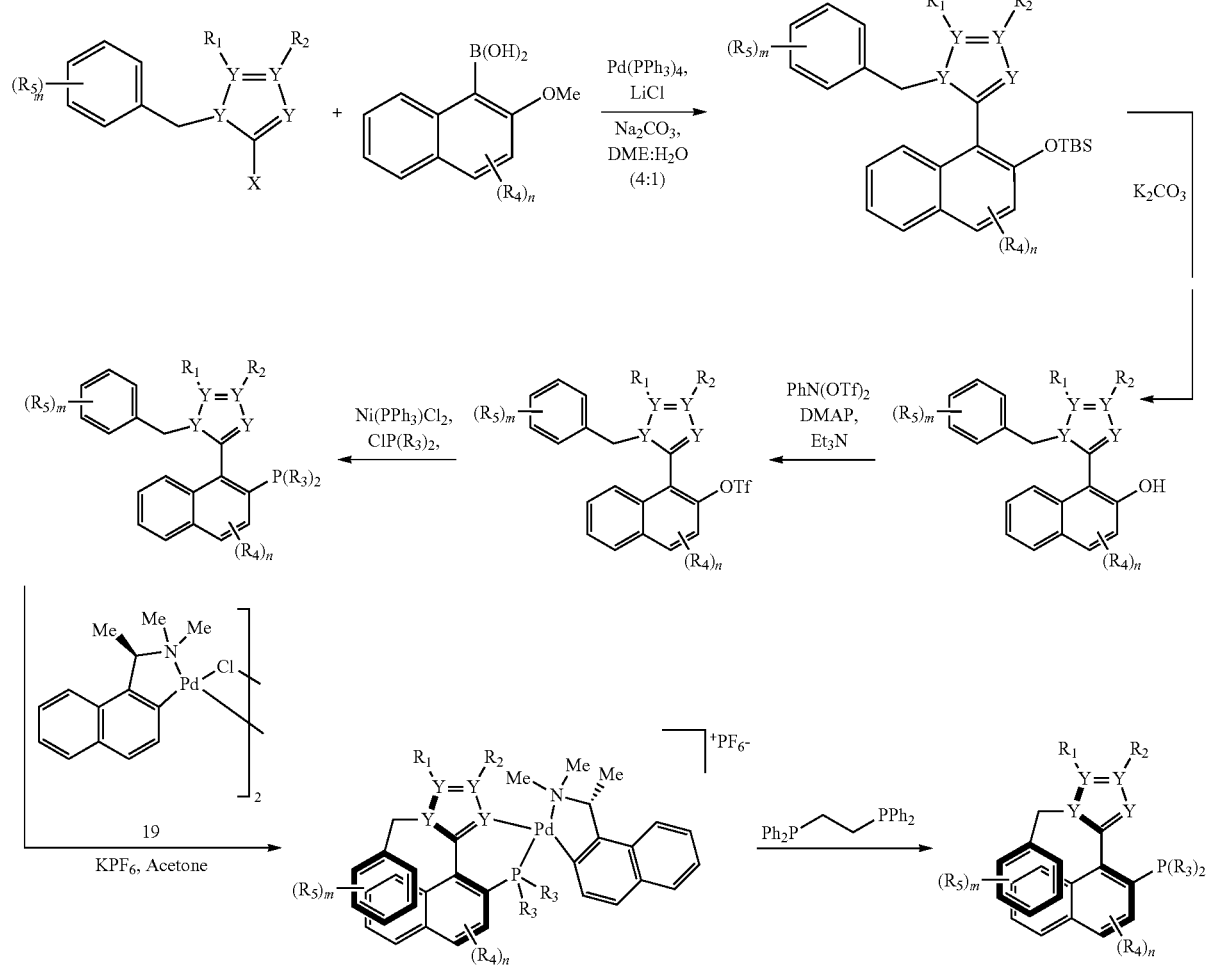

carbon atom cyclic alkyl group, a 1 to 20 carbon atom linear alkyl group, and an aryl group, wherein X1 is Cl, Br, or I and wherein Y is C, N, O, or S, wherein $R_1$ group and $R_2$ group are independently selected from the group consisting of: hydrogen, a halogen group, a 3 to 10 carbon atom cyclic alkyl group, a 1 to 20 carbon atom linear alkyl group, an aryl group, a —OR group, a —SR group, a —SiR$_{(3)}$ group, a NR$_{(2)}$ cyclic, and NR$_{(2)}$ linear group, wherein each of the $R_4$ groups is independently selected from the group consisting of: hydrogen, a halogen group, a 3 to 10 carbon atom cyclic alkyl group, a 1 to 20 carbon atom linear alkyl group, an aryl group, a —OR group, a —SR group, a —SiR$_{(3)}$ group, a NR$_{(2)}$ cyclic group, and a NR$_{(2)}$ linear group, wherein m is 1 to 5, wherein each of the $R_3$ groups is independently selected from: hydrogen, a 3 to 10 carbon atom cyclic alkyl group, a 1 to 20 carbon atom linear alkyl group, an alkoxide, a phenoxide, an aryl group, and an amine, wherein DME is dimethoxyethan, TBS is tert-butyldimethylsilyl group, Tf is triflate group, DMAP is 4-dimethylaminopyridine.

2. A method of forming a compound, comprising:

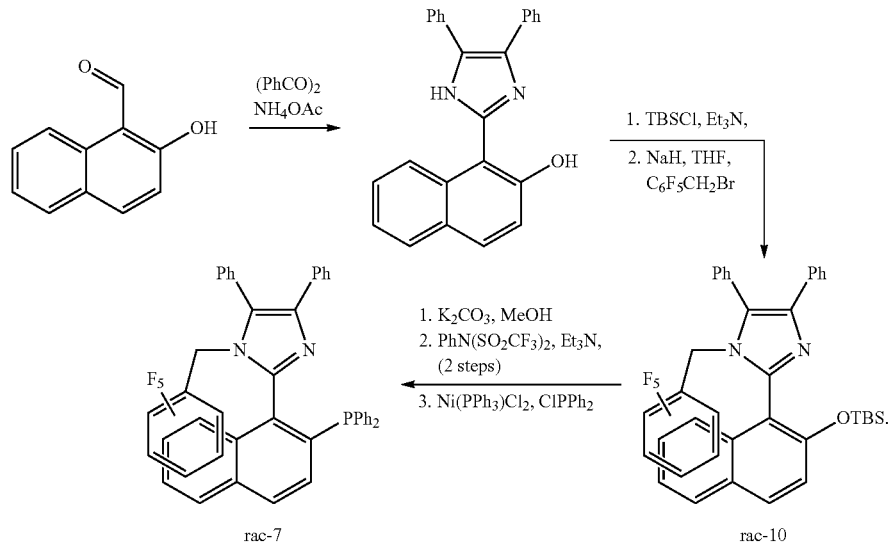

wherein $F_5$ represents a F attached to each of the 5 carbons of the ring, wherein TBS is tert-butyldimethylsilyl group.

3. A method of forming a compound, comprising:

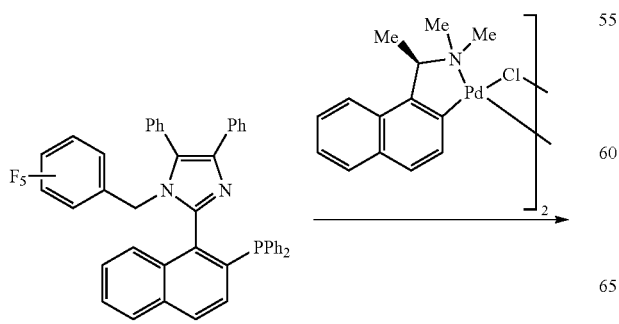

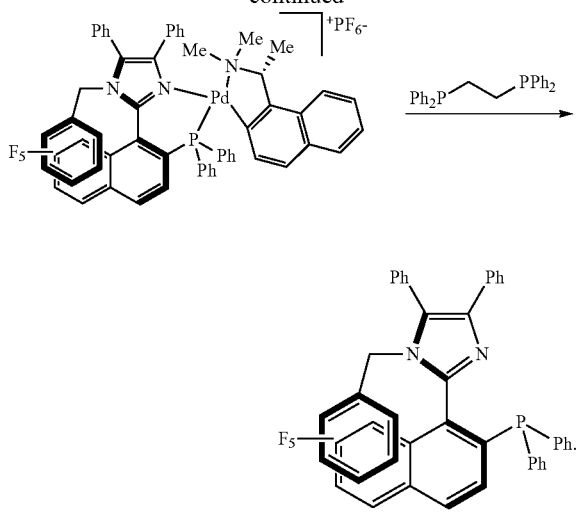

wherein $F_5$ represents a F attached to each of the 5 carbons of the ring.

4. A method of using a biaryl compound, comprising:
using a biaryl compound as a catalyst in a reaction selected from one of the following: an enantioselective transformation, an alkyne addition asymmetric allylic alkylation, and an addition to an aliphatic or an aromatic aldehyde, wherein the biaryl compound has the following structure:

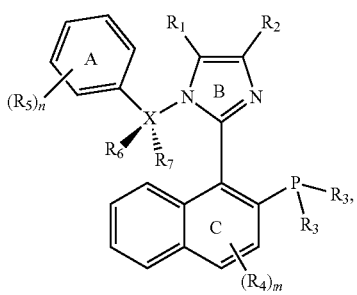

wherein each of the $R_5$ groups is independently selected from: hydrogen, a halogen group, a cyclic or linear, alkyl group, an aryl group, a —OR group, a —SR group, a —SiR$_{(3)}$ group, a NR$_{(2)}$ cyclic or linear group, wherein each R is independently selected from: hydrogen, a cyclic or linear, alkyl group, or an aryl group, wherein n is 1 to 5, wherein X is C or S, wherein each $R_6$ and $R_7$ group is independently selected from: hydrogen, a cyclic or linear, alkyl group, an aryl group, wherein $R_1$ group and $R_2$ group are independently selected from: hydrogen, a halogen group, a cyclic or linear, alkyl group, an aryl group, a —OR group, a —SR group, a —SiR$_{(3)}$ group, a NR$_{(2)}$ cyclic or linear group, wherein each of the $R_4$ groups is independently selected from: hydrogen, a halogen group, a cyclic or linear, alkyl group, an aryl group, a —OR group, a —SR group, a —SiR$_{(3)}$ group, a NR$_{(2)}$ cyclic or linear group, wherein m is 1 to 5, wherein each of the $R_3$ groups is independently selected from: hydrogen, a cyclic or linear alkyl group, an alkoxide, a phenoxide, an aryl group, or a substituted amine.

5. A method comprising:

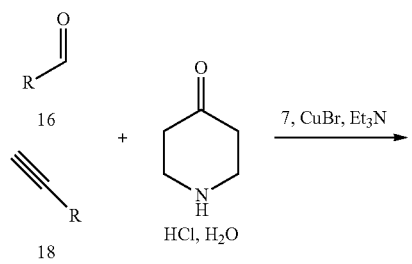

wherein compound 7 is

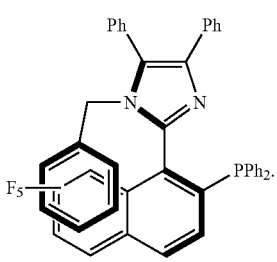

wherein $F_5$ represents a F attached to each of the 5 carbons of the ring, and wherein R is selected from SiMe$_3$ and Ph.

6. A method, comprising:

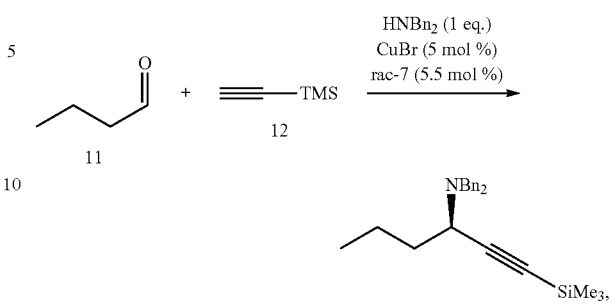

wherein compound rac-7 is

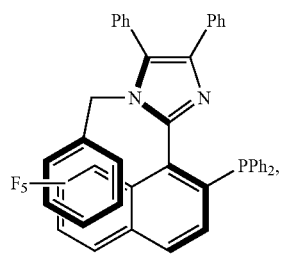

wherein $F_5$ represents a F attached to each of the 5 carbons of the ring, wherein TMS is a trimethylsilyl group.

7. A method, comprising:

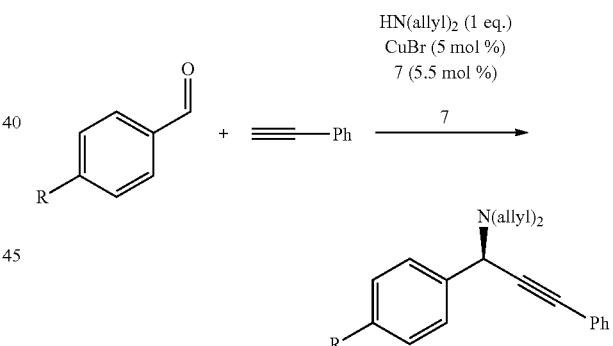

wherein compound 7 is

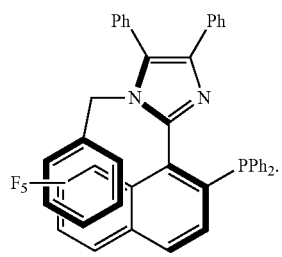

wherein $F_5$ represents a F attached to each of the 5 carbons of the ring, wherein R is selected from the group consisting of H, OMe, and CF$_3$.

8. A method comprising:
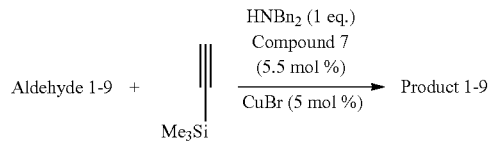 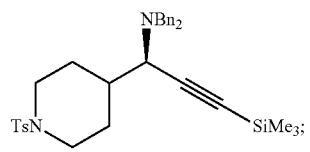
wherein aldehyde 1 is
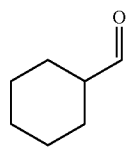
and product 1 is
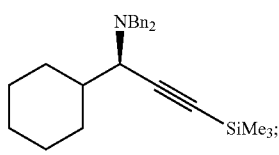
or
wherein aldehyde 2 is
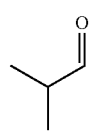
and product 2 is
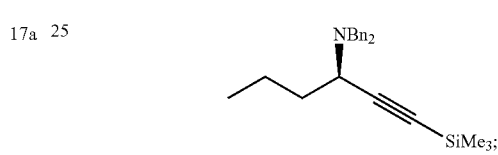
or
wherein aldehyde 3 is
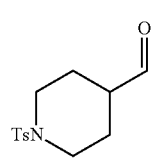
and product 3 is
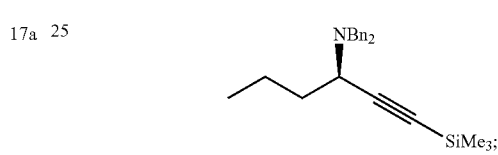
or
wherein aldehyde 4 is
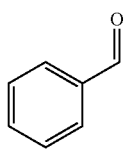
and product 4 is
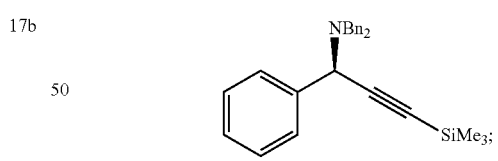
or
wherein aldehyde 5 is
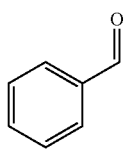
and product 5 is
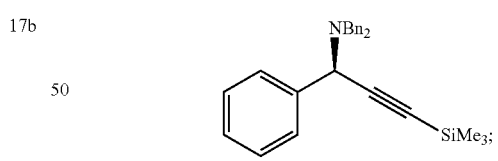
or
wherein aldehyde 6 is
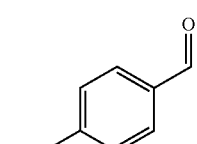

and product 6 is
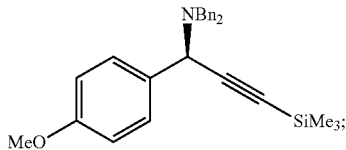
or
wherein aldehyde 7 is
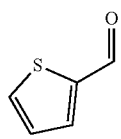
and product 7 is
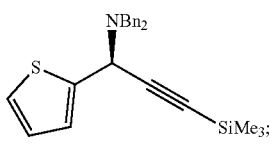
or
wherein aldehyde 8 is
16g
and product 8 is
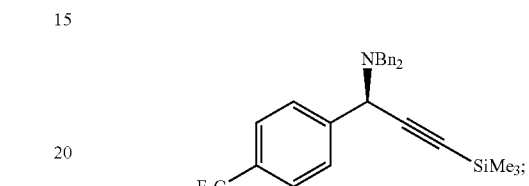
17g
and
wherein compound 7 is
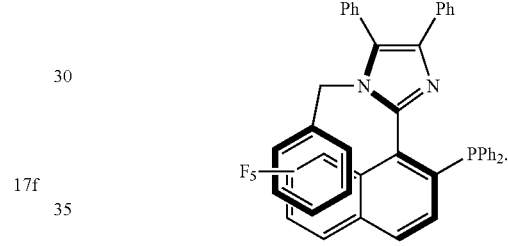
wherein $F_5$ represents a F attached to each of the 5 carbons of the ring.
* * * * *